(12) United States Patent
Bunker et al.

(10) Patent No.: US 6,849,648 B2
(45) Date of Patent: Feb. 1, 2005

(54) PHENYLENE ALKYNE MATRIX METALLOPROTEINASE INHIBITORS

(75) Inventors: Amy Mae Bunker, Ann Arbor, MI (US); William Glen Harter, Chelsea, MI (US); James Lester Hicks, Chelsea, MI (US); Patrick Michael O'Brien, Stockbridge, MI (US); Ly Pham, Ann Arbor, MI (US); Joseph Armand Picard, Canton, MI (US); William Howard Roark, Ann Arbor, MI (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 10/264,764

(22) Filed: Oct. 4, 2002

(65) Prior Publication Data

US 2003/0144274 A1 Jul. 31, 2003

Related U.S. Application Data

(60) Provisional application No. 60/395,254, filed on Jul. 12, 2002, and provisional application No. 60/329,216, filed on Oct. 12, 2001.

(51) Int. Cl.$^7$ ............... C07D 213/56; C07C 233/87; C07C 317/14; A61K 31/166; A61P 19/12
(52) U.S. Cl. ............. 514/346; 514/357; 514/359; 514/383; 514/539; 514/563; 514/603; 514/617; 514/618; 514/619; 514/674; 514/764; 546/300; 546/337; 548/255; 548/267.6; 558/415; 560/17; 560/41; 562/449; 562/450
(58) Field of Search ................... 514/357, 359, 514/363, 603, 617, 674, 764, 346, 383, 539, 563, 618, 619; 546/330, 337, 300; 548/255, 267.6; 558/415; 562/449, 450; 564/86, 185, 162; 585/25; 560/17, 41

(56) References Cited

U.S. PATENT DOCUMENTS

| | | | |
|---|---|---|---|
| 3,655,679 A | | 4/1972 | Shen et al. |
| 4,412,856 A | * | 11/1983 | Brunner et al. ............ 504/326 |
| 4,818,819 A | | 4/1989 | Taylor et al. ............... 544/279 |
| 4,902,796 A | | 2/1990 | Taylor et al. ............... 544/279 |
| 5,389,631 A | | 2/1995 | Claremon et al. |
| 5,646,141 A | | 7/1997 | Varney et al. ........... 514/222.8 |
| 5,929,097 A | | 7/1999 | Levin et al. ................ 514/351 |
| 5,948,780 A | | 9/1999 | Peterson, Jr. et al. ....... 514/255 |
| 5,990,116 A | * | 11/1999 | Nussbaumer ............ 514/266.1 |
| 6,008,243 A | | 12/1999 | Bender et al. ............. 514/422 |
| 6,225,311 B1 | | 5/2001 | Levin et al. ............. 514/227.5 |
| 2002/0151555 A1 | | 10/2002 | Barvian et al. ............ 514/256 |
| 2002/0151558 A1 | | 10/2002 | Andrianjara et al. ........ 514/267 |
| 2002/0156061 A1 | | 10/2002 | Barvian et al. ............ 514/183 |
| 2002/0156069 A1 | | 10/2002 | Picard et al. ............ 514/223.2 |
| 2002/0161000 A1 | | 10/2002 | Barvian et al. ........ 514/217.04 |
| 2002/0193377 A1 | | 12/2002 | Andrianjara et al. |
| 2003/0004172 A1 | | 1/2003 | Harter et al. |
| 2003/0130278 A1 | | 7/2003 | Gaudilliere et al. |
| 2004/0043979 A1 | | 3/2004 | Picard |
| 2004/0048863 A1 | | 3/2004 | Bunker et al. |
| 2004/0053952 A1 | | 3/2004 | Hicks et al. |
| 2004/0063673 A1 | | 4/2004 | Johnson |

FOREIGN PATENT DOCUMENTS

| | | |
|---|---|---|
| EP | 0418797 B1 | 8/1994 |
| EP | 0463592 B1 | 8/1994 |
| EP | 0935963 | 8/1999 |
| EP | 1138680 | 10/2001 |
| JP | 8-143568 A | 6/1996 |
| JP | 10/195063 A2 * | 7/1998 |
| WO | WO 96/16046 A2 * | 5/1996 |
| WO | 9616046 | 5/1996 |
| WO | WO 96/33181 A1 * | 10/1996 |
| WO | WO 97/03967 A1 * | 2/1997 |
| WO | 9816514 | 4/1998 |
| WO | WO 99/02497 A2 * | 1/1999 |
| WO | WO 00/09485 | 2/2000 |
| WO | WO 2000/007999 A1 * | 2/2000 |
| WO | 0035906 | 6/2000 |
| WO | 0040561 | 7/2000 |
| WO | 0045063 | 8/2000 |
| WO | WO 01/12611 | 2/2001 |
| WO | WO 2001/053274 A1 * | 7/2001 |
| WO | 0155133 | 8/2001 |
| WO | 0163244 | 8/2001 |
| WO | 0206513 | 1/2002 |
| WO | WO 02/34726 | 5/2002 |
| WO | WO 02/34753 | 5/2002 |
| WO | 02064080 | 8/2002 |
| WO | 02064547 | 8/2002 |
| WO | 02064568 | 8/2002 |
| WO | 02064571 | 8/2002 |
| WO | 02064572 | 8/2002 |
| WO | 02064578 | 8/2002 |
| WO | 02064595 | 8/2002 |
| WO | 02064598 | 8/2002 |
| WO | 02064599 | 8/2002 |
| WO | WO 2003/033478 A1 | 4/2003 |
| WO | WO03/049738 A1 | 6/2003 |
| WO | WO 2004/014366 A1 | 2/2004 |
| WO | WO 2004/014384 A2 | 2/2004 |
| WO | WO 2004/014868 A2 | 2/2004 |
| WO | WO 2004/014892 A1 | 2/2004 |

OTHER PUBLICATIONS

Watanabe, Shin–Ichi; Yamamoto, Keiichirou; Itagaki, Yukiko; Iwamura, Tatsunori; Iwama, Tetsuo; Kataoka, Tadashi, Tetrahedron, 56(6), 855–863 (English) 2000.*

(List continued on next page.)

Primary Examiner—Thomas McKenzie
(74) Attorney, Agent, or Firm—Pfizer Inc.; Claude F. Purchase, Jr.

(57) ABSTRACT

A compound of Formula I

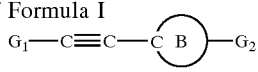

or a pharmaceutically acceptable salt thereof, or a tautomer thereof, wherein $G_1$, $G_2$, and B are as defined in the application, are selective inhibitors of MMP-13. The compounds are useful for treating diseases mediated by MMP-13, including cancer and arthritis.

6 Claims, No Drawings

OTHER PUBLICATIONS

Shen, Dong; Diele, Siegmar; Pelzl, Gerhard; Wirth, Ina; Tschierske, Carsten, Journal of Materials Chemistry, 9(3), 661–672 (English) 1999.*

Whittaker, Mark et al, Celltransmissions, vol. 17, No. 1, 2001, pp. 3–14.*

Aldrich Chemical Company, Milwaukee, WI, 1992, p. 989, entry 11,770–6.* van den Berg WB, Lessons from animal models of osteoarthritis, Curr Opin Rheumatol Sep. 2001;13(5):452–6, (abstract) Medline [online].Bethesda, MD, USA: United States National Library of Medicine, [retrieved on May 21, 2003]..*

Pendas AM, An overview of collagenase–3 expression in malignant tumors and analysis of its potential value as a target in antitumor therapies, Clin Chim Acta Feb. 15, 2000;291(2):137–55, (abstract) Medline [online]. NLM [retrieved on May 21, 2003]..*

Draetta, G. and Pagano, M. in "Annual Reports in Medicinal Chemistry, vol. 31", 1996, Academic Press, San Diego, p 241–246.*

Polman, C.H. et al, BMJ 2000, 321, 490–4.*

Cohen, J.A. et al, J. Neuroimmun., 1999, 98 29–36.*

John Montana & Andrew Baxter, "The design of selective non–substrate–based matrix metalloproteinase inhibitors", Current Opinion in Drug Discovery & Development 2000, 3(4):353–361.

Clark et al., "Matrix metalloproteinase inhibitors in the treatment of arthritis", Current Opinion in Anti–inflammatory & Immunomodulatory Investigational Drugs 2000, 2(1):16–25.

Chen et al., "Structure–Based Design of a Novel, Potent, and Selective Inhibitor for MMP–13 Utilizing NMR Spectroscopy and Computer–Aided Molecular Design", J. Am. Chem. Soc. 2000, 122–9648–9654.

M.G. Natchus, et al., "Development of New Carboxylic Acid–Based MMP Inhibitors Derived from Functionalized Propargylglycines", Journal of Medicinal Chemistry 2001, 44(7):1060–1071, Derwent Publication Lt. Abstract No. 2001–514548; XP002213435.

A.B. Dyatkin et al., "The Solid Phase Synthesis of Complex Propargylamines Using the Combination of Sonogashira and Mannich Reactions", Tetrahedron Letters, Elsevier Science Publishers, Amsterdam, NL 1998, 39(22)3647–3650.

E.C. Taylor, et al., "Pteridines. 51. A New and Unequivocal Route to C–6 Carbon–Substituted Pterins and Pteridines", J. Org. Chem. 1987, 52:3997–4000.

E.C. Taylor, et al., "Convergent and Efficient Palladium–Effected Synthesis of 5,10–Dideaza–5,6,7,8–tetrahydrofolic Acid (DDA THF)", J. Org. Chem. 1989, 52:3618–3624.

Freije, Jose M., et al, "Molecular Cloning and Expression of Collagenase–3, a Novel Human Matrix Metalloproteinase Produced by Breast Carcinomas", The Jouranl of Biological Chemistry, 1994; 269(24): pp 16766–16773.

Mitchell, Peter G., et al, "Cloning, Expression, and Type II Collagenolytic Activity of Matrix Metalloproteinase–13 from Human Osteoarthritic Cartilage", J. Clin. Invest. 1996; 97(3): pp 761–768.

Beckett, R. Paul, et al, "Matrix Metalloproteinase Inhibitors 1998", Exp. Opin. Ther. Patents, 1998; 8(3): pp 259–260.

U.S. Appl. No. 10/071,032, filed Feb. 8, 2002, Dyer et al.

Lisa A. Neuhold, et al., "Postnatal expression in hyaline cartilage of constitutively active human collagenase–3 (MMP–13) induces osteoarthritis in mice", J. Clin. Invest.., vol. 107, No. 1, Jan. 2001, pp 35–44.

Leif Dahlberg, et al., "Selective Enhancement of Collagenase–mediated Cleavage of Resident Type II Collagen In Cultured Osteoarthritic Cartilage and Arrest with a Synthetic Inhibitor that Spares Collagenase 1 (Matrix Metalloproteinase 1)". Arthritis & Rheumatism, vol. 43, No. 3, Mar. 2000, pp 673–682.

R. Clark Billinghurst, et al., "Comparison of the degradation of type II collagen and Proteoglycan in nasal and articular cartilages induced by interleukin–1 and the selective inhibition of type II collagen cleavage of collagenase", Arthritis & Rheumatism, vol. 43, No. 3, Mar. 2000, pp 664–672.

Peter G. Mitchell, et al., "Cloning, Expression, and Type II Collagenolytic Activity of Matrix Metalloproteinase–13 from Human Osteoarthritic Cartilage", J. Clin. Invest., vol. 97, No. 3, Feb. 1996, pp 761–768.

R. Clark Billinghurst, et al., "Enhanced Cleavage of Type II Collagen by Collagenases in Osteoarthritic Articular Cartilage", J. Clin. Invest., vol. 97, No. 7, Apr. 1997, pp 1534–1545.

Kosaku Hirota, et al. "Novel Synthesis of Pyrido[3,4–d] Pyrimidines, Pyrido[2,3–d]–Pyrimidines, and Quinazolines via Palladium–Catalyzed Oxidative Coupling", Heterocycles, vol. 37, No. 1, 1994, pp 563–570.

* cited by examiner

PHENYLENE ALKYNE MATRIX METALLOPROTEINASE INHIBITORS

CROSS-REFERENCES TO RELATED APPLICATIONS

This application claims benefit of priority from PCT International patent application no. PCT/IB02/03057, filed Aug. 2, 2002, and U.S. provisional patent application Nos. 60/395,254, filed Jul. 12, 2002, and 60/329,216, filed Oct. 12, 2001.

FIELD OF THE INVENTION

This invention relates to a group of alkyne derivatives that inhibit matrix metalloproteinase enzymes and are thus useful for treating diseases resulting from tissue breakdown, such as heart disease, multiple sclerosis, arthritis, including osteoarthritis and rheumatoid arthritis, atherosclerosis, age-related macular degeneration, chronic obstructive pulmonary disease, psoriasis, asthma, cardiac insufficiency, inflammatory bowel disease, periodontal diseases, and osteoporosis.

BACKGROUND OF THE INVENTION

Matrix metalloproteinases (sometimes referred to as MMPs) are naturally-occurring enzymes found in most mammals. Over-expression and activation of MMPs or an imbalance between MMPs and inhibitors of MMPs have been suggested as factors in the pathogenesis of diseases characterized by the breakdown of extracellular matrix or connective tissues.

Stromelysin-1 and gelatinase A are members of the matrix metalloproteinases (MMP) family. Other members include fibroblast collagenase (MMP-1), neutrophil collagenase (MMP-8), gelatinase B (92 kDa gelatinase) (MMP-9), stromelysin-2 (MMP-10), stromelysin-3 (MMP-11), matrilysin (MMP-7), collagenase 3 (MMP-13), TNF-alpha converting enzyme (TACE), and other newly discovered membrane-associated matrix metalloproteinases (Sato H., Takino T., Okada Y., Cao J., Shinagawa A., Yamamoto E., and Seiki M., Nature, 1994;370:61–65). These enzymes have been implicated with a number of diseases which result from breakdown of connective tissue, including such diseases as rheumatoid arthritis, osteoarthritis, osteoporosis, periodontitis, multiple sclerosis, gingivitis, corneal epidermal and gastric ulceration, atherosclerosis, neointimal proliferation which leads to restenosis and ischemic heart failure, and tumor metastasis. A method for preventing and treating these and other diseases is now recognized to be by inhibiting metalloproteinase enzymes, thereby curtailing and/or eliminating the breakdown of connective tissues that results in the disease states.

The catalytic zinc in matrix metalloproteinases is typically the focal point for inhibitor design. The modification of substrates by introducing zinc-chelating groups has generated potent inhibitors such as peptide hydroxamates and thiol-containing peptides. Peptide hydroxamates and the natural endogenous inhibitors of MMPs (TIMPs) have been used successfully to treat animal models of cancer and inflammation. MMP inhibitors have also been used to prevent and treat congestive heart failure and other cardiovascular diseases, U.S. Pat. No. 5,948,780.

A major limitation on the use of currently known MMP inhibitors is their lack of specificity for any particular enzyme. Recent data has established that specific MMP enzymes are associated with some diseases, with no effect on others. The MMPs are generally categorized based on their substrate specificity, and indeed the collagenase subfamily of MMP-1, MMP-8, and MMP-13 selectively cleave native interstitial collagens, and thus are associated only with diseases linked to such interstitial collagen tissue. This is evidenced by the recent discovery that MMP-13 alone is over expressed in breast carcinoma, while MMP-1 alone is over expressed in papillary carcinoma (see Chen et al., J. Am. Chem. Soc., 2000;122:9648–9654).

There appears to be few selective inhibitors of MMP-13 reported. A compound named WAY-170523 has been reported by Chen et al., supra., 2000, and a few other compounds are reported in PCT International Publication No. WO 01/63244 A1, as allegedly selective inhibitors of MMP-13. Further, U.S. Pat. No. 6,008,243 discloses inhibitors of MMP-13. However, no selective or nonselective inhibitor of MMP-13 has been approved and marketed for the treatment of any disease in any mammal. Accordingly, the need continues to find new low molecular weight compounds that are potent and selective MMP inhibitors, and that have an acceptable therapeutic index of toxicity/potency to make them amenable for use clinically in the prevention and treatment of the associated disease states. An object of this invention is to provide a group of selective MMP-13 inhibitor compounds characterized as being alkynes.

SUMMARY OF THE INVENTION

This invention provides a group of alkyne compounds that are inhibitors of matrix metalloproteinase enzymes, and especially MMP-13. The invention is more particularly directed to compounds defined by Formula I

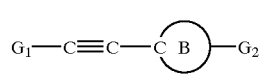

or a pharmaceutically acceptable salt thereof, or a tautomer thereof, wherein:

$G_1$ and $G_2$ independently are

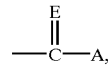

wherein
E is independently O or S;
A is $OR_1$ or $NR_1R_2$;
$R_1$ and $R_2$ independently are hydrogen, $C_1$–$C_6$ alkyl, $C_2$–$C_6$ alkenyl, $C_2$–$C_6$ alkynyl, $(CH_2)_n$aryl, $(CH_2)_n$cycloalkyl, or $(CH_2)_n$heteroaryl, or $R_1$ and $R_2$ are taken together with the nitrogen atom to which they are attached to complete a 3- to 8-membered ring having carbon atoms, the nitrogen atom bearing $R_1$ and $R_2$, and 0 or 1 heteroatom selected from N(H), N(CH$_3$), O, and S, and which ring is optionally unsubstituted or substituted with =O, halo, or methyl, wherein
n is an integer of from 0 to 6; or
$G_1$ and $G_2$ independently are hydrogen, halo, $C_1$–$C_6$ alkyl, $C_2$–$C_6$ alkenyl, $C_2$–$C_6$ alkynyl, $(CH_2)_m$OH, $(CH_2)_m$OR$_3$, $(CH_2)_m$cycloalkyl, $(CH_2)_m$aryl, $(CH_2)_m$ substituted aryl, $(CH_2)_m$heteroaryl, $(CH_2)_m$substituted heteroaryl, $CH(OH)(CH_2)_m$aryl, $CHOH(CH_2)_m$ substituted aryl, $CH(OH)(CH_2)_m$heteroaryl, $CH(OH)(CH_2)_m$ substituted heteroaryl, $(CO_2)_q(CH_2)_m$aryl, $(CO_2)_q$ $(CH_2)_m$substituted aryl, $(CO_2)_q(CH_2)_m$heteroaryl, $(CO_2)_q(CH_2)_m$substituted heteroaryl, $(CO_2)_q(CH_2)_m$ carbocycle, $(CO_2)_q(CH_2)_m$heterocycle, $(CO_2)_q(CH_2)_m$ $NR_3R_4$, $(CH_2)_mC(O)R_3$, $(CH_2)_mC(O)OR_3$, $(CH_2)_mC(O)NR_3R_4$, $(CH_2)_mC(S)NR_3R_4$, or $(CH_2)_mC(NH)NR_3R_4$;

m is an integer of from 0 to 6;

q is an integer of 0 or 1;

$R_3$ and $R_4$ independently are hydrogen, $C_1$–$C_6$ alkyl, $(CH_2)_m$aryl, or $(CH_2)_m$heteroaryl, or $R_3$ and $R_4$ are taken together with the nitrogen atom to which they are attached to complete a 3- to 7-membered ring having carbon atoms, the nitrogen atom bearing $R_3$ and $R_4$, and 0 or 1 heteroatoms selected from N(H), N($CH_3$), O, and S;

B is:

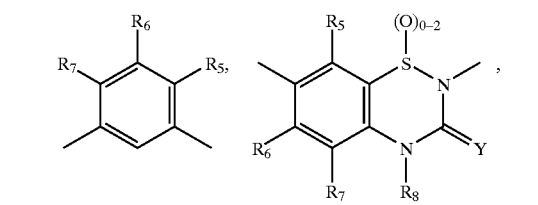

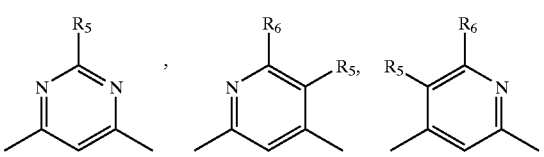

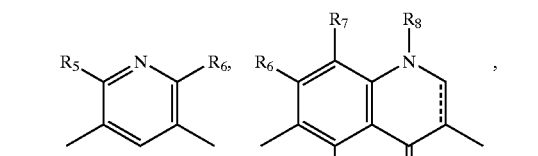

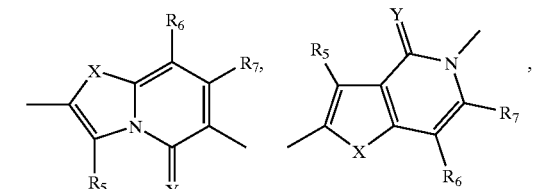

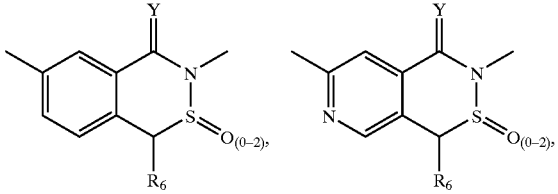

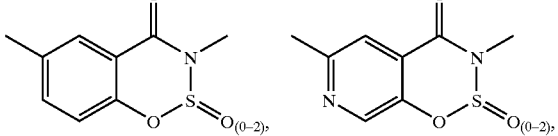

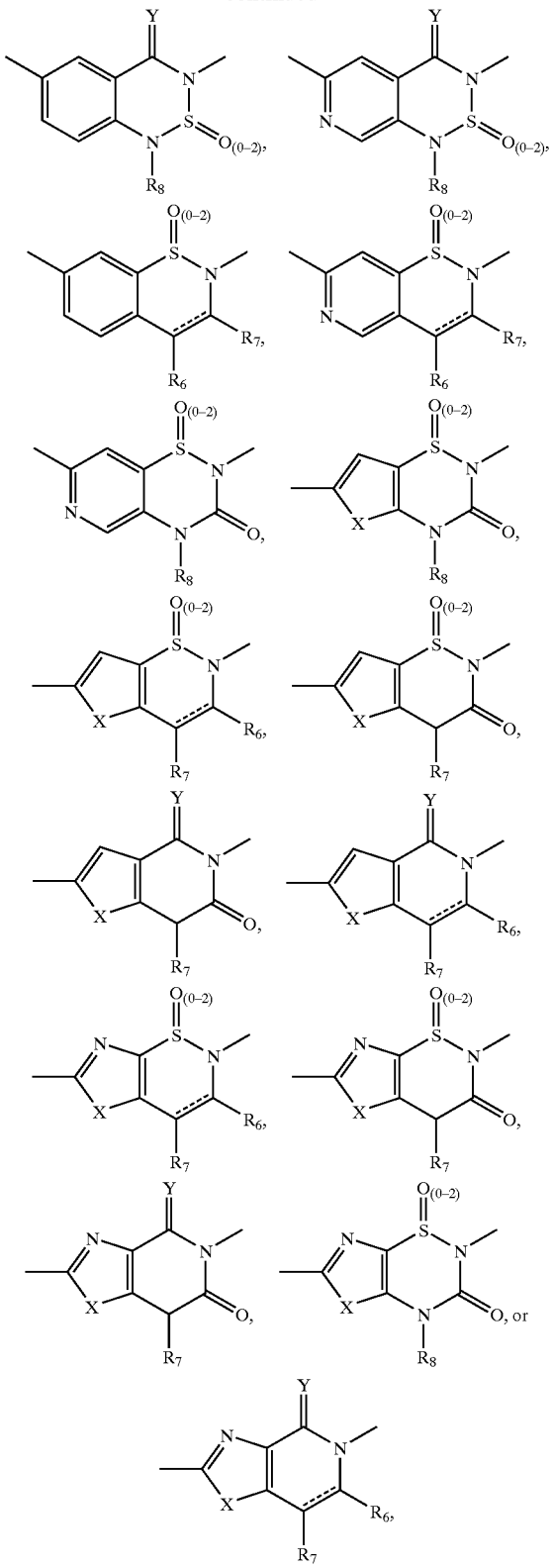

wherein:
each Y is independently O or S;
$R_5$, $R_6$, and $R_7$ independently are hydrogen, halo, hydroxy, $C_1$–$C_6$ alkyl, $C_1$–$C_6$ alkoxy, $C_2$–$C_6$ alkenyl, $C_2$–$C_6$ alkynyl, $NO_2$, $NR_9R_{10}$, CN, or $CF_3$, wherein $R_9$ and $R_{10}$ independently are hydrogen, $C_1$–$C_6$ alkyl, $C_3$–$C_7$ cycloalkyl, phenyl, or benzyl, or $R_9$ and $R_{10}$ are taken together with the nitrogen atom to which they are attached to form a 3- to 7-membered ring having carbon atoms, the nitrogen atom bearing $R_9$ and $R_{10}$, and 0 or 1 atoms selected from O, S, N(H), and N(CH$_3$);

$R_8$ is hydrogen, $C_1$–$C_6$ alkyl, $C_2$–$C_6$ alkenyl, $C_2$–$C_6$ alkynyl, CH$_2$CO$_2$H, OH, NH$_2$, or $C_1$–$C_6$ alkanoyl;

X is S, S(O), S(O)$_2$, O, N(R$_8$), wherein R$_8$ is as defined above, C(=O), or CH$_2$; and

- - - is a bond or is absent.

Preferred is a compound of Formula I, or a pharmaceutically acceptable salt thereof, or tautomer thereof, wherein $G_1$ and $G_2$ independently are
(CH$_2$)$_m$aryl,
(CH$_2$)$_m$substituted aryl,
(CH$_2$)$_m$heteroaryl, or
(CH$_2$)$_m$substituted heteroaryl, wherein m is an integer of from 0 to 6 and aryl, substituted aryl, heteroaryl, and substituted heteroaryl are as defined above for Formula I.

Another embodiment of the invention is a compound according to Formula I of Formula II

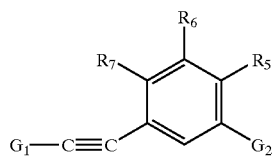

II or a pharmaceutically acceptable salt thereof, or a tautomer thereof, wherein:

$G_1$ and $G_2$ independently are

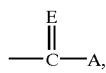

wherein
E is independently O or S;
A is OR$_1$ or NR$_1$R$_2$;
$R_1$ and $R_2$ independently are hydrogen, $C_1$–$C_6$ alkyl, $C_2$–$C_6$ alkenyl, $C_2$–$C_6$ alkynyl, (CH$_2$)$_n$aryl, (CH$_2$)$_n$cycloalkyl, or (CH$_2$)$_n$heteroaryl, or $R_1$ and $R_2$ are taken together with the nitrogen atom to which they are attached to complete a 3- to 8-membered ring having carbon atoms, the nitrogen atom bearing $R_1$ and $R_2$, and 0 or 1 heteroatom selected from N(H), N(CH$_3$), O, and S, and which ring is optionally unsubstituted or substituted with =O, halo, or methyl, wherein n is an integer of from 0 to 6; or $G_1$ and $G_2$ independently are hydrogen, halo, $C_1$–$C_6$ alkyl, $C_2$–$C_6$ alkenyl, $C_2$–$C_6$ alkynyl, (CH$_2$)$_m$OH, (CH$_2$)$_m$OR$_3$, (CH$_2$)$_m$cycloalkyl, (CH$_2$)$_m$aryl, (CH$_2$)$_m$substituted aryl, (CH$_2$)$_m$heteroaryl, (CH$_2$)$_m$substituted heteroaryl, CH(OH)(CH$_2$)$_m$aryl, CHOH(CH$_2$)$_m$ substituted aryl, CH(OH)(CH$_2$)$_m$heteroaryl, CH(OH)(CH$_2$)$_m$ substituted heteroaryl, (CO$_2$)$_q$(CH$_2$)$_m$aryl, (CO$_2$)$_q$(CH$_2$)$_m$substituted aryl, (CO$_2$)$_q$(CH$_2$)$_m$ heteroaryl, (CO$_2$)$_q$(CH$_2$)$_m$substituted heteroaryl, (CO$_2$)$_q$(CH$_2$)$_m$ carbocycle, (CO$_2$)$_q$(CH$_2$)$_m$heterocycle, (CO$_2$)$_q$(CH$_2$)$_m$ NR$_3$R$_4$, (CH$_2$)$_m$C(O)R$_3$, (CH$_2$)$_m$C(O)OR$_3$, (CH$_2$)$_m$C(O)NR$_3$R$_4$, (CH$_2$)$_m$C(S)NR$_3$R$_4$, or (CH$_2$)$_m$C(NH)NR$_3$R$_4$;

m is an integer of from 0 to 6;
q is an integer of 0 or 1;
$R_3$ and $R_4$ independently are hydrogen, $C_1$–$C_6$ alkyl, (CH$_2$)$_m$aryl, or (CH$_2$)$_m$heteroaryl, or $R_3$ and $R_4$ are taken together with the nitrogen atom to which they are attached to complete a 3- to 7-membered ring having carbon atoms, the nitrogen atom bearing $R_3$ and $R_4$, and 0 or 1 heteroatoms selected from N(H), N(CH$_3$), O, and S; and $R_5$, $R_6$, and $R_7$ independently are hydrogen, halo, hydroxy, $C_1$–$C_6$ alkyl, $C_2$–$C_6$ alkenyl, $C_2$–$C_6$ alkynyl, $C_1$–$C_6$ alkoxy, NO$_2$, CN, CF$_3$, or NR$_9$R$_{10}$, wherein $R_9$ and $R_{10}$ independently are hydrogen, $C_1$–$C_6$ alkyl, $C_3$–$C_7$ cycloalkyl, phenyl, or benzyl, or $R_9$ and $R_{10}$ are taken together with the nitrogen atom to which they are attached to complete a 3- to 7-membered ring having carbon atoms, the nitrogen atom bearing $R_9$ and $R_{10}$, and 0 or 1 heteroatoms selected from N(H), N(CH$_3$), O, and S.

Preferred is a compound of Formula II, or a pharmaceutically acceptable salt thereof, or a tautomer thereof, wherein:

$G_1$ and $G_2$ independently are
(CH$_2$)$_m$aryl, wherein m is 1 and aryl is phenyl,
(CH$_2$)$_m$substituted aryl, wherein m is 1 and substituted aryl is 4-methoxyphenyl, 3-methoxyphenyl, 4-fluorophenyl, 3-fluorophenyl, 4-chlorophenyl, 3-chlorophenyl, 4-bromophenyl, 3-bromophenyl, 4-nitrophenyl, 3-nitrophenyl, 4-methylsulfanylphenyl, 3-methylsulfanylphenyl, 4-methylphenyl, 3-methylphenyl, 4-cyanophenyl, 3-cyanophenyl, 4-carboxyphenyl, 3-carboxyphenyl, 4-methanesulfonylphenyl, or 3-methanesulfonylphenyl,
(CH$_2$)$_m$heteroaryl, wherein m is 1 and heteroaryl is pyridin-4-yl, pyridin-3-yl, or pyridin-2-yl, or
(CH$_2$)$_m$substituted heteroaryl, wherein m is 1 and substituted heteroaryl is 2-methoxypyridin-4-yl; and
$R_5$, $R_6$, and $R_8$ are hydrogen.

More preferred is a compound of Formula II, or a pharmaceutically acceptable salt thereof, or a tautomer thereof, selected from:

3-(4-Methoxy-phenyl)-prop-1-ynyl)-N-(4-carboxybenzyl)-benzamide;

N-(4-Methanesulfonyl-benzyl)-3-(4-methoxy-phenyl)-prop-1-ynyl)-benzamide;

3-(3-Methoxy-phenyl)-prop-1-ynyl)-N-(4-carboxybenzyl)-benzamide;

N-(4-Methanesulfonyl-benzyl)-3-(3-methoxy-phenyl)-prop-1-ynyl)-benzamide;

3-(4-Cyano-phenyl)-prop-1-ynyl)-N-(4-carboxybenzyl)-benzamide;

N-(4-Methanesulfonyl-benzyl)-3-(4-cyano-phenyl)-prop-1-ynyl)-benzamide;

3-(3-Cyano-phenyl)-prop-1-ynyl)-N-(4-carboxybenzyl)-benzamide;

N-(4-Methanesulfonyl-benzyl)-3-(3-cyano-phenyl)-prop-1-ynyl)-benzamide;

3-(4-Fluoro-phenyl)-prop-1-ynyl)-N-(4-carboxybenzyl)-benzamide;

N-(4-Methanesulfonyl-benzyl)-3-(4-fluoro-phenyl)-prop-1-ynyl)-benzamide;

3-(3-Fluoro-phenyl)-prop-1-ynyl)-N-(4-carboxybenzyl)-benzamide;

N-(4-Methanesulfonyl-benzyl)-3-(3-fluoro-phenyl)-prop-1-ynyl)-benzamide;

3-(4-Chloro-phenyl)-prop-1-ynyl)-N-(4-carboxybenzyl)-benzamide;

N-(4-Methanesulfonyl-benzyl)-3-(4-chloro-phenyl)-prop-1-ynyl)-benzamide;

3-(3-Chloro-phenyl)-prop-1-ynyl)-N-(4-carboxybenzyl)-benzamide;

N-(4-Methanesulfonyl-benzyl)-3-(3-chloro-phenyl)-prop-1-ynyl)-benzamide;

3-(4-Bromo-phenyl)-prop-1-ynyl)-N-(4-carboxybenzyl)-benzamide;

N-(4-Methanesulfonyl-benzyl)-3-(4-bromo-phenyl)-prop-1-ynyl)-benzamide;

3-(3-Bromo-phenyl)-prop-1-ynyl)-N-(4-carboxybenzyl)-benzamide;

N-(4-Methanesulfonyl-benzyl)-3-(3-bromo-phenyl)-prop-1-ynyl)-benzamide;

3-(4-Methanesulfanyl-phenyl)-prop-1-ynyl)-N-(4-carboxybenzyl)-benzamide;

N-(4-Methanesulfonyl-benzyl)-3-(4-methanesulfanyl-phenyl)-prop-1-ynyl)-benzamide;

3-(3-Methanesulfanyl-phenyl)-prop-1-ynyl)-N-(4-carboxybenzyl)-benzamide;

N-(4-Methanesulfonyl-benzyl)-3-(3-methanesulfanyl-phenyl)-prop-1-ynyl)-benzamide;

3-(4-Methyl-phenyl)-prop-1-ynyl)-N-(4-carboxybenzyl)-benzamide;

N-(4-Methanesulfonyl-benzyl)-3-(4-methyl-phenyl)-prop-1-ynyl)-benzamide;

3-(3-Methyl-phenyl)-prop-1-ynyl)-N-(4-carboxybenzyl)-benzamide;

N-(4-Methanesulfonyl-benzyl)-3-(3-methyl-phenyl)-prop-1-ynyl)-benzamide;

3-(3-Pyridin-4-yl-prop-1-ynyl)-N-(4-carboxybenzyl)-benzamide;

N-(4-Methanesulfonyl-benzyl)-3-(3-pyridin-4-yl-prop-1-ynyl)-benzamide;

3-(3-Pyridin-3-yl-prop-1-ynyl)-N-(4-carboxybenzyl)-benzamide;

N-(4-Methanesulfonyl-benzyl)-3-(3-pyridin-3-yl-prop-1-ynyl)-benzamide;

3-[3-(2-Methoxy-pyridin-4-yl)-prop-1-ynyl]-N-(4-carboxybenzyl)-benzamide; and

N-(4-Methanesulfonyl-benzyl)-3-[3-(2-methoxy-pyridin-4-yl)-prop-1-ynyl]-benzamide.

Another embodiment of the invention is a compound according to Formula I of Formula III

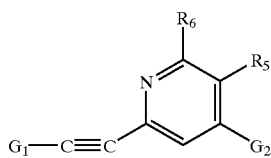

III or a pharmaceutically acceptable salt thereof, or a tautomer thereof, wherein:

$G_1$ and $G_2$ independently are

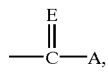

wherein
E is independently O or S;
A is $OR_1$ or $NR_1R_2$;
$R_1$ and $R_2$ independently are hydrogen, $C_1$–$C_6$ alkyl, $C_2$–$C_6$ alkenyl, $C_2$–$C_6$ alkynyl, $(CH_2)_n$aryl, $(CH_2)_n$ cycloalkyl, or $(CH_2)_n$heteroaryl, or $R_1$ and $R_2$ are taken together with the nitrogen atom to which they are attached to complete a 3- to 8-membered ring having carbon atoms, the nitrogen atom bearing $R_1$ and $R_2$, and 0 or 1 heteroatom selected from N(H), N(CH$_3$), O, and S, and which ring is optionally unsubstituted or substituted with =O, halo, or methyl, wherein n is an integer of from 0 to 6; or $G_1$ and $G_2$ independently are hydrogen, halo, $C_1$–$C_6$ alkyl, $C_2$–$C_6$ alkenyl, $C_2$–$C_6$ alkynyl, $(CH_2)_m$OH, $(CH_2)_m$OR$_3$, $(CH_2)_m$cycloalkyl, $(CH_2)_m$aryl, $(CH_2)_m$ substituted aryl, $(CH_2)_m$heteroaryl, $(CH_2)_m$substituted heteroaryl, CH(OH)(CH$_2$)$_m$aryl, CHOH(CH$_2$)$_m$ substituted aryl, CH(OH)(CH$_2$)$_m$heteroaryl, CH(OH)(CH$_2$)$_m$ substituted heteroaryl, $(CO_2)_q(CH_2)_m$aryl, $(CO_2)_q$ $(CH_2)_m$substituted aryl, $(CO_2)_q(CH_2)_m$ heteroaryl, $(CO_2)_q(CH_2)_m$substituted heteroaryl, $(CO_2)_q(CH_2)_m$ carbocycle, $(CO_2)_q(CH_2)_m$heterocycle, $(CO_2)_q(CH_2)_m$ $NR_3R_4$, $(CH_2)_mC(O)R_3$, $(CH_2)_mC(O)OR_3$, $(CH_2)_mC$ $(O)NR_3R_4$, $(CH_2)_mC(S)NR_3R_4$, or $(CH_2)_mC(NH)$ $NR_3R_4$;

m is an integer of from 0 to 6;
q is an integer of 0 or 1;
$R_3$ and $R_4$ independently are hydrogen, $C_1$–$C_6$ alkyl, $(CH_2)_m$aryl, or $(CH_2)_m$heteroaryl, or $R_3$ and $R_4$ are taken together with the nitrogen atom to which they are attached to complete a 3- to 7-membered ring having carbon atoms, the nitrogen atom bearing $R_3$ and $R_4$, and 0 or 1 heteroatoms selected from N(H), N(CH$_3$), O, and S; and $R_5$ and $R_6$ independently are hydrogen, halo, hydroxy, $C_1$–$C_6$ alkyl, $C_2$–$C_6$ alkenyl, $C_2$–$C_6$ alkynyl, $C_1$–$C_6$ alkoxy, NO$_2$, CN, CF$_3$, or $NR_9R_{10}$, wherein $R_9$ and $R_{10}$ independently are hydrogen, $C_1$–$C_6$ alkyl, $C_3$–$C_7$ cycloalkyl, phenyl, or benzyl, or $R_9$ and $R_{10}$ are taken together with the nitrogen atom to which they are attached to complete a 3- to 7-membered ring having carbon atoms, the nitrogen atom bearing $R_9$ and $R_{10}$, and 0 or 1 atoms selected from N(H), N(CH$_3$), O, and S.

Preferred is a compound of Formula III, or a pharmaceutically acceptable salt thereof, or a tautomer thereof, wherein:

$G_1$ and $G_2$ independently are
  $(CH_2)_m$aryl, wherein m is 1 and aryl is phenyl,
  $(CH_2)_m$substituted aryl, wherein m is 1 and substituted aryl is 4-methoxyphenyl, 3-methoxy phenyl, 4-fluorophenyl, 3-fluorophenyl, 4-chlorophenyl, 3-chlorophenyl, 4-bromophenyl, 3-bromophenyl, 4-nitrophenyl, 3-nitrophenyl, 4-methylsulfanylphenyl, 3-methylsulfanylphenyl, 4-methylphenyl, 3-methylphenyl, 4-cyanophenyl, 3-cyanophenyl, 4-carboxyphenyl, 3-carboxyphenyl, 4-methanesulfonylphenyl, or 3-methanesulfonylphenyl,
  $(CH_2)_m$heteroaryl, wherein m is 1 and heteroaryl is pyridin-4-yl, pyridin-3-yl, or pyridin-2-yl, or (CH$_2$)$_m$substituted heteroaryl, wherein m is 1 and substituted heteroaryl is 2-methoxypyridin-4-yl; and
R$_5$ and R$_6$ are hydrogen.

More preferred is a compound of Formula III, or a pharmaceutically acceptable salt thereof, or a tautomer thereof, selected from:

3-(4-Methoxy-phenyl)-prop-1-ynyl)-N-(4-carboxybenzyl)-isonicotinamide;

N-(4-Methanesulfonyl-benzyl)-3-(4-methoxy-phenyl)-prop-1-ynyl)-isonicotinamide;

3-(3-Methoxy-phenyl)-prop-1-ynyl)-N-(4-carboxybenzyl)-isonicotinamide;

N-(4-Methanesulfonyl-benzyl)-3-(3-methoxy-phenyl)-prop-1-ynyl)-isonicotinamide;

3-(4-Cyano-phenyl)-prop-1-ynyl)-N-(4-carboxybenzyl)-isonicotinamide;

N-(4-Methanesulfonyl-benzyl)-3-(4-cyano-phenyl)-prop-1-ynyl)-isonicotinamide;

3-(3-Cyano-phenyl)-prop-1-ynyl)-N-(4-carboxybenzyl)-isonicotinamide;

N-(4-Methanesulfonyl-benzyl)-3-(3-cyano-phenyl)-prop-1-ynyl)-isonicotinamide;

3-(4-Fluoro-phenyl)-prop-1-ynyl)-N-(4-carboxybenzyl)-isonicotinamide;

N-(4-Methanesulfonyl-benzyl)-3-(4-fluoro-phenyl)-prop-1-ynyl)-isonicotinamide;

3-(3-Fluoro-phenyl)-prop-1-ynyl)-N-(4-carboxybenzyl)-isonicotinamide;

N-(4-Methanesulfonyl-benzyl)-3-(3-fluoro-phenyl)-prop-1-ynyl)-isonicotinamide;

3-(4-Chloro-phenyl)-prop-1-ynyl)-N-(4-carboxybenzyl)-isonicotinamide;

N-(4-Methanesulfonyl-benzyl)-3-(4-chloro-phenyl)-prop-1-ynyl)-isonicotinamide;

3-(3-Chloro-phenyl)-prop-1-ynyl)-N-(4-carboxybenzyl)-isonicotinamide;

N-(4-Methanesulfonyl-benzyl)-3-(3-chloro-phenyl)-prop-1-ynyl)-isonicotinamide;

3-(4-Bromo-phenyl)-prop-1-ynyl)-N-(4-carboxybenzyl)-isonicotinamide;

N-(4-Methanesulfonyl-benzyl)-3-(4-bromo-phenyl)-prop-1-ynyl)-isonicotinamide;

3-(3-Bromo-phenyl)-prop-1-ynyl)-N-(4-carboxybenzyl)-isonicotinamide;

N-(4-Methanesulfonyl-benzyl)-3-(3-bromo-phenyl)-prop-1-ynyl)-isonicotinamide;

3-(4-Methanesulfanyl-phenyl)-prop-1-ynyl)-N-(4-carboxybenzyl)-isonicotinamide;

N-(4-Methanesulfonyl-benzyl)-3-(4-methanesulfanyl-phenyl)-prop-1-ynyl)-isonicotinamide;

3-(3-Methanesulfanyl-phenyl)-prop-1-ynyl)-N-(4-carboxybenzyl)-isonicotinamide;

N-(4-Methanesulfonyl-benzyl)-3-(3-methanesulfanyl-phenyl)-prop-1-ynyl)-isonicotinamide;

3-(4-Methyl-phenyl)-prop-1-ynyl)-N-(4-carboxybenzyl)-isonicotinamide;

N-(4-Methanesulfonyl-benzyl)-3-(4-methyl-phenyl)-prop-1-ynyl)-isonicotinamide;

3-(3-Methyl-phenyl)-prop-1-ynyl)-N-(4-carboxybenzyl)-isonicotinamide;

N-(4-Methanesulfonyl-benzyl)-3-(3-methyl-phenyl)-prop-1-ynyl)-isonicotinamide;

3-(3-pyridin-4-yl-prop-1-ynyl)-N-(4-carboxybenzyl)-isonicotinamide;

N-(4-Methanesulfonyl-benzyl)-3-(3-pyridin-4-yl-prop-1-ynyl)-isonicotinamide;

3-(3-Pyridin-3-yl-prop-1-ynyl)-N-(4-carboxybenzyl)-isonicotinamide;

N-(4-Methanesulfonyl-benzyl)-3-(3-pyridin-3-yl-prop-1-ynyl)-isonicotinamide;

3-[3-(2-Methoxy-pyridin-4-yl)-prop-1-ynyl]-N-(4-carboxybenzyl)-isonicotinamide; and N-(4-Methanesulfonyl-benzyl)-3-[3-(2-methoxy-pyridin-4-yl)-prop-1-ynyl]-isonicotinamide.

Another embodiment of the invention is a compound according to Formula I of Formula IV

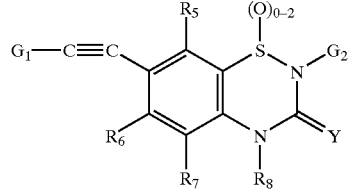

IV or a pharmaceutically acceptable salt thereof, or a tautomer thereof, wherein:

G$_1$ and G$_2$ independently are

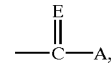

wherein

E is independently O or S;

A is OR$_1$ or NR$_1$R$_2$;

R$_1$ and R$_2$ independently are hydrogen, C$_1$–C$_6$ alkyl, C$_2$–C$_6$ alkenyl, C$_2$–C$_6$ alkynyl, (CH$_2$)$_n$aryl, (CH$_2$)$_n$cycloalkyl, or (CH$_2$)$_n$heteroaryl, or R$_1$ and R$_2$ are taken together with the nitrogen atom to which they are attached to complete a 3- to 8-membered ring having carbon atoms, the nitrogen atom bearing R$_1$ and R$_2$, and 0 or 1 heteroatom selected from N(H), N(CH$_3$), O, and S, and which ring is optionally unsubstituted or substituted with =O, halo, or methyl, wherein n is an integer of from 0 to 6; or G$_1$ and G$_2$ independently are hydrogen, halo, C$_1$–C$_6$ alkyl, C$_2$–C$_6$ alkenyl, C$_2$–C$_6$ alkynyl, (CH$_2$)$_m$OH, (CH$_2$)$_m$OR$_3$, (CH$_2$)$_m$cycloalkyl, (CH$_2$)$_m$aryl, (CH$_2$)$_m$substituted aryl, (CH$_2$)$_m$heteroaryl, (CH$_2$)$_m$substituted heteroaryl, CH(OH)(CH$_2$)$_m$aryl, CHOH(CH$_2$)$_m$ substituted aryl, CH(OH)(CH$_2$)$_m$heteroaryl, CH(OH)(CH$_2$)$_m$ substituted heteroaryl, (CO$_2$)$_q$(CH$_2$)$_m$aryl, (CO$_2$)$_q$ (CH$_2$)$_m$substituted aryl, (CO$_2$)$_q$(CH$_2$)$_m$ heteroaryl, (CO$_2$)$_q$(CH$_2$)$_m$substituted heteroaryl, (CO$_2$)$_q$(CH$_2$)$_m$ carbocycle, (CO$_2$)$_q$(CH$_2$)$_m$heterocycle, (CO$_2$)$_q$(CH$_2$)$_m$ NR$_3$R$_4$, (CH$_2$)$_m$C(O)R$_3$, (CH$_2$)$_m$C(O)OR$_3$, (CH$_2$)$_m$C (O)NR$_3$R$_4$, (CH$_2$)$_m$C(S)NR$_3$R$_4$, or (CH$_2$)$_m$C(NH) NR$_3$R$_4$;

m is an integer of from 0 to 6;

q is an integer of 0 or 1;

R$_3$ and R$_4$ independently are hydrogen, C$_1$–C$_6$ alkyl, (CH$_2$)$_m$aryl, or (CH$_2$)$_m$heteroaryl, or R$_3$ and R$_4$ are taken together with the nitrogen atom to which they are attached to complete a 3- to 7-membered ring having carbon atoms, the nitrogen atom bearing R$_3$ and $R_4$, and 0 or 1 heteroatoms selected from N(H), N(CH$_3$), O, and S;

Y is independently O or S;

$R_5$, $R_6$, and $R_7$ independently are hydrogen, halo, hydroxy, $C_1$–$C_6$ alkyl, $C_2$–$C_6$ alkenyl, $C_2$–$C_6$ alkynyl, $C_1$–$C_6$ alkoxy, NO$_2$, CN, CF$_3$, or NR$_9$R$_{10}$, wherein R$_9$ and R$_{10}$ independently are hydrogen, $C_1$–$C_6$ alkyl, $C_3$–$C_7$ cycloalkyl, phenyl, or benzyl, or R$_9$ and R$_{10}$ are taken together with the nitrogen atom to which they are attached to complete a 3- to 7-membered ring having carbon atoms, the nitrogen atom bearing R$_9$ and R$_{10}$, and 0 or 1 heteroatoms selected from N(H), N(CH$_3$), O, and S; and $R_8$ is hydrogen, $C_1$–$C_6$ alkyl, $C_2$–$C_6$ alkenyl, $C_2$–$C_6$ alkynyl, $C_1$–$C_6$ alkoxy, $C_1$–$C_6$ alkanoyl, CH$_2$CO$_2$H, NH$_2$, or OH.

Preferred is a compound of Formula IV, or a pharmaceutically acceptable salt thereof, or a tautomer thereof, wherein:

Y is O;

$G_1$ and $G_2$ independently are
(CH$_2$)$_m$aryl, wherein m is 1 and aryl is phenyl,
(CH$_2$)$_m$substituted aryl, wherein m is 1 and substituted aryl is 4-methoxyphenyl, 3-methoxyphenyl, 4-fluorophenyl, 3-fluorophenyl, 4-chlorophenyl, 3-chlorophenyl, 4-bromophenyl, 3-bromophenyl, 4-nitrophenyl, 3-nitrophenyl, 4-methylsulfanylphenyl, 3-methylsulfanylphenyl, 4-methylphenyl, 3-methylphenyl, 4-cyanophenyl, 3-cyanophenyl, 4-carboxyphenyl, 3-carboxyphenyl, 4-methanesulfonylphenyl, or 3-methanesulfonylphenyl,
(CH$_2$)$_m$heteroaryl, wherein m is 1 and heteroaryl is piperidin-1-yl, piperazin-1-yl, tetrahydrofuran-2-yl, pyridin-4-yl, pyridin-3-yl, or pyridin-2-yl,
(CH$_2$)$_m$substituted heteroaryl, wherein m is 1 and substituted heteroaryl is 2-methoxypyridin-4-yl, or
(CH$_2$)$_m$cycloalkyl, wherein m is 1 and cycloalkyl is cyclopropyl, cyclobutyl, cyclopentyl, cyclohexyl, or cycloheptyl; and $R_8$ is hydrogen or methyl.

More preferred is a compound of Formula IV, a pharmaceutically acceptable salt thereof, or a tautomer thereof, selected from:

2-Benzyl-4-methyl-1,1-dioxo-7-(3-phenyl-prop-1-ynyl)-1,4-dihydro-2H-11$^6$-benzo[1,2,4]thiadiazin-3-one;

4-[4-Methyl-1,1,3-trioxo-7-(3-phenyl-prop-1-ynyl)-3,4-dihydro-1H-11$^6$-benzo[1,2,4]thiadiazin-2-ylmethyl]-benzoic acid;

2-Benzyl-1,1-dioxo-7-(3-phenyl-prop-1-ynyl)-1,4-dihydro-2H-11$^6$-benzo[1,2,4]thiadiazin-3-one;

4-[1,1,3-Trioxo-7-(3-phenyl-prop-1-ynyl)-3,4-dihydro-1H-11$^6$-benzo[1,2,4]thiadiazin-2-ylmethyl]-benzoic acid;

2-Benzyl-4-methyl-1,1-dioxo-7-[3-(4-methoxyphenyl)-prop-1-ynyl]-1,4-dihydro-2H-11$^6$-benzo[1,2,4]thiadiazin-3-one;

2-Benzyl-1,1-dioxo-7-[3-(4-methoxyphenyl)-prop-1-ynyl]-1,4-dihydro-2H-11$^6$-benzo[1,2,4]thiadiazin-3-one;

4-{1,1,3-Trioxo-7-[3-(4-methoxyphenyl)-prop-1-ynyl]-4-methyl-3,4-dihydro-1H-11$^6$-benzo[1,2,4]thiadiazin-2-ylmethyl}-benzoic acid;

4-{1,1,3-Trioxo-7-[3-(4-methoxyphenyl)-prop-1-ynyl]-3,4-dihydro-1H-11$^6$-benzo[1,2,4]thiadiazin-2-ylmethyl}-benzoic acid;

2-Benzyl-4-methyl-1,1-dioxo-7-[3-(3-methoxyphenyl)-prop-1-ynyl]-1,4-dihydro-2H-11$^6$-benzo[1,2,4]thiadiazin-3-one;

2-Benzyl-1,1-dioxo-7-[3-(3-methoxyphenyl)-prop-1-ynyl]-1,4-dihydro-2H-11$^6$-benzo[1,2,4]thiadiazin-3-one;

4-{1,1,3-Trioxo-7-[3-(3-methoxyphenyl)-prop-1-ynyl]-4-methyl-3,4-dihydro-1H-11$^6$-benzo[1,2,4]thiadiazin-2-ylmethyl}-benzoic acid; and 4-{1,1,3-Trioxo-7-[3-(3-methoxyphenyl)-prop-1-ynyl]-3,4-dihydro-1H-11$^6$-benzo[1,2,4]thiadiazin-2-ylmethyl}-benzoic acid.

Another embodiment of the invention is a compound according to Formula I of Formula V

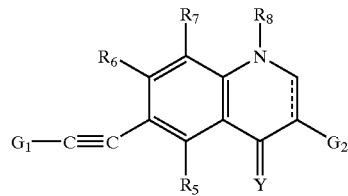

or a pharmaceutically acceptable salt thereof, or a tautomer thereof, wherein:

$G_1$ and $G_2$ independently are

wherein

E is independently O or S;

A is OR$_1$ or NR$_1$R$_2$;

$R_1$ and $R_2$ independently are hydrogen, $C_1$–$C_6$ alkyl, $C_2$–$C_6$ alkenyl, $C_2$–$C_6$ alkynyl, (CH$_2$)$_n$aryl, (CH$_2$)$_n$cycloalkyl, or (CH$_2$)$_n$heteroaryl, or $R_1$ and $R_2$ are taken together with the nitrogen atom to which they are attached to complete a 3- to 8-membered ring having carbon atoms, the nitrogen atom bearing R$_1$ and R$_2$, and 0 or 1 heteroatom selected from N(H), N(CH$_3$), O, and S, and which ring is optionally unsubstituted or substituted with =O, halo, or methyl, wherein n is an integer of from 0 to 6; or $G_1$ and $G_2$ independently are hydrogen, halo, $C_1$–$C_6$ alkyl, $C_2$–$C_6$ alkenyl, $C_2$–$C_6$ alkynyl, (CH$_2$)$_m$OH, (CH$_2$)$_m$OR$_3$, (CH$_2$)$_m$cycloalkyl, (CH$_2$)$_m$aryl, (CH$_2$)$_m$substituted aryl, (CH$_2$)$_m$heteroaryl, (CH$_2$)$_m$substituted heteroaryl, CH(OH)(CH$_2$)$_m$aryl, CHOH(CH$_2$)$_m$ substituted aryl, CH(OH)(CH$_2$)$_m$heteroaryl, CH(OH)(CH$_2$)$_m$ substituted heteroaryl, (CO$_2$)$_q$(CH$_2$)$_m$aryl, (CO$_2$)$_q$(CH$_2$)$_m$substituted aryl, (CO$_2$)$_q$(CH$_2$)$_m$ heteroaryl, (CO$_2$)$_q$(CH$_2$)$_m$substituted heteroaryl, (CO$_2$)$_q$(CH$_2$)$_m$ carbocycle, (CO$_2$)$_q$(CH$_2$)$_m$heterocycle, (CO$_2$)$_q$(CH$_2$)$_m$ NR$_3$R$_4$, (CH$_2$)$_m$C(O)R$_3$, (CH$_2$)$_m$C(O)OR$_3$, (CH$_2$)$_m$C(O)NR$_3$R$_4$, (CH$_2$)$_m$C(S)NR$_3$R$_4$, or (CH$_2$)$_m$C(NH)NR$_3$R$_4$;

m is an integer of from 0 to 6;

q is an integer of 0 or 1;

$R_3$ and $R_4$ independently are hydrogen, $C_1$–$C_6$ alkyl, (CH$_2$)$_m$aryl, or (CH$_2$)$_m$heteroaryl, or $R_3$ and $R_4$ are taken together with the nitrogen atom to which they are attached to complete a 3- to 7-membered ring having carbon atoms, the nitrogen atom bearing R$_3$ and R$_4$, and 0 or 1 heteroatoms selected from N(H), N(CH$_3$), O, and S;

Y is O or S;

R$_5$, R$_6$, and R$_7$ independently are hydrogen, halo, hydroxy, C$_1$–C$_6$ alkyl, C$_2$–C$_6$ alkenyl, C$_2$–C$_6$ alkynyl, C$_1$–C$_6$ alkoxy, NO$_2$, CN, CF$_3$, or NR$_9$R$_{10}$, wherein R$_9$ and R$_{10}$ independently are hydrogen, C$_1$–C$_6$ alkyl, C$_3$–C$_7$ cycloalkyl, phenyl, or benzyl, or R$_9$ and R$_{10}$ are taken together with the nitrogen atom to which they are attached to complete a 3- to 7-membered ring having carbon atoms, the nitrogen atom bearing R$_9$ and R$_{10}$, and 0 or 1 heteroatoms selected from N(H), N(CH$_3$), O, and S;

R$_8$ is hydrogen, C$_1$–C$_6$ alkyl, C$_2$–C$_6$ alkenyl, C$_2$–C$_6$ alkynyl, C$_1$–C$_6$ alkoxy, C$_1$–C$_6$ alkanoyl, CH$_2$CO$_2$H, NH$_2$, or OH; and

- - - is a bond or is absent.

Preferred is a compound of Formula V, or a pharmaceutically acceptable salt thereof, or a tautomer thereof, wherein:

Y is O;

G$_1$ and G$_2$ independently are
(CH$_2$)$_m$aryl, wherein m is 1 and aryl is phenyl,
(CH$_2$)$_m$substituted aryl, wherein m is 1 and substituted aryl is 4-methoxyphenyl, 3-methoxyphenyl, 4-fluorophenyl, 3-fluorophenyl, 4-chlorophenyl, 3-chlorophenyl, 4-bromophenyl, 3-bromophenyl, 4-nitrophenyl, 3-nitrophenyl, 4-methylsulfanylphenyl, 3-methylsulfanylphenyl, 4-methylphenyl, 3-methylphenyl, 4-cyanophenyl, 3-cyanophenyl, 4-carboxyphenyl, 3-carboxyphenyl, 4-methanesulfonylphenyl, 3-methanesulfonylphenyl, 4-methoxycarbonyphenyl, or 3-methoxycarbonylphenyl,
(CH$_2$)$_m$heteroaryl, wherein m is 1 and heteroaryl is pyridin-4-yl, pyridin-3-yl, or pyridin-2-yl, or
(CH$_2$)$_m$substituted heteroaryl, wherein m is 1 and substituted heteroaryl is 2-methoxypyridin-4-yl;

R$_5$, R$_6$, and R$_7$ are hydrogen; and

R$_8$ is methyl.

More preferred is a compound of Formula V, or a pharmaceutically acceptable salt thereof, or a tautomer thereof, selected from:

1-Methyl-6-(4-methoxy-phenyl)-prop-1-ynyl)-3-(4-carboxybenzyl)-1H-quinolin-4-one;

3-(4-Methanesulfonyl-benzyl)-1-methyl-6-(4-methoxy-phenyl)-prop-1-ynyl)-1H-quinolin-4-one;

1-Methyl-6-(3-methoxy-phenyl)-prop-1-ynyl)-3-(4-carboxybenzyl)-1H-quinolin-4-one;

3-(4-Methanesulfonyl-benzyl)-1-methyl-6-(3-methoxy-phenyl)-prop-1-ynyl)-1H-quinolin-4-one;

6-(4-Cyano-phenyl)-prop-1-ynyl)-1-methyl-3-(4-carboxybenzyl)-1H-quinolin-4-one;

3-(4-Methanesulfonyl-benzyl)-6-(4-cyano-phenyl)-prop-1-ynyl)-1-methyl-1H-quinolin-4-one;

6-(3-Cyano-phenyl)-prop-1-ynyl)-3-(4-carboxybenzyl)-1-methyl-1H-quinolin-4-one;

4-(4-Methanesulfonyl-benzyl)-6-(3-cyano-phenyl)-prop-1-ynyl)-1-methyl-1H-quinolin-4-one;

6-(4-Fluoro-phenyl)-prop-1-ynyl)-3-(4-carboxybenzyl)-1-methyl-1H-quinolin-4-one;

3-(4-Methanesulfonyl-benzyl)-6-(4-fluoro-phenyl)-prop-1-ynyl)-1-methyl-1H-quinolin-4-one;

6-(3-Fluoro-phenyl)-prop-1-ynyl)-3-(4-carboxybenzyl)-1-methyl-1H-quinolin-4-one;

3-(4-Methanesulfonyl-benzyl)-6-(3-fluoro-phenyl)-prop-1-ynyl)-1-methyl-1H-quinolin-4-one;

6-(4-Chloro-phenyl)-prop-1-ynyl)-3-(4-carboxybenzyl)-1-methyl-1H-quinolin-4-one;

3-(4-Methanesulfonyl-benzyl)-6-(4-chloro-phenyl)-prop-1-ynyl)-1-methyl-1H-quinolin-4-one;

6-(3-Chloro-phenyl)-prop-1-ynyl)-3-(4-carboxybenzyl)-1-methyl-1H-quinolin-4-one;

3-(4-Methanesulfonyl-benzyl)-6-(3-chloro-phenyl)-prop-1-ynyl)-1-methyl-1H-quinolin-4-one;

6-(4-Bromo-phenyl)-prop-1-ynyl)-3-(4-carboxybenzyl)-1-methyl-1H-quinolin-4-one;

3-(4-Methanesulfonyl-benzyl)-6-(4-bromo-phenyl)-prop-1-ynyl)-1-methyl-1H-quinolin-4-one;

6-(3-Bromo-phenyl)-prop-1-ynyl)-3-(4-carboxybenzyl)-1-methyl-1H-quinolin-4-one;

3-(4-Methanesulfonyl-benzyl)-6-(3-bromo-phenyl)-prop-1-ynyl)-1-methyl- 1H-quinolin-4-one;

6-(4-Methanesulfanyl-phenyl)-prop-1-ynyl)-3-(4-carboxybenzyl)-1-methyl-1H-quinolin-4-one;

3-(4-Methanesulfonyl-benzyl)-6-(4-methanesulfanyl-phenyl)-prop-1-ynyl)-1-methyl-1H-quinolin-4-one;

6-(3-Methanesulfanyl-phenyl)-prop-1-ynyl)-3-(4-carboxybenzyl)-1-methyl-1H-quinolin-4-one;

3-(4-Methanesulfonyl-benzyl)-6-(3-methanesulfanyl-phenyl)-prop-1-ynyl)-1-methyl-1H-quinolin-4-one;

6-(4-Methyl-phenyl)-prop-1-ynyl)-3-(4-carboxybenzyl)-1-methyl-1H-quinolin-4-one;

3-(4-Methanesulfonyl-benzyl)-6-(4-methyl-phenyl)-prop-1-ynyl)-1-methyl-1H-quinolin-4-one;

6-(3-Methyl-phenyl)-prop-1-ynyl)-3-(4-carboxybenzyl)-1-methyl-1H-quinolin-4-one;

3-(4-Methanesulfonyl-benzyl)-6-(3-methyl-phenyl)-prop-1-ynyl)-1-methyl-1H-quinolin-4-one;

6-(3-Pyridin-4-yl-prop-1-ynyl)-3-(4-carboxybenzyl)-1-methyl-1H-quinolin-4-one;

3-(4-Methanesulfonyl-benzyl)-6-(3-pyridin-4-yl-prop-1-ynyl)-1-methyl-1H-quinolin-4-one;

6-(3-Pyridin-3-yl-prop-1-ynyl)-3-(4-carboxybenzyl)-1-methyl-1H-quinolin-4-one;

3-(4-Methanesulfonyl-benzyl)-6-(3-pyridin-3-yl-prop-1-ynyl)-1-methyl-1H-quinolin-4-one;

6-[3-(2-Methoxy-pyridin-4-yl)-prop-1-ynyl]-3-(4-carboxybenzyl)-1-methyl-1H-quinolin-4-one;

3-(4-Methanesulfonyl-benzyl)-6-[3-(2-methoxy-pyridin-4-yl)-prop-1-ynyl]-1-methyl-1H-quinolin-4-one;

1-Methyl-6-(4-methoxy-phenyl)-prop-1-ynyl)-3-(4-carboxybenzyl)-2,3-dihydro-1H-quinolin-4-one;

3-(4-Methanesulfonyl-benzyl)-1-methyl-6-(4-methoxy-phenyl)-prop-1-ynyl)-2,3-dihydro-1H-quinolin-4-one;

1-Methyl-6-(3-methoxy-phenyl)-prop-1-ynyl)-3-(4-carboxybenzyl)-2,3-dihydro-1H-quinolin-4-one;

3-(4-Methanesulfonyl-benzyl)-1-methyl-6-(3-methoxy-phenyl)-prop-1-ynyl)-2,3-dihydro-1H-quinolin-4-one;

6-(4-Cyano-phenyl)-prop-1-ynyl)-1-methyl-3-(4-carboxybenzyl)-2,3-dihydro-1H-quinolin-4-one;

3-(4-Methanesulfonyl-benzyl)-6-(4-cyano-phenyl)-prop-1-ynyl)-1-methyl-2,3-dihydro-1H-quinolin-4-one;

6-(3-Cyano-phenyl)-prop-1-ynyl)-3-(4-carboxybenzyl)-1-methyl-2,3-dihydro-1H-quinolin-4-one;

4-(4-Methanesulfonyl-benzyl)-6-(3-cyano-phenyl)-prop-1-ynyl)-1-methyl-2,3-dihydro-1H-quinolin-4-one;

6-(4-Fluoro-phenyl)-prop-1-ynyl)-3-(4-carboxybenzyl)-1-methyl-2,3-dihydro-1H-quinolin-4-one;

3-(4-Methanesulfonyl-benzyl)-6-(4-fluoro-phenyl)-prop-1-ynyl)-1-methyl-2,3-dihydro-1H-quinolin-4-one;

6-(3-Fluoro-phenyl)-prop-1-ynyl)-3-(4-carboxybenzyl)-1-methyl-2,3-dihydro-1H-quinolin-4-one;

3-(4-Methanesulfonyl-benzyl)-6-(3-fluoro-phenyl)-prop-1-ynyl)-1-methyl-2,3-dihydro-1H-quinolin-4-one;

6-(4-Chloro-phenyl)-prop-1-ynyl)-3-(4-carboxybenzyl)-1-methyl-2,3-dihydro-1H-quinolin-4-one;

3-(4-Methanesulfonyl-benzyl)-6-(4-chloro-phenyl)-prop-1-ynyl)-1-methyl-2,3-dihydro-1H-quinolin-4-one;

6-(3-Chloro-phenyl)-prop-1-ynyl)-3-(4-carboxybenzyl)-1-methyl-2,3-dihydro-1H-quinolin-4-one;

3-(4-Methanesulfonyl-benzyl)-6-(3-chloro-phenyl)-prop-1-ynyl)-1-methyl-2,3-dihydro-1H-quinolin-4-one;

6-(4-Bromo-phenyl)-prop-1-ynyl)-3-(4-carboxybenzyl)-1-methyl-2,3-dihydro-1H-quinolin-4-one;

3-(4-Methanesulfonyl-benzyl)-6-(4-bromo-phenyl)-prop-1-ynyl)-1-methyl-2,3-dihydro-1H-quinolin-4-one;

6-(3-Bromo-phenyl)-prop-1-ynyl)-3-(4-carboxybenzyl)-1-methyl-2,3-dihydro-1H-quinolin-4-one;

3-(4-Methanesulfonyl-benzyl)-6-(3-bromo-phenyl)-prop-1-ynyl)-1-methyl-2,3-dihydro-1H-quinolin-4-one;

6-(4-Methanesulfanyl-phenyl)-prop-1-ynyl)-3-(4-carboxybenzyl)-1-methyl-2,3-dihydro-1H-quinolin-4-one;

3-(4-Methanesulfonyl-benzyl)-6-(4-methanesulfanyl-phenyl)-prop-1-ynyl)-1-methyl-2,3-dihydro-1H-quinolin-4-one;

6-(3-Methanesulfanyl-phenyl)-prop-1-ynyl)-3-(4-carboxybenzyl)-1-methyl-2,3-dihydro-1H-quinolin-4-one;

3-(4-Methanesulfonyl-benzyl)-6-(3-methanesulfanyl-phenyl)-prop-1-ynyl)-1-methyl-2,3-dihydro-1H-quinolin-4-one;

6-(4-Methyl-phenyl)-prop-1-ynyl)-3-(4-carboxybenzyl)-1-methyl-2,3-dihydro-1H-quinolin-4-one;

3-(4-Methanesulfonyl-benzyl)-6-(4-methyl-phenyl)-prop-1-ynyl)-1-methyl-2,3-dihydro-1H-quinolin-4-one;

6-(3-Methyl-phenyl)-prop-1-ynyl)-3-(4-carboxybenzyl)-1-methyl-2,3-dihydro-1H-quinolin-4-one;

3-(4-Methanesulfonyl-benzyl)-6-(3-methyl-phenyl)-prop-1-ynyl)-1-methyl-2,3-dihydro-1H-quinolin-4-one;

6-(3-pyridin-4-yl-prop-1-ynyl)-3-(4-carboxybenzyl)-1-methyl-2,3-dihydro-1H-quinolin-4-one;

3-(4-Methanesulfonyl-benzyl)-6-(3-pyridin-4-yl-prop-1-ynyl)-1-methyl-2,3-dihydro-1H-quinolin-4-one;

6-(3-Pyridin-3-yl-prop-1-ynyl)-3-(4-carboxybenzyl)-1-methyl-2,3-dihydro-1H-quinolin-4-one;

3-(4-Methanesulfonyl-benzyl)-6-(3-pyridin-3-yl-prop-1-ynyl)-1-methyl-2,3-dihydro-1H-quinolin-4-one;

6-[3-(2-Methoxy-pyridin-4-yl)-prop-1-ynyl]-3-(4-carboxybenzyl)-1-methyl-2,3-dihydro-1H-quinolin-4-one; and 3-(4-Methanesulfonyl-benzyl)-6-[3-(2-methoxy-pyridin-4-yl)-prop-1-ynyl]-1-methyl-2,3-dihydro-1H-quinolin-4-one.

Another embodiment of the invention is a compound according to Formula I of Formula VI

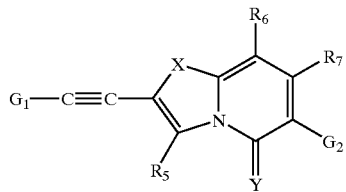

VI or a pharmaceutically acceptable salt thereof, or a tautomer thereof, wherein:

$G_1$ and $G_2$ independently are

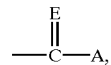

wherein

E is independently O or S;

A is $OR_1$ or $NR_1R_2$;

$R_1$ and $R_2$ independently are hydrogen, $C_1$–$C_6$ alkyl, $C_2$–$C_6$ alkenyl, $C_2$–$C_6$ alkynyl, $(CH_2)_n$aryl, $(CH_2)_n$cycloalkyl, or $(CH_2)_n$heteroaryl, or $R_1$ and $R_2$ are taken together with the nitrogen atom to which they are attached to complete a 3- to 8-membered ring having carbon atoms, the nitrogen atom bearing $R_1$ and $R_2$, and 0 or 1 heteroatom selected from N(H), N(CH$_3$), O, and S, and which ring is optionally unsubstituted or substituted with =O, halo, or methyl, wherein n is an integer of from 0 to 6; or $G_1$ and $G_2$ independently are hydrogen, halo, $C_1$–$C_6$ alkyl, $C_2$–$C_6$ alkenyl, $C_2$–$C_6$ alkynyl, $(CH_2)_m$OH, $(CH_2)_m$OR$_3$, $(CH_2)_m$cycloalkyl, $(CH_2)_m$aryl, $(CH_2)_m$ substituted aryl, $(CH_2)_m$heteroaryl, $(CH_2)_m$substituted heteroaryl, CH(OH)(CH$_2$)$_m$aryl, CHOH(CH$_2$)$_m$ substituted aryl, CH(OH)(CH$_2$)$_m$heteroaryl, CH(OH)(CH$_2$)$_m$ substituted heteroaryl, $(CO_2)_q(CH_2)_m$aryl, $(CO_2)_q(CH_2)_m$substituted aryl, $(CO_2)_q(CH_2)_m$ heteroaryl, $(CO_2)_q(CH_2)_m$substituted heteroaryl, $(CO_2)_q(CH_2)_m$ carbocycle, $(CO_2)_q(CH_2)_m$heterocycle, $(C_2)_q(CH_2)_m$NR$_3$R$_4$, $(CH_2)_m$C(O)R$_3$, $(CH_2)_m$C(O)OR$_3$, $(CH_2)_m$C(O)NR$_3$R$_4$, $(CH_2)_m$C(S)NR$_3$R$_4$, or $(CH_2)_m$C(NH)NR$_3$R$_4$;

m is an integer of from 0 to 6;

q is an integer of 0 or 1;

$R_3$ and $R_4$ independently are hydrogen, $C_1$–$C_6$ alkyl, $(CH_2)_m$aryl, or $(CH_2)_m$heteroaryl, or $R_3$ and $R_4$ are taken together with the nitrogen atom to which they are attached to complete a 3- to 7-membered ring having carbon atoms, the nitrogen atom bearing $R_3$ and $R_4$, and 0 or 1 heteroatoms selected from N(H), N(CH$_3$), O, and S;

Y is O or S:

$R_5$, $R_6$, and $R_7$ independently are hydrogen, halo, hydroxy, $C_1$–$C_6$ alkyl, $C_2$–$C_6$ alkenyl, $C_2$–$C_6$ alkynyl, $C_1$–$C_6$ alkoxy, NO$_2$, CN, CF$_3$, or NR$_9$R$_{10}$, wherein $R_9$ and $R_{10}$ independently are hydrogen, $C_1$–$C_6$ alkyl, $C_3$–$C_7$ cycloalkyl, phenyl, or benzyl, or $R_9$ and $R_{10}$ are taken together with the nitrogen atom to which they are attached to complete a 3- to 7-membered ring having carbon atoms, the nitrogen atom bearing $R_9$ and $R_{10}$, and 0 or 1 heteroatoms selected from N(H), N(CH$_3$), O, and S; and X is S, (SO), S(O)$_2$, O, N(R$_8$), wherein $R_8$ is as defined above, C(O), or CH$_2$.

Preferred is a compound of Formula VI, or a pharmaceutically acceptable salt thereof, or a tautomer thereof, wherein:

Y ix O;
X is S;
G₁ and G₂ independently are
(CH₂)ₘaryl, wherein m is 1 and aryl is phenyl,
(CH₂)ₘsubstituted aryl, wherein m is 1 and substituted aryl is 4-methoxyphenyl, 3-methoxyphenyl, 4-fluorophenyl, 3-fluorophenyl, 4-chlorophenyl, 3-chlorophenyl, 4-bromophenyl, 3-bromophenyl, 3,4-difluorophenyl, 3-fluoro-4-methoxyphenyl, 4-nitrophenyl, 3-nitrophenyl, 4-methylsulfanylphenyl, 3-methylsulfanylphenyl, 4-methylphenyl, 3-methylphenyl, 4-cyanophenyl, 3-cyanophenyl, 4-carboxyphenyl, 3-carboxyphenyl, 4-methanesulfonylphenyl, 3-methanesulfonylphenyl, 4-methoxycarbonyphenyl, or 3-methoxycarbonylphenyl,
(CH₂)ₘheteroaryl, wherein m is 1 and heteroaryl is pyridin-4-yl, pyridin-3-yl, or pyridin-2-yl, or
(CH₂)ₘsubstituted heteroaryl, wherein m is 1 and substituted heteroaryl is 2-methoxypyridin-4-yl; and
R₅, R₆, and R₇ are hydrogen.

More preferred is a compound of Formula VI, or a pharmaceutically acceptable salt thereof, or a tautomer thereof, selected from:

2-(Phenyl)-prop-1-ynyl)-6-benzyl-4H-thiazolo[3,2-a]pyridin-5-one;
2-(4-Methoxy-phenyl)-prop-1-ynyl)-6-(4-carboxybenzyl)-4H-thiazolo[3,2-a]pyridin-5-one;
6-(4-Methanesulfonyl-benzyl)-2-(4-methoxy-phenyl)-prop-1-ynyl)-4H-thiazolo[3,2-a]pyridin-5-one;
2-(3-Methoxy-phenyl)-prop-1-ynyl)-6-(4-carboxybenzyl)-4H-thiazolo[3,2-a]pyridin-5-one;
6-(4-Methanesulfonyl-benzyl)-2-(3-methoxy-phenyl)-prop-1-ynyl)-4H-thiazolo[3,2-a]pyridin-5-one;
2-(4-Cyano-phenyl)-prop-1-ynyl)-6-(4-carboxybenzyl)-4H-thiazolo[3,2-a]pyridin-5-one;
6-(4-Methanesulfonyl-benzyl)-2-(4-cyano-phenyl)-prop-1-ynyl)-4H-thiazolo[3,2-a]pyridin-5-one;
2-(3-Cyano-phenyl)-prop-1-ynyl)-6-(4-carboxybenzyl)-4H-thiazolo[3,2-a]pyridin-5-one;
6-(4-Methanesulfonyl-benzyl)-2-(3-cyano-phenyl)-prop-1-ynyl)-4H-thiazolo[3,2-a]pyridin-5-one;
2-(4-Fluoro-phenyl)-prop-1-ynyl)-6-(4-carboxybenzyl)-4H-thiazolo[3,2-a]pyridin-5-one;
6-(4-Methanesulfonyl-benzyl)-2-(4-fluoro-phenyl)-prop-1-ynyl)-4H-thiazolo[3,2-a]pyridin-5-one;
2-(3-Fluoro-phenyl)-prop-1-ynyl)-6-(4-carboxybenzyl)-4H-thiazolo[3,2-a]pyridin-5-one;
6-(4-Methanesulfonyl-benzyl)-2-(3-fluoro-phenyl)-prop-1-ynyl)-4H-thiazolo[3,2-a]pyridin-5-one;
2-(4-Chloro-phenyl)-prop-1-ynyl)-6-(4-carboxybenzyl)-4H-thiazolo[3,2-a]pyridin-5-one;
6-(4-Methanesulfonyl-benzyl)-2-(4-chloro-phenyl)-prop-1-ynyl)-4H-thiazolo[3,2-a]pyridin-5-one;
2-(3-Chloro-phenyl)-prop-1-ynyl)-6-(4-carboxybenzyl)-4H-thiazolo[3,2-a]pyridin-5-one;
6-(4-Methanesulfonyl-benzyl)-2-(3-chloro-phenyl)-prop-1-ynyl)-4H-thiazolo[3,2-a]pyridin-5-one;
2-(4-Bromo-phenyl)-prop-1-ynyl)-6-(4-carboxybenzyl)-4H-thiazolo[3,2-a]pyridin-5-one;
6-(4-Methanesulfonyl-benzyl)-2-(4-bromo-phenyl)-prop-1-ynyl)-4H-thiazolo[3,2-a]pyridin-5-one;
2-(3-Bromo-phenyl)-prop-1-ynyl)-6-(4-carboxybenzyl)-4H-thiazolo[3,2-a]pyridin-5-one;
6-(4-Methanesulfonyl-benzyl)-2-(3-bromo-phenyl)-prop-1-ynyl)-4H-thiazolo[3,2-a]pyridin-5-one;
2-(4-Methanesulfanyl-phenyl)-prop-1-ynyl)-6-(4-carboxybenzyl)-4H-thiazolo[3,2-a]pyridin-5-one;
6-(4-Methanesulfonyl-benzyl)-2-(4-methanesulfanyl-phenyl)-prop-1-ynyl)-4H-thiazolo[3,2-a]pyridin-5-one;
2-(3-Methanesulfanyl-phenyl)-prop-1-ynyl)-6-(4-carboxybenzyl)-4H-thiazolo[3,2-a]pyridin-5-one;
6-(4-Methanesulfonyl-benzyl)-2-(3-methanesulfanyl-phenyl)-prop-1-ynyl)-4H-thiazolo[3,2-a]pyridin-5-one;
2-(4-Methyl-phenyl)-prop-1-ynyl)-6-(4-carboxybenzyl)-4H-thiazolo[3,2-a]pyridin-5-one;
6-(4-Methanesulfonyl-benzyl)-2-(4-methyl-phenyl)-prop-1-ynyl)-4H-thiazolo[3,2-a]pyridin-S-one;
2-(3-Methyl-phenyl)-prop-1-ynyl)-6-(4-carboxybenzyl)-4H-thiazolo[3,2-a]pyridin-5-one;
6-(4-Methanesulfonyl-benzyl)-2-(3-methyl-phenyl)-prop-1-ynyl)-4H-thiazolo[3,2-a]pyridin-5-one;
2-(3-Pyridin-4-yl-prop-1-ynyl)-6-(4-carboxybenzyl)-4H-thiazolo[3,2-a]pyridin-5-one;
6-(4-Methanesulfonyl-benzyl)-2-(3-pyridin-4-yl-prop-1-ynyl)-4H-thiazolo[3,2-a]pyridin-5-one;
2-(3-Pyridin-3-yl-prop-1-ynyl)-6-(4-carboxybenzyl)-4H-thiazolo[3,2-a]pyridin-5-one;
6-(4-Methanesulfonyl-benzyl)-2-(3-pyridin-3-yl-prop-1-ynyl)-4H-thiazolo[3,2-a]pyridin-5-one;
2-[3-(2-Methoxy-pyridin-4-yl)-prop-1-ynyl]-6-(4-carboxybenzyl)-4H-thiazolo[3,2-a]pyridin-5-one; and
6-(4-Methanesulfonyl-benzyl)-2-[3-(2-methoxy-pyridin-4-yl)-prop-1-ynyl]-4H-thiazolo[3,2-a]pyridin-5-one.

Another embodiment of the invention is a compound according to claim 1 of Formula VII

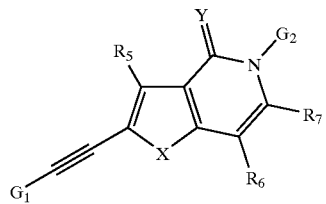

or a pharmaceutically acceptable salt thereof, or a tautomer thereof, wherein:
G₁ and G₂ independently are

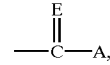

wherein
E is independently O or S;
A is OR₁ or NR₁R₂;
R₁ and R₂ independently are hydrogen, C₁–C₆ alkyl, C₂–C₆ alkenyl, C₂–C₆ alkynyl, (CH₂)ₙaryl, (CH₂)ₙ cycloalkyl, or (CH₂)ₙheteroaryl, or R₁ and R₂ are taken together with the nitrogen atom to which they are attached to complete a 3- to 8-membered ring having carbon atoms, the nitrogen atom bearing R₁ and $R_2$, and 0 or 1 heteroatom selected from N(H), N(CH$_3$), O, and S, and which ring is optionally unsubstituted or substituted with =O, halo, or methyl, wherein n is an integer of from 0 to 6; or $G_1$ and $G_2$ independently are hydrogen, halo, $C_1$–$C_6$ alkyl, $C_2$–$C_6$ alkenyl, $C_2$–$C_6$ alkynyl, $(CH_2)_m$OH, $(CH_2)_m$OR$_3$, $(CH_2)_m$cycloalkyl, $(CH_2)_m$aryl, $(CH_2)_m$ substituted aryl, $(CH_2)_m$heteroaryl, $(CH_2)_m$substituted heteroaryl, CH(OH)(CH$_2$)$_m$aryl, CHOH(CH$_2$)$_m$ substituted aryl, CH(OH)(CH$_2$)$_m$heteroaryl, CH(OH)(CH$_2$)$_m$ substituted heteroaryl, $(CO_2)_q$(CH$_2$)$_m$aryl, $(CO_2)_q$ (CH$_2$)$_m$substituted aryl, $(CO_2)_q$(CH$_2$)$_m$ heteroaryl, $(CO_2)_q$(CH$_2$)$_m$substituted heteroaryl, $(CO_2)_q$(CH$_2$)$_m$ carbocycle, $(CO_2)_q$(CH$_2$)$_m$heterocycle, $(CO_2)_q$(CH$_2$)$_m$ NR$_3$R$_4$, (CH$_2$)$_m$C(O)R$_3$, (CH$_2$)$_m$C(O)OR$_3$, (CH$_2$)$_m$C(O)NR$_3$R$_4$, (CH$_2$)$_m$C(S)NR$_3$R$_4$, or (CH$_2$)$_m$C(NH)NR$_3$R$_4$;

m is an integer of from 0 to 6;

q is an integer of 0 or 1;

$R_3$ and $R_4$ independently are hydrogen, $C_1$–$C_6$ alkyl, (CH$_2$)$_m$aryl, or (CH$_2$)$_m$heteroaryl, or $R_3$ and $R_4$ are taken together with the nitrogen atom to which they are attached to complete a 3- to 7-membered ring having carbon atoms, the nitrogen atom bearing $R_3$ and $R_4$, and 0 or 1 heteroatoms selected from N(H), N(CH$_3$), O, and S;

Y is O or S:

$R_5$, $R_6$, and $R_7$ independently are hydrogen, halo, hydroxy, $C_1$–$C_6$ alkyl, $C_2$–$C_6$ alkenyl, $C_2$–$C_6$ alkynyl, $C_1$–$C_6$ alkoxy, NO$_2$, CN, CF$_3$, or NR$_9$R$_{10}$, wherein $R_9$ and $R_{10}$ independently are hydrogen, $C_1$–$C_6$ alkyl, $C_3$–$C_7$ cycloalkyl, phenyl, or benzyl, or $R_9$ and $R_{10}$ are taken together with the nitrogen atom to which they are attached to complete a 3- to 7-membered ring having carbon atoms, the nitrogen atom bearing $R_9$ and $R_{10}$, and 0 or 1 heteroatoms selected from N(H), N(CH$_3$), O, and S; and X is S, (SO), S(O)$_2$, O, N(R$_8$), wherein $R_8$ is as defined above, C(O), or CH$_2$.

Preferred is a compound of Formula VII, or a pharmaceutically acceptable salt thereof, or a tautomer thereof, wherein:

Y ix O;

X is S;

$G_1$ and $G_2$ independently are
(CH$_2$)$_m$aryl, wherein m is 1 and aryl is phenyl,
(CH$_2$)$_m$substituted aryl, wherein m is 1 and substituted aryl is 4-methoxyphenyl, 3-methoxyphenyl, 4-fluorophenyl, 3-fluorophenyl, 4-chlorophenyl, 3-chlorophenyl, 4-bromophenyl, 3-bromophenyl, 3,4-difluorophenyl, 3-fluoro-4-methoxyphenyl, 4-nitrophenyl, 3-nitrophenyl, 4-methylsulfanylphenyl, 3-methylsulfanylphenyl, 4-methylphenyl, 3-methylphenyl, 4-cyanophenyl, 3-cyanophenyl, 4-carboxyphenyl, 3-carboxyphenyl, 4-methanesulfonylphenyl, 3-methanesulfonylphenyl, 4-methoxycarbonyphenyl, or 3-methoxycarbonylphenyl,
(CH$_2$)$_m$heteroaryl, wherein m is 1 and heteroaryl is pyridin-4-yl, pyridin-3-yl, or pyridin-2-yl, or
(CH$_2$)$_m$substituted heteroaryl, wherein m is 1 and substituted heteroaryl is 2-methoxypyridin-4-yl; and
$R_5$, $R_6$, and $R_7$ are hydrogen.

More preferred is a compound of Formula VII, or a pharmaceutically acceptable salt thereof, or a tautomer thereof, selected from:

2-(Phenyl-prop-1-ynyl)-5-(4-benzyl)-5H-thieno[3,2-c] pyridin-4-one;

2-(4-Methoxy-phenyl)-prop-1-ynyl)-5-(4-carboxybenzyl)-5H-thieno[3,2-c]pyridin-4-one;

5-(4-Methanesulfonyl-benzyl)-2-(4-methoxy-phenyl)-prop-1-ynyl)-5H-thieno[3,2-c]pyridin-4-one;

2-(3-Methoxy-phenyl)-prop-1-ynyl)-5-(4-carboxybenzyl)-5H-thieno[3,2-c]pyridin-4-one;

5-(4-Methanesulfonyl-benzyl)-2-(3-methoxy-phenyl)-prop-1-ynyl)-5H-thieno[3,2-c]pyridin-4-one;

2-(4-Cyano-phenyl)-prop-1-ynyl)-5-(4-carboxybenzyl)-5H-thieno[3,2-c]pyridin-4-one;

5-(4-Methanesulfonyl-benzyl)-2-(4-cyano-phenyl)-prop-1-ynyl)-5H-thieno[3,2-c]pyridin-4-one;

2-(3-Cyano-phenyl)-prop-1-ynyl)-5-(4-carboxybenzyl)-5H-thieno[3,2-c]pyridin-4-one;

5-(4-Methanesulfonyl-benzyl)-2-(3-cyano-phenyl)-prop-1-ynyl)-5H-thieno[3,2-c]pyridin-4-one;

2-(4-Fluoro-phenyl)-prop-1-ynyl)-5-(4-carboxybenzyl)-5H-thieno[3,2-c]pyridin-4-one;

5-(4-Methanesulfonyl-benzyl)-2-(4-fluoro-phenyl)-prop-1-ynyl)-5H-thieno[3,2-c]pyridin-4-one;

2-(3-Fluoro-phenyl)-prop-1-ynyl)-5-(4-carboxybenzyl)-5H-thieno[3,2-c]pyridin-4-one;

5-(4-Methanesulfonyl-benzyl)-2-(3-fluoro-phenyl)-prop-1-ynyl)-5H-thieno[3,2-c]pyridin-4-one;

2-(4-Chloro-phenyl)-prop-1-ynyl)-5-(4-carboxybenzyl) 5H-thieno[3,2-c]pyridin-4-one;

5-(4-Methanesulfonyl-benzyl)-2-(4-chloro-phenyl)-prop-1-ynyl)-5H-thieno[3,2-c]pyridin-4-one;

2-(3-Chloro-phenyl)-prop-1-ynyl)-5-(4-carboxybenzyl)-5H-thieno[3,2-c]pyridin-4-one;

5-(4-Methanesulfonyl-benzyl)-2-(3-chloro-phenyl)-prop-1-ynyl)-5H-thieno[3,2-c]pyridin-4-one;

2-(4-Bromo-phenyl)-prop-1-ynyl)-5-(4-carboxybenzyl)-5H-thieno[3,2-c]pyridin-4-one;

5-(4-Methanesulfonyl-benzyl)-2-(4-bromo-phenyl)-prop-1-ynyl)-5H-thieno[3,2-c]pyridin-4-one;

2-(3-Bromo-phenyl)-prop-1-ynyl)-5-(4-carboxybenzyl)-5H-thieno[3,2-c]pyridin-4-one;

5-(4-Methanesulfonyl-benzyl)-2-(3-bromo-phenyl)-prop-1-ynyl)-5H-thieno[3,2-c]pyridin-4-one;

2-(4-Methanesulfanyl-phenyl)-prop-1-ynyl)-5-(4-carboxybenzyl)-5H-thieno[3,2-c]pyridin-4-one;

5-(4-Methanesulfonyl-benzyl)-2-(4-methanesulfanyl-phenyl)-prop-1-ynyl)-5H-thieno[3,2-c]pyridin-4-one;

2-(3-Methanesulfanyl-phenyl)-prop-1-ynyl)-5-(4-carboxybenzyl)-5H-thieno[3,2-c]pyridin-4-one;

5-(4-Methanesulfonyl-benzyl)-2-(3-methanesulfanyl-phenyl)-prop-1-ynyl)-5H-thieno[3,2-c]pyridin-4-one;

2-(4-Methyl-phenyl)-prop-1-ynyl)-5-(4-carboxybenzyl)-5H-thieno[3,2-c]pyridin-4-one;

5-(4-Methanesulfonyl-benzyl)-2-(4-methyl-phenyl)-prop-1-ynyl)-5H-thieno[3,2-c]pyridin-4-one;

2-(3-Methyl-phenyl)-prop-1-ynyl)-5-(4-carboxybenzyl)-5H-thieno[3,2-c]pyridin-4-one;

5-(4-Methanesulfonyl-benzyl)-2-(3-methyl-phenyl)-prop-1-ynyl)-5H-thieno[3,2-c]pyridin-4-one;

2-(3-Pyridin-4-yl-prop-1-ynyl)-5-(4-carboxybenzyl)-5H-thieno[3,2-c]pyridin-4-one;

5-(4-Methanesulfonyl-benzyl)-2-(3-pyridin-4-yl-prop-1-ynyl)-5H-thieno[3,2-c]pyridin-4-one;

2-(3-Pyridin-3-yl-prop-1-ynyl)-5-(4-carboxybenzyl)-5H-thieno[3,2-c]pyridin-4-one;

5-(4-Methanesulfonyl-benzyl)-2-(3-pyridin-3-yl-prop-1-ynyl)-5H-thieno[3,2-c]pyridin-4-one;

2-[3-(2-Methoxy-pyridin-4-yl)-prop-1-ynyl]-5-(4-carboxybenzyl)-5H-thieno[3,2-c]pyridin-4-one;

5-(4-Methanesulfonyl-benzyl)-2-[3-(2-methoxy-pyridin-4-yl)-prop-1-ynyl]-5H-thieno[3,2-c]pyridin-4-one;

2-(Phenyl-prop-1-ynyl)-5-(4-benzyl)-7-methyl-5H-thieno[3,2-c]pyridin-4-one;

2-(4-Methoxy-phenyl)-prop-1-ynyl)-5-(4-carboxybenzyl)-7-methyl-5H-thieno[3,2-c]pyridin-4-one;

5-(4-Methanesulfonyl-benzyl)-2-(4-methoxy-phenyl)-prop-1-ynyl)-7-methyl-5H-thieno[3,2-c]pyridin-4-one;

2-(3-Methoxy-phenyl)-prop-1-ynyl)-5-(4-carboxybenzyl)-7-methyl-5H-thieno[3,2-c]pyridin-4-one;

5-(4-Methanesulfonyl-benzyl)-2-(3-methoxy-phenyl)-prop-1-ynyl)-7-methyl-5H-thieno[3,2-c]pyridin-4-one;

2-(4-Cyano-phenyl)-prop-1-ynyl)-5-(4-carboxybenzyl)-7-methyl-5H-thieno[3,2-c]pyridin-4-one;

5-(4-Methanesulfonyl-benzyl)-2-(4-cyano-phenyl)-prop-1-ynyl)-7-methyl-5H-thieno[3,2-c]pyridin-4-one;

2-(3-Cyano-phenyl)-prop-1-ynyl)-5-(4-carboxybenzyl)-7-methyl-5H-thieno[3,2-c]pyridin-4-one;

5-(4-Methanesulfonyl-benzyl)-2-(3-cyano-phenyl)-prop-1-ynyl)-7-methyl-5H-thieno[3,2-c]pyridin-4-one;

2-(4-Fluoro-phenyl)-prop-1-ynyl)-5-(4-carboxybenzyl)-7-methyl-5H-thieno[3,2-c]pyridin-4-one;

5-(4-Methanesulfonyl-benzyl)-2-(4-fluoro-phenyl)-prop-1-ynyl)-7-methyl-5H-thieno[3,2-c]pyridin-4-one;

2-(3-Fluoro-phenyl)-prop-1-ynyl)-5-(4-carboxybenzyl)-7-methyl-5H-thieno[3,2-c]pyridin-4-one;

5-(4-Methanesulfonyl-benzyl)-2-(3-fluoro-phenyl)-prop-1-ynyl)-7-methyl-5H-thieno[3,2-c]pyridin-4-one;

2-(4-Chloro-phenyl)-prop-1-ynyl)-5-(4-carboxybenzyl)-7-methyl-5H-thieno[3,2-c]pyridin-4-one;

5-(4-Methanesulfonyl-benzyl)-2-(4-chloro-phenyl)-prop-1-ynyl)-7-methyl-5H-thieno[3,2-c]pyridin-4-one;

2-(3-Chloro-phenyl)-prop-1-ynyl)-5-(4-carboxybenzyl)-7-methyl-5H-thieno[3,2-c]pyridin-4-one;

5-(4-Methanesulfonyl-benzyl)-2-(3-chloro-phenyl)-prop-1-ynyl)-7-methyl-5H-thieno[3,2-c]pyridin-4-one;

2-(4-Bromo-phenyl)-prop-1-ynyl)-5-(4-carboxybenzyl)-7-methyl-5H-thieno[3,2-c]pyridin-4-one;

5-(4-Methanesulfonyl-benzyl)-2-(4-bromo-phenyl)-prop-1-ynyl)-7-methyl-5H-thieno[3,2-c]pyridin-4-one;

2-(3-Bromo-phenyl)-prop-1-ynyl)-5-(4-carboxybenzyl)-7-methyl-5H-thieno[3,2-c]pyridin-4-one;

5-(4-Methanesulfonyl-benzyl)-2-(3-bromo-phenyl)-prop-1-ynyl)-7-methyl-5H-thieno[3,2-c]pyridin-4-one;

2-(4-Methanesulfanyl-phenyl)-prop-1-ynyl)-7-methyl-5-(4-carboxybenzyl)-5H-thieno[3,2-c]pyridin-4-one;

5-(4-Methanesulfonyl-benzyl)-2-(4-methanesulfanyl-phenyl)-prop-1-ynyl)-7-methyl-5H-thieno[3,2-c]pyridin-4-one;

2-(3-Methanesulfanyl-phenyl)-prop-1-ynyl)-5-(4-carboxybenzyl)-7-methyl-5H-thieno[3,2-c]pyridin-4-one;

5-(4-Methanesulfonyl-benzyl)-2-(3-methanesulfanyl-phenyl)-prop-1-ynyl)-7-methyl-5H-thieno[3,2-c]pyridin-4-one;

2-(4-Methyl-phenyl)-prop-1-ynyl)-5-(4-carboxybenzyl)-7-methyl-5H-thieno[3,2-c]pyridin-4-one;

5-(4-Methanesulfonyl-benzyl)-2-(4-methyl-phenyl)-prop-1-ynyl)-7-methyl-5H-thieno[3,2-c]pyridin-4-one;

2-(3-Methyl-phenyl)-prop-1-ynyl)-5-(4-carboxybenzyl)-7-methyl-5H-thieno[3,2-c]pyridin-4-one;

5-(4-Methanesulfonyl-benzyl)-2-(3-methyl-phenyl)-prop-1-ynyl)-7-methyl-5H-thieno[3,2-c]pyridin-4-one;

2-(3-Pyridin-4-yl-prop-1-ynyl)-5-(4-carboxybenzyl)-7-methyl-5H-thieno[3,2-c]pyridin-4-one;

5-(4-Methanesulfonyl-benzyl)-2-(3-pyridin-4-yl-prop-1-ynyl)-7-methyl-5H-thieno[3,2-c]pyridin-4-one;

2-(3-Pyridin-3-yl-prop-1-ynyl)-5-(4-carboxybenzyl)-7-methyl-5H-thieno[3,2-c]pyridin-4-one;

5-(4-Methanesulfonyl-benzyl)-2-(3-pyridin-3-yl-prop-1-ynyl)-7-methyl-5H-thieno[3,2-c]pyridin-4-one;

2-[3-(2-Methoxy-pyridin-4-yl)-prop-1-ynyl]-5-(4-carboxybenzyl)-7-methyl-5H-thieno[3,2-c]pyridin-4-one; and 5-(4-Methanesulfonyl-benzyl)-2-[3-(2-methoxy-pyridin-4-yl)-prop-1-ynyl]-7-methyl-5H-thieno[3,2-c]pyridin-4-one.

Also preferred is a compound of Formula I, or a pharmaceutically acceptable salt thereof, wherein $G_1$ and $G_2$ are as defined above and B is

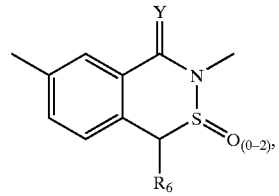

wherein Y and $R_6$ are as defined above for Formula I.

More preferred is a compound of Formula I, or a pharmaceutically acceptable salt thereof, selected from:

4-[2,4-dioxo-6-(3-phenyl-prop-1-ynyl)-1,4-dihydro-2H-2l$^4$-benzo[d][1,2]thiazin-3-ylmethyl]-benzoic acid; and 4-[2,2,4-trioxo-6-(3-phenyl-prop-1-ynyl)-1,4-dihydro-2H-2l$^6$-benzo[d][1,2]thiazin-3-ylmethyl]-benzoic acid.

Also preferred is a compound of Formula I, or a pharmaceutically acceptable salt thereof, wherein $G_1$ and $G_2$ are as defined above and B is

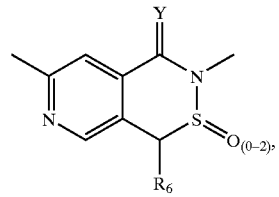

wherein Y and $R_6$ are as defined above for Formula I.

More preferred is a compound of Formula I, or a pharmaceutically acceptable salt thereof, selected from:

4-[1,3-dioxo-7-(3-phenyl-prop-1-ynyl)-3,4-dihydro-1H-3l$^4$-thia-2,6-diaza-naphthalen-2-ylmethyl]-benzoic acid; and 4-[1,3,3-trioxo-7-(3-phenyl-prop-1-ynyl)-3,4-dihydro-1H-3l$^6$-thia-2,6-diaza-naphthalen-2-ylmethyl]-benzoic acid.

Also preferred is a compound of Formula I, or a pharmaceutically acceptable salt thereof, wherein $G_1$ and $G_2$ are as defined above and B is

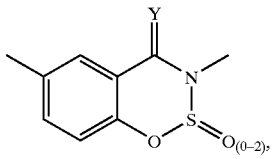

wherein Y is as defined above for Formula I.

More preferred is a compound of Formula I, or a pharmaceutically acceptable salt thereof, selected from:

4-[2,4-dioxo-6-(3-phenyl-prop-1-ynyl)-4H-$2l^4$-benzo[e][1,2,3]oxathiazin-3-ylmethyl]-benzoic acid; and 4-[2,2,4-trioxo-6-(3-phenyl-prop-1-ynyl)-4H-$2l^6$-benzo[e][1,2,3]oxathiazin-3-ylmethyl]-benzoic acid.

Also preferred is a compound of Formula I, or a pharmaceutically acceptable salt thereof, wherein $G_1$ and $G_2$ are as defined above and B is

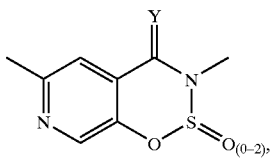

wherein Y is as defined above for Formula I.

More preferred is a compound of Formula I, or a pharmaceutically acceptable salt thereof, selected from:

4-[2,4-dioxo-6-(3-phenyl-prop-1-ynyl)-4H-1-oxa-$2l^4$-thia-3,7-diaza-naphthalen-3-ylmethyl]-benzoic acid; and 4-[2,2,4-trioxo-6-(3-phenyl-prop-1-ynyl)-4H-1-oxa-$2l^6$-thia-3,7-diaza-naphthalen-3-ylmethyl]-benzoic acid.

Also preferred is a compound of Formula I, or a pharmaceutically acceptable salt thereof, wherein $G_1$ and $G_2$ are as defined above and B is

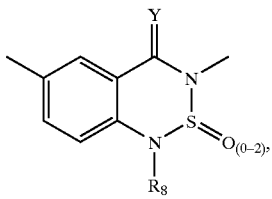

wherein Y and $R_8$ are as defined above for Formula I.

More preferred is a compound of Formula I, or a pharmaceutically acceptable salt thereof, selected from:

4-[1-methyl-2,4-dioxo-6-(3-phenyl-prop-1-ynyl)-1,4-dihydro-2H-$2l^4$-benzo[1,2,6]thiadiazin-3-ylmethyl]-benzoic acid;

4-[2,4-dioxo-6-(3-phenyl-prop-1-ynyl)-1,4-dihydro-2H-$2l^4$-benzo[1,2,6]thiadiazin-3-ylmethyl]-benzoic acid; and 4-[1-methyl-2,2,4-trioxo-6-(3-phenyl-prop-1-ynyl)-1,4-dihydro-2H-$2l^6$-benzo[1,2,6]thiadiazin-3-ylmethyl]-benzoic acid.

Also preferred is a compound of Formula I, or a pharmaceutically acceptable salt thereof, wherein $G_1$ and $G_2$ are as defined above and B is

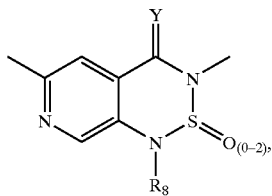

wherein Y and $R_8$ are as defined above for Formula I.

More preferred is a compound of Formula I, or a pharmaceutically acceptable salt thereof, selected from:

3-[1-methyl-2,4-dioxo-6-(3-phenyl-prop-1-ynyl)-1,4-dihydro-2H-$2l^4$-pyrido[3,4-c][1,2,6]thiadiazin-3-ylmethyl]-benzoic acid;

3-[2,4-dioxo-6-(3-phenyl-prop-1-ynyl)-1,4-dihydro-2H-$2l^4$-pyrido[3,4-c][1,2,6]thiadiazin-3-ylmethyl]-benzoic acid; and 3-[1-methyl-2,2,4-trioxo-6-(3-phenyl-prop-1-ynyl)-1,4-dihydro-2H-$2l^6$-pyrido[3,4-c][1,2,6]thiadiazin-3-ylmethyl]-benzoic acid.

Also preferred is a compound of Formula I, or a pharmaceutically acceptable salt thereof, wherein $G_1$ and $G_2$ are as defined above and B is

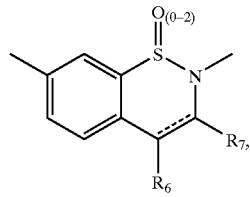

wherein - - -, $R_6$ and $R_7$ are as defined above for Formula I.

More preferred is a compound of Formula I, or a pharmaceutically acceptable salt thereof, selected from:

4-[1-oxo-7-(3-phenyl-prop-1-ynyl)-1H-$1l^4$-benzo[e][1,2]thiazin-2-ylmethyl]-benzoic acid; and 4-[1,1-dioxo-7-(3-phenyl-prop-1-ynyl)-1H-$1l^6$-benzo[e][1,2]thiazin-2-ylmethyl]-benzoic acid.

Also preferred is a compound of Formula I, or a pharmaceutically acceptable salt thereof, wherein $G_1$ and $G_2$ are as defined above and B is

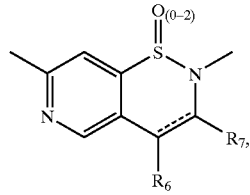

wherein - - -, $R_6$ and $R_7$ are as defined above for Formula I.

More preferred is a compound of Formula I, or a pharmaceutically acceptable salt thereof, selected from:

4-[1-oxo-7-(3-phenyl-prop-1-ynyl)-1H-$1l^4$- thia-2,6-diaza-naphthalen-2-ylmethyl]-benzoic acid; and 4-[1,1-dioxo-7-(3-phenyl-prop-1-ynyl)-1H-$1l^6$- thia-2,6-diaza-naphthalen-2-ylmethyl]-benzoic acid.

Also preferred is a compound of Formula I, or a pharmaceutically acceptable salt thereof, wherein $G_1$ and $G_2$ are as defined above and B is

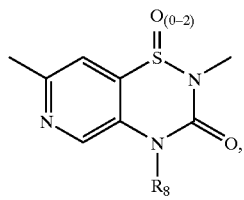

wherein $R_8$ is as defined above for Formula I.

More preferred is a compound of Formula I, or a pharmaceutically acceptable salt thereof, selected from:

- 4-[4-methyl-1,3-dioxo-7-(3-phenyl-prop-1-ynyl)-3,4-dihydro-1H-11$^4$-thia-2,4,6-triaza-naphthalen-2-ylmethyl]-benzoic acid;
- 4-[1,3-dioxo-7-(3-phenyl-prop-1-ynyl)-3,4-dihydro-1H-11$^4$-thia-2,4,6-triaza-naphthalen-2-ylmethyl]-benzoic acid; and
- 4-[4-methyl-1,1,3-trioxo-7-(3-phenyl-prop-1-ynyl)-3,4-dihydro-1H-11$^6$-thia-2,4,6-triaza-naphthalen-2-ylmethyl]-benzoic acid.

Also preferred is a compound of Formula I, or a pharmaceutically acceptable salt thereof, wherein $G_1$ and $G_2$ are as defined above and B is

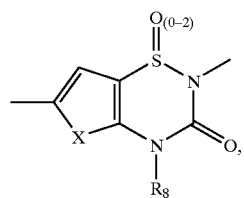

wherein X and $R_8$ are as defined above for Formula I.

More preferred is a compound of Formula I, or a pharmaceutically acceptable salt thereof, selected from:

- 4-[4-methyl-1,3-dioxo-6-(3-phenyl-prop-1-ynyl)3,4-dihydro-1H-11$^4$-thieno[2,3-e][1,2,4]thiadiazin-2-ylmethyl]-benzoic acid;
- 4-[1,3-dioxo-6-(3-phenyl-prop-1-ynyl)3,4-dihydro-1H-11$^4$-thieno[2,3-e][1,2,4]thiadiazin-2-ylmethyl]-benzoic acid;
- 4-[4-methyl-1,1,3-trioxo-6-(3-phenyl-prop-1-ynyl)3,4-dihydro-1H-11$^6$-thieno[2,3-e][1,2,4]thiadiazin-2-ylmethyl]-benzoic acid;
- 4-[1,1,3-trioxo-6-(3-phenyl-prop-1-ynyl)3,4-dihydro-1H-11$^6$-thieno[2,3-e][1,2,4]thiadiazin-2-ylmethyl]-benzoic acid.

Also preferred is a compound of Formula I, or a pharmaceutically acceptable salt thereof, wherein $G_1$ and $G_2$ are as defined above and B is

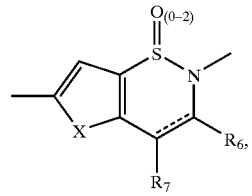

wherein —, X, $R_6$, and $R_7$ are as defined above for Formula I.

More preferred is a compound of Formula I, or a pharmaceutically acceptable salt thereof, selected from:

- 4-[1-oxo-6-(3-phenyl-prop-1-ynyl)-1H-11$^4$-thieno[2,3-e][1,2]thiazin-2-ylmethyl]-benzoic acid; and
- 4-[1,1-dioxo-6-(3-phenyl-prop-1-ynyl)-1H-11$^6$-thieno[2,3-e][1,2]thiazin-2-ylmethyl]-benzoic acid.

Also preferred is a compound of Formula I, or a pharmaceutically acceptable salt thereof, wherein $G_1$ and $G_2$ are as defined above and B is

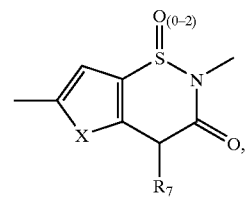

wherein X and $R_7$ are as defined above for Formula I.

More preferred is a compound of Formula I, or a pharmaceutically acceptable salt thereof, selected from:

- 4-[1,3-dioxo-6-(3-phenyl-prop-1-ynyl)-3,4-dihydro-1H-11$^4$-thieno[2,3-e][1,2]thiazin-2-ylmethyl]-benzoic acid; and
- 4-[1,1,3-trioxo-6-(3-phenyl-prop-1-ynyl)-3,4-dihydro-1H-11$^6$-thieno[2,3-e][1,2]thiazin-2-ylmethyl]-benzoic acid.

Also preferred is a compound of Formula I, or a pharmaceutically acceptable salt thereof, wherein $G_1$ and $G_2$ are as defined above and B is

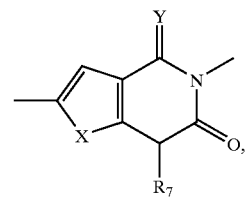

wherein X, Y, and $R_7$ are as defined above for Formula I.

More preferred is a compound of Formula I, or a pharmaceutically acceptable salt thereof, named:

- 4-[4,6-dioxo-2-(3-phenyl-prop-1-ynyl)-6,7-dihydro-4H-thieno[3,2-c]pyridin-5-ylmethyl]-benzoic acid.

Also preferred is a compound of Formula I, or a pharmaceutically acceptable salt thereof, wherein $G_1$ and $G_2$ are as defined above and B is

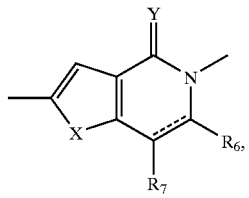

wherein - - -, X, Y, R₆, and R₇ are as defined above for Formula I.

More preferred is a compound of Formula I, or a pharmaceutically acceptable salt thereof, named:

4-[4-oxo-2-(3-phenyl-prop-1-ynyl)-4H-thieno[3,2-c]pyridin-5-ylmethyl]-benzoic acid.

Also preferred is a compound of Formula I, or a pharmaceutically acceptable salt thereof, wherein G₁ and G₂ are as defined above and B is

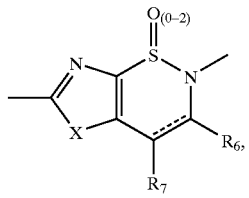

wherein - - -, X, R₆, and R₇ are as defined above for Formula I.

More preferred is a compound of Formula I, or a pharmaceutically acceptable salt thereof, selected from:

4-[4-oxo-2-(3-phenyl-prop-1-ynyl)-4H-1,4l⁴-dithia-3,5-diaza-inden-5-ylmethyl]-benzoic acid; and 4-[4,4-dioxo-2-(3-phenyl-prop-1-ynyl)-4H-1,4l⁶-dithia-3,5-diaza-inden-5-ylmethyl]-benzoic acid.

Also preferred is a compound of Formula I, or a pharmaceutically acceptable salt thereof, wherein G₁ and G₂ are as defined above and B is

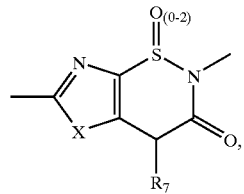

wherein X and R₇ are as defined above for Formula I.

More preferred is a compound of Formula I, or a pharmaceutically acceptable salt thereof, selected from:

4-[4,6-dioxo-2-(3-phenyl-prop-1-ynyl)-6,7-dihydro-4H-1,4l⁴-dithia-3,5-diaza-inden-5-ylmethyl]-benzoic acid; and 4-[4,4,6-trioxo-2-(3-phenyl-prop-1-ynyl)-6,7-dihydro-4H-1,4l⁶-dithia-3,5-diaza-inden-5-ylmethyl]-benzoic acid.

Also preferred is a compound of Formula I, or a pharmaceutically acceptable salt thereof, wherein G₁ and G₂ are as defined above and B is

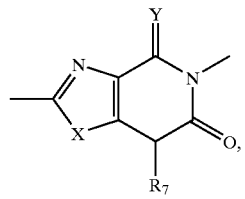

wherein X, Y, and R₇ are as defined above for Formula I.

More preferred is a compound of Formula I, or a pharmaceutically acceptable salt thereof, named:

4-[4,6-dioxo-2-(3-phenyl-prop-1-ynyl)-6,7-dihydro-4H-thiazolo[4,5-c]pyridin-5-ylmethyl-benzoic acid.

Also preferred is a compound of Formula I, or a pharmaceutically acceptable salt thereof, wherein G₁ and G₂ are as defined above and B is

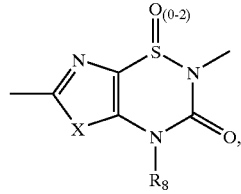

wherein X and R₈ are as defined above for Formula I.

More preferred is a compound of Formula I, or a pharmaceutically acceptable salt thereof, selected from:

4-[7-methyl-4,6-dioxo-2-(3-phenyl-prop-1-ynyl)-6,7-dihydro-4H-1,4l⁴-dithia-3,5,7-triaza-inden-5-ylmethyl]-benzoic acid;

4-[4,6-dioxo-2-(3-phenyl-prop-1-ynyl)-6,7-dihydro-4H-1,4l⁴-dithia-3,5,7-triaza-inden-5-ylmethyl]-benzoic acid;

4-[7-methyl-4,4,6-trioxo-2-(3-phenyl-prop-1-ynyl)-6,7-dihydro-4H-1,4l⁶-dithia-3,5,7-triaza-inden-5-ylmethyl]-benzoic acid; and 4-[4,4,6-trioxo-2-(3-phenyl-prop-1-ynyl)-6,7-dihydro-4H-1,4l⁶-dithia-3,5,7-triaza-inden-5-ylmethyl]-benzoic acid.

Also preferred is a compound of Formula I, or a pharmaceutically acceptable salt thereof, wherein G₁ and G₂ are as defined above and B is

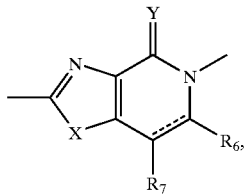

wherein - - -, X, Y, R₆, and R₇ are as defined above for Formula I.

More preferred is a compound of Formula I, or a pharmaceutically acceptable salt thereof, named:

4-[4-oxo-2-(3-phenyl-prop-1-ynyl)-4H-thiazolo[4,5-c]pyridin-5-ylmethyl]-benzoic acid.

Also preferred is a compound of Formula I selected from:

N-(4-Cyano-benzyl)-3-(3-[1,2,3]-triazol-1-yl-prop-1-ynyl)-benzamide;

N-(4-Cyano-benzyl)-3-(3-[1,2,3]-triazol-1-yl-prop-1-ynyl)-benzamide;

4-({3-[3-(4-Chloro-phenyl)-prop-1-ynyl]-benzoylamino}-methyl)-benzoic acid;

4-({3-[3-(4-Fluoro-phenyl)-prop-1-ynyl]-benzoylamino}-methyl)-benzoic acid;

3-Phenylethynyl-N-(4-Sulfamoyl-benzyl)-benzamide;

N-(4-Cyano-benzyl)-3-phenylethynyl-benzamide;

3-Phenethylethynyl-N-pyridin-4-yl-methyl-benzamide; and

3-[[3-(3-Phenethylethynyl-benzoylamino]-methyl}-benzoic acid; or a pharmaceutically acceptable salt thereof.

Also preferred is a compound of Formula I selected from:

4-({[5-(3-Phenyl-prop-1-ynyl)-pyridine-3-carbonyl]-amino}-methyl)-benzoic acid; and 4-{[(Phenylethynyl-pyridine-2-carbonyl)-amino]-methyl}-benzoic acid; or a pharmaceutically acceptable salt thereof.

Also preferred is a compound of Formula I selected from:

4-[1-Methyl-2,4-dioxo-6-(3-phenyl-prop-1-ynyl)-1,4-dihydro-2H-2λ$^4$-benzo[1,2,6]thiadiazin-3-yl methyl] benzoic acid;

4-[1-methyl-2,2,4-trioxo-6-(3-phenylprop-1-ynyl)-1,4-dihydro-2H-2λ$^6$-benzo[1,2,6]thiadiazin-3-ylmethyl] benzoic acid;

4-[1,1,3-Trioxo-7-(3-phenyl-prop-1-ynyl)-3,4-dihydro-1H-1λ$^6$-benzo[1,2,4]thiadiazin-2-ylmethyl]-benzoic acid;

2-(4-Methoxy-benzyl)-1,1-dioxo-7-(3-phenyl-prop-1-ynyl)-1,4-dihydro-2H-1λ$^6$-benzo[1,2,4]thiadiazin-3-one; and 4-[1,1,3-Trioxo-7-(4-phenyl-but-1-ynyl)-3,4-dihydro-1H-1λ$^6$-benzo[1,2,4]thiadiazin-2-ylmethyl]-benzoic acid; or a pharmaceutically acceptable salt thereof.

A further embodiment of this invention is a pharmaceutical composition comprising, a compound of Formula I, or a pharmaceutically acceptable salt thereof, or a tautomer thereof, admixed with a carrier, excipient, or diluent. Preferred compositions comprise a compound of Formulas II, III, IV, V, VI, or VII.

Another embodiment of this invention is a method for inhibiting MMP-13 in an animal, comprising administering to the animal an MMP-13 inhibiting amount of a compound of Formula I, or a pharmaceutically acceptable salt thereof, or a tautomer thereof.

A further embodiment is a method for treating a disease mediated by an MMP-13 enzyme, comprising administering to a patient suffering from such a disease an effective amount of a compound of Formula I, or a pharmaceutically acceptable salt thereof, or a tautomer thereof.

A preferred method of treatment according to this invention is treatment of a disease selected from cancer, especially breast carcinoma, and inflammation and heart failure. Other diseases to be treated according to preferred aspect of this invention include rheumatoid arthritis and osteoarthritis.

Another preferred method of treatment according to this invention is treatment of a disease selected from heart disease, multiple sclerosis, arthritis, other than osteoarthritis and rheumatoid arthritis, atherosclerosis, age-related macular degeneration, chronic obstructive pulmonary disease, psoriasis, asthma, cardiac insufficiency, inflammatory bowel disease, periodontal diseases, and osteoporosis.

DETAILED DESCRIPTION OF THE INVENTION

The compounds provided by this invention are those defined by Formula I, or a pharmaceutically acceptable salt thereof, or a tautomer thereof. In groups $G_1$, $G_2$, and B of Formula I, $R_1$ to $R_8$ include "$C_1-C_6$ alkyl" groups. These are straight and branched carbon chains having from 1 to 6 carbon atoms. Examples of such alkyl groups include methyl, ethyl, isopropyl, tert-butyl, neopentyl, and n-hexyl. The alkyl groups can be substituted if desired, with from 1 to 3 groups selected from hydroxy, amino, alkylamino, and dialkylamino, halo, trifluoromethyl, carboxy, nitro, and cyano.

Examples of $NR_1R_2$ or $NR_3R_4$ groups include amino, methylamino, di-isopropylamino, acetyl amino, propionyl amino, 3-aminopropyl amino, 3-ethylaminobutyl amino, 3-di-n-propylamino-propyl amino, 4-diethylaminobutyl amino, and 3-carboxypropionyl amino. $R_1$ and $R_2$, or $R_3$ and $R_4$, can independently be taken together with the nitrogen to which they are attached to form a ring having 3 to 7 carbon atoms and 1, 2, or 3 heteroatoms selected from the group consisting of nitrogen, substituted nitrogen, wherein substituted nitrogen is as defined below, oxygen, and sulfur. Examples of such cyclic $NR_1R_2$ or $NR_3R_4$ groups include pyrrolidinyl, piperazinyl, 4-methylpiperazinyl, 4-benzylpiperazinyl, pyridinyl, piperidinyl, pyrazinal, morpholinyl, and the like.

"Amino" means $NH_2$.

"Halo" includes fluoro, chloro, bromo, and iodo.

"Alkenyl" means straight and branched hydrocarbon radicals having from 2 to 6 carbon atoms and one double bond and includes ethenyl, 3-buten-1-yl, 2-ethenylbutyl, 3-hexen-1-yl, and the like.

"Alkynyl" means straight and branched hydrocarbon radicals having from 2 to 6 carbon atoms and one triple bond and includes ethynyl, 3-butyn-1-yl, propynyl, 2-butyn-1-yl, 3-pentyn-1-yl, and the like.

"Carbocycle" and "Cycloalkyl" mean a monocyclic or polycyclic hydrocarbyl group such as cyclopropyl, cycloheptyl, cyclooctyl, cyclodecyl, cyclobutyl, adamantyl, norpinanyl, decalinyl, norbornyl, cyclohexyl, and cyclopentyl. Such groups can be substituted with groups such as hydroxy, keto, and the like. Also included are rings in which 1 to 3 heteroatoms replace carbons. Such groups are termed "heterocycle" or "heterocyclyl", which means a cycloalkyl group also bearing at least one heteroatom selected from O, S, or $NR_2$, examples being oxiranyl, pyrrolidinyl, piperidyl, 4-methylpiperazinyl, tetrahydropyran, and morpholine.

"Alkoxy" refers to the alkyl groups mentioned above bound through oxygen, examples of which include methoxy, ethoxy, isopropoxy, tert-butoxy, and the like. In addition, alkoxy refers to polyethers such as —O—$(CH_2)_2$—O—$CH_3$, and the like.

"Alkanoyl" groups are alkyl linked through a carbonyl, ie, $C_1-C_5$—C(O)—. Such groups include formyl, acetyl, propionyl, butyryl, and isobutyryl.

"Acyl" means an alkyl or aryl (Ar) group bonded through a carbonyl group, ie, R—C(O)—. For example, acyl includes a $C_1-C_6$ alkanoyl, including substituted alkanoyl, wherein the alkyl portion can be substituted by $NR_1R_2$ or a carboxylic or heterocyclic group. Typical acyl groups include acetyl, benzoyl, and the like.

The alkyl, alkenyl, alkoxy, and alkynyl groups described above are optionally substituted, preferably by 1 to 3 groups selected from $NR_1R_2$, phenyl, substituted phenyl, heterocycle, thio $C_1$–$C_6$ alkyl, $C_1$–$C_6$ alkoxy, hydroxy, carboxy, $C_1$–$C_6$ alkoxycarbonyl, halo, nitrile, cycloalkyl, and a 5- or 6-membered carbocyclic ring or heterocyclic ring having 1 or 2 heteroatoms selected from nitrogen, substituted nitrogen, oxygen, and sulfur.

"Substituted nitrogen" means nitrogen bearing $C_1$–$C_6$ alkyl or $(CH_2)_n$Ph where n is 1, 2, or 3. Perhalo and polyhalo substitution is also embraced.

Examples of substituted alkyl groups include 2-aminoethyl, pentachloroethyl, trifluoromethyl, 2-diethylaminoethyl, 2-dimethylaminopropyl, ethoxycarbonylmethyl, 3-phenylbutyl, methanylsulfanylmethyl, methoxymethyl, 3-hydroxypentyl, 2-carboxybutyl, 4-chlorobutyl, 3-cyclopropylpropyl, pentafluoroethyl, benzyl($B_n$), 3-morpholinopropyl, piperazinylmethyl, pyridyl-4-methyl(Py-4-me), 3-(pyridyl-4-thio)propyl, and 2-(4-methylpiperazinyl)ethyl.

Examples of substituted alkynyl groups include 2-methoxyethynyl, 2-ethylsulfanyethynyl, 4-(1-piperazinyl)-3-(butynyl), 3-phenyl-5-hexynyl, 3-diethylamino-3-butynyl, 4-chloro-3-butynyl, 4-cyclobutyl-4-hexenyl, and the like.

Typical substituted alkoxy groups include aminomethoxy, trifluoromethoxy, 2-diethylaminoethoxy, 2-ethoxycarbonylethoxy, 3-hydroxypropoxy, 6-carboxhexyloxy, and the like.

Further, examples of substituted alkyl, alkenyl, and alkynyl groups include dimethylaminomethyl, carboxymethyl, 4-dimethylamino-3-buten-1-yl, 5-ethylmethylamino-3-pentyn-1-yl, 4-morpholinobutyl, 4-tetrahydropyrinidylbutyl, 3-imidazolidin-1-ylpropyl, 4-tetrahydrothiazol-3-yl-butyl, phenylmethyl, 3-chlorophenylmethyl, and the like.

The terms "Ar" and "aryl" refer to unsubstituted and substituted aromatic groups. Heteroaryl groups have from 4 to 10 ring atoms, which are carbon atoms and from 1 to 4 of which are independently selected from the group consisting of O, S, and N. Preferred heteroaryl groups have 1 or 2 heteroatoms in a 5- or 6-membered aromatic ring. Mono- and bicyclic aromatic ring systems are included in the definition of aryl and heteroaryl. Typical aryl groups include phenyl and naphthyl. Typical substituted aryl groups include 2,4,6-tribromophenyl, 4,7-dichloronaphthyl, 3-chlorophenyl, 3,4-methylenedioxyphenyl, and 2,6-dibromophenyl. Typical heteroaryl groups include pyridyl, benzothienyl, furanyl, indolyl, benzotriazolyl, indazolyl, pyrrolyl, pyrazolyl, imidazolyl, thiazolyl, and the like.

Typical substituted heteroaryl groups include 3-methylpyridyl, 4-thiopyridyl, 4-ethylbenzothienyl, and 3,4-diethylfuranyl.

Preferred Ar groups are phenyl and phenyl substituted by 1, 2, or 3 groups independently selected from alkyl, alkoxy, thio, thioalkyl, heteroaryl, heterocyclyl, halo, hydroxy, —$COOR_9$, trifluoromethyl, nitro, amino of the formula —$NR_1R_2$, and $T(CH_2)_mQR_3$ or $T(CH_2)_mCO_2R_3$, wherein m is 1 to 6; T is O, S, $NR_3$, $N(O)R_3$, $NR_1R_2Y$, or $CR_1R_2$, Q is O, S, $NR_3$, $N(O)R_3$, or $NR_1R_2Y$, wherein $R_1$ and $R_2$ are as described above, and $R_9$ is alkyl or substituted alkyl, for example, methyl, trichloroethyl, diphenylmethyl, and the like. The alkyl and alkoxy groups can be substituted as defined above. For example, typical groups are carboxyalkyl, alkoxycarbonylalkyl, hydroxyalkyl, hydroxyalkoxy, and alkoxyalkyl. Examples of substituted phenyl are 3-methoxyphenyl, 4-(1H-tetrazol-5-yl)phenyl 2,6-dichlorophenyl, 3-nitrophenyl, 4-dimethylaminophenyl, and biphenyl.

The phrase "tertiary organic amine" means a trisubstituted nitrogen group wherein the 3 substituents are independently selected from $C_1$–$C_{12}$ alkyl, $C_3$–$C_{12}$ cycloalkyl, benzyl, or wherein two of the substituents are taken together with the nitrogen atom to which they are attached to form a 5- or 6-membered, monocyclic heterocycle containing one nitrogen atom and carbon atoms, and the third substituent is selected from $C_1$–$C_{12}$ alkyl and benzyl, or wherein the three substituents are taken together with the nitrogen atom to which they are attached to form a 7- to 12-membered bicyclic heterocycle containing 1 or 2 nitrogen atoms and carbon atoms, and optionally a C=N double bond when 2 nitrogen atoms are present. Illustrative examples of tertiary organic amine include triethylamine, diisopropylethylamine, benzyl diethylamino, dicyclohexylmethyl-amine, 1,8-diazabicycle[5.4.0]undec-7-ene (DBU), 1,4-diazabicyclo[2.2.2]octane (TED), and 1,5-diazabicycle[4.3.0]non-5-ene.

The term "comprising," which is synonymous with the terms "including," "containing," or "characterized by," is inclusive or open-ended, and does not exclude additional, unrecited elements or method steps from the scope of the invention that is described following the term.

The phrase "consisting of" is closed-ended, and excludes any element, step, or ingredient not specified in the description of the invention that follows the phrase.

The phrase "consisting essentially of" limits the scope of the invention that follows to the specified elements, steps, or ingredients, and those further elements, steps, or ingredients that do not materially affect the basic and novel characteristics of the invention.

The phrase "pharmaceutical composition" means a composition suitable for administration in medical or veterinary use.

The term "admixed" and the phrase "in admixture" are synonymous and mean in a state of being in a homogeneous or heterogeneous mixture. Preferred is a homogeneous mixture.

The term "patient" means a mammal. Preferred patients are humans, cats, dogs, cows, horses, pigs, and sheep.

The term "animal" means a mammal, as defined above. Preferred animals include humans, cats, dogs, horses, pigs, sheep, cows, monkeys, rats, mice, guinea pigs, and rabbits.

The phrase "anticancer effective amount" means an amount of invention compound, or a pharmaceutically acceptable salt thereof, or a tautomer thereof, sufficient to inhibit, halt, or cause regression of the cancer being treated in a particular patient or patient population. For example in humans or other mammals, an anticancer effective amount can be determined experimentally in a laboratory or clinical setting, or may be the amount required by the guidelines of the United States Food and Drug Administration, or equivalent foreign agency, for the particular cancer and patient being treated.

The phrase "anti-arthritic effective amount" means an amount of invention compound, or a pharmaceutically acceptable salt thereof, or a tautomer thereof, sufficient to inhibit, halt, or cause regression of the arthritis being treated in a particular patient or patient population. For example in humans or other mammals, an anti-arthritic effective amount can be determined experimentally in a laboratory or clinical setting, or may be the amount required by the guidelines of the United States Food and Drug Administration, or equivalent foreign agency, for the particular arthritis and patient being treated.

The phrase "MMP-13 inhibiting amount" means an amount of invention compound, or a pharmaceutically acceptable salt thereof, or a tautomer thereof, sufficient to inhibit an enzyme matrix metalloproteinase-13, including a truncated form thereof, including a catalytic domain thereof, in a particular animal or animal population. For example in a human or other mammal, an MMP-13 inhibiting amount can be determined experimentally in a laboratory or clinical setting, or may be the amount required by the guidelines of the United States Food and Drug Administration, or equivalent foreign agency, for the particular MMP-13 enzyme and patient being treated.

It should be appreciated that determination of proper dosage forms, dosage amounts, and routes of administration, is within the level of ordinary skill in the pharmaceutical and medical arts, and is described below.

The phrases "effective amount" and "therapeutically effective amount" are synonymous and mean an amount of a compound of the present invention, a pharmaceutically acceptable salt thereof, or a solvate thereof, sufficient to effect an improvement of the condition being treated when administered to a patient suffering from a disease that is mediated by MMP-13 and optionally from 0 to 12 additional MMP enzymes.

The term "$IC_{50}$" means the concentration of test compound required to inhibit activity of a biological target, such as a receptor or enzyme, by 50%.

The term "tautomer" means a form of invention compound existing in a state of equilibrium with an isomeric form of the invention compound, wherein the invention compound is able to react according to either form by virtue of the ability of the forms to interconvert by isomerization in situ, including in a reaction mixture, in an in vitro biological assay, or in vivo.

The term "(E)" means entgegen, and designates that the conformation about the double bond to which the term refers is the conformation having the two higher ranking substituent groups, as determined according to the Cahn-Ingold-Prelog ranking system, on opposite sides of the double bond. An (E) double bond is illustrated below by the compound of Formula (W)

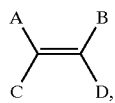

(W)

wherein the two higher-ranking substituents are groups A and D.

The term "(Z)" means zusammen, and designates that the conformation about the double bond to which the term refers is the conformation having the two higher ranking substituent groups, as determined according to the Cahn-Ingold-Prelog ranking system, on the same side of the double bond. A (Z) double bond is illustrated below by the compound of Formula (X)

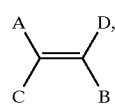

(X)

wherein the two higher-ranking substituents are groups A and D.

The phrase "inert atmosphere" means an atmosphere that consists essentially of nitrogen gas, or argon gas, or mixtures thereof.

It should be appreciated that the matrix metalloproteinases include the following enzymes:

MMP-1, also known as interstitial collagenase, collagenase-1, or fibroblast-type collagenase;

MMP-2, also known as gelatinase A or 72 kDa Type IV collagenase;

MMP-3, also known as stromelysin or stromelysin-1;

MMP-7, also known as matrilysin or PUMP-1;

MMP-8, also known as neutrophil collagenase or polymorphonuclear-type ("PMN-type") collagenase;

MMP-9, also known as gelatinase B or 92 kDa Type IV collagenase;

MMP-10, also known as stromelysin-2;

MMP-11, also known as stromelysin-3;

MMP-12, also known as metalloelastase;

MMP-13, also known as collagenase-3;

MMP-14, also known as membrane-type ("MT") MMP-1 or MT-MMP-1;

MMP-15, also known as MT-MMP-2;

MMP-16, also known as MT-MMP-3;

MMP-17, also known as MT-MMP-4;

MMP-18; and

MMP-19.

As discussed above, one aspect of the present invention is novel compounds that are selective inhibitors of the enzyme MMP-13. A selective inhibitor of MMP-13, as used in the present invention, is a compound that is ≧5×more potent in vitro versus MMP-13 than versus at least one other matrix metalloproteinase enzyme such as, for example, MMP-1, MMP-2, MMP-3, MMP-7, MMP-8, MMP-9, or MMP-14, or versus tumor necrosis factor alpha convertase ("TACE"). A preferred aspect of the present invention is novel compounds that are selective inhibitors of MMP-13 versus MMP-1.

Some of the compounds of the present invention may exist as tautomeric forms, which interchange via, for example, enolization and the like. All tautomeric forms are within the scope of the present invention.

Some compounds of the present invention have alkenyl groups, which may exist as entgegen or zusammen conformations, in which case all geometric forms thereof, both entgegen and zusammen, cis and trans, and mixtures thereof, are within the scope of the present invention.

Some compounds of the present invention have cycloalkyl groups, which may be substituted at more than one carbon atom, in which case all geometric forms thereof, both cis and trans, and mixtures thereof, are within the scope of the present invention.

The compounds to be used in the present invention can exist in unsolvated forms as well as solvated forms, including hydrated forms. In general, the solvated forms, including hydrated forms, are equivalent to unsolvated forms and are intended to be encompassed within the scope of the present invention. Some of the invention compounds may have one or more chiral centers, and as such can exist as individual enantiomers and mixtures. This invention contemplates all racemic mixtures, pure enantiomers, as well as geometric and positional isomers.

The compounds of Formulas I to VII are capable of further forming both pharmaceutically acceptable formulations comprising salts, including but not limited to, acid addition and/or base salts, solvents, and N-oxides of a compound of Formulas I to VII. This invention also provides pharmaceutical formulations comprising a compound of Formulas I to VII together with a pharmaceutically acceptable carrier, diluent, or excipient therefor. All of these forms can be used in the method of the present invention.

Pharmaceutically acceptable acid addition salts of the compounds of Formulas I to VII include salts derived form inorganic acids such as hydrochloric, nitric, phosphoric, sulfuric, hydrobromic, hydriodic, phosphorus, and the like, as well as, the salts derived from organic acids, such as aliphatic mono- and dicarboxylic acids, phenyl-substituted alkanoic acids, hydroxy alkanoic acids, alkanedioic acids, aromatic acids, aliphatic, and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are the salts of amino acids such as arginate, gluconate, galacturonate, and the like; see, for example, Berge et al., "Pharmaceutical Salts," *J. of Pharmaceutical Science*, 1977;66:1–19.

The acid addition salts of the basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metal hydroxides, or of organic amines. Examples of metals used as cations are sodium, potassium, magnesium, calcium, and the like. Examples of suitable amines are N,N'-dibenzylethylenediamine, chloroprocaine, choline, diethanolamine, ethylenediamine, N-methylglucamine, and procaine; see, for example, Berge et al., supra.

The base addition salts of acidic compounds are prepared by contacting the free acid form with a sufficient amount of the desired base to produce the salt in the conventional manner. The free acid form may be regenerated by contacting the salt form with an acid and isolating the free acid in a conventional manner. The free acid forms differ from their respective salt forms somewhat in certain physical properties such as solubility in polar solvents, but otherwise the salts are equivalent to their respective free acid for purposes of the present invention.

The compounds of the present invention can be formulated and administered in a wide variety of oral and parenteral dosage forms, including transdermal and rectal administration. All that is required is that an MMP inhibitor be administered to a mammal suffering from a disease in an effective amount, which is that amount required to cause an improvement in the disease and/or the symptoms associated with such disease. It will be recognized to those skilled in the art that the following dosage forms may comprise as the active component, a compound of Formula I or a tautomer thereof, or a corresponding pharmaceutically acceptable salt or solvate of a compound of Formula I, or a tautomer thereof.

The invention compounds are prepared by methods well known to those skilled in the art of organic chemistry. The compounds of Formula I are prepared utilizing commercially available starting materials, or reactants that are readily prepared by standard organic synthetic techniques.

Further, syntheses of the compounds of the present invention may utilize starting materials, intermediates, or reaction products that contain a reactive functional group. A reactive functional group may be protected during chemical reactions using protecting groups that render the reactive groups substantially inert to the reaction conditions. At a step in a synthesis of a compound of the present invention subsequent to the chemical reaction requiring a protecting group, and appropriate to the synthetic strategy employed, the protecting group may be removed. See, for example, *Protective Groups in Organic Synthesis*, $2^{nd}$ ed., Greene T. W. and Wuts P. G., John Wiley & Sons, New York, N.Y., 1991, which is hereby incorporated by reference. Thus, for example, protecting groups such as the following may be utilized to protect suitable amino, hydroxyl, and other groups of related reactivity: carboxylic acyl groups, such as formyl, acetyl, and trifluoroacetyl; alkoxycarbonyl groups, such as ethoxycarbonyl, t-butoxycarbonyl (BOC), and $\beta,\beta,\beta$-trichloroethoxycarbonyl (TCEC), $\beta$-iodoethoxycarbonyl; aryloxycarbonyl groups, such as benzyloxycarbonyl (CBZ), p-methoxybenzyloxycarbonyl, and phenoxycarbonyl; trialkyl silyl groups, such as trimethylsilyl and t-butyldimethylsilyl (TBDMS); and groups such as trityl, tetrahydropyranyl, vinyloxycarbonyl, o-nitrophenylsulfenyl, diphenylphosphinyl, p-toluenesulfonyl, and benzyl may all be utilized. The protecting group may be removed, after completion of the synthetic reaction of interest, by procedures known to those skilled in the art. For example, a BOC group may be removed by acidolysis, a trityl group by hydrogenolysis, TBDMS by treatment with fluoride ions, and TCEC by treatment with zinc. Use of protecting groups in organic synthesis is well within the skill of the average artisan.

The compounds of the present invention can be prepared according to the various synthetic schemes that follow. Protecting groups may be used when appropriate throughout many of the schemes. Although specifically noted in certain schemes, the appropriate use and choice of protecting groups is well known by one skilled in the art, and is not limited to the specific examples below. It is also understood that such groups not only serve to protect chemically reactive sites, but also to enhance solubility or otherwise change physical properties. A good general reference for protecting group preparation and deprotection is "Protective Groups in Organic Synthesis" by Theodora Green, supra. A number of general reactions such as oxidations and reductions are not shown in detail but can be done by methods understood by one skilled in the art. General transformations are reviewed in "Comprehensive Organic Transformation" by Richard Larock, and the series "Compendium of Organic Synthetic Methods" (1989) published by Wiley-Interscience.

It should be appreciated that reagents, solvents, and starting materials necessary for the preparation of the compounds of the invention may be purchased from a number of commercial sources or may be readily prepared by a number of methods well known to one of average skill in the art of organic chemistry. Further, reactions used to prepare the invention compounds can be carried out under a wide variety of conditions comprising solvents, reagents, catalysts, temperatures, time, atmosphere, and pressure.

Different methods may be used to prepare the invention compounds. However for purposes of practicing the invention, which comprises compounds, pharmaceutical compositions, and methods of preventing or treating patients with the disorders or diseases recited above, it does not matter how the compounds are made.

A compound of Formula I, or a pharmaceutically acceptable salt thereof, may be prepared by one of ordinary skill in the art of organic chemistry by adapting various synthetic procedures which are well known in the art of organic chemistry. A wide variety of synthetic procedures may be found in the literature in, for example, *Reagents for Organic Synthesis*, by Fieser and Fieser, John Wiley & Sons, Inc., New York, 2000; *Comprehensive Organic Transformations*, by Richard C. Larock, VCH Publishers, Inc., New York, 1989; the series *Compendium of Organic Synthetic Methods* (1989) by Wiley-Interscience; and the text *Advanced Organic Chemistry*, 5th edition, by Jerry March, Wiley-Interscience, New York (2001). Synthetic procedures directed specifically to the preparation of a wide variety of heterocycles may be found in the *Handbook of Heterocyclic Chemistry*, by Alan R. Katritzky, Pergamon Press Ltd., London, (1985).

Alternatively, a skilled artisan may find methods useful for preparing the invention compounds in the chemical literature by searching widely available databases such as, for example, those available from the *Chemical Abstracts Service*, Columbus, Ohio, or *MDL Information Systems GmbH* (formerly *Beilstein Information Systems GmbH*), Frankfurt, Germany. These databases may be searched using keywords or structures, including structures of reactants and/or reaction products.

Preparations of the compounds of the present invention may use starting materials, reagents, solvents, and catalysts that may be purchased from commercial sources or they may be readily prepared by adapting procedures in the references or resources cited above. Commercial sources of starting materials, reagents, solvents, and catalysts useful in preparing invention compounds include, for example, *The Aldrich Chemical Company*, and other subsidiaries of Sigma-Aldrich Corporation, St. Louis, Mo., BACHEM, BACHEM A. G., Switzerland, or *Lancaster Synthesis Ltd.*, United Kingdom.

Particularly, compounds of Formula I may be prepared according to the synthetic route outlined in Scheme 1.

Scheme 1

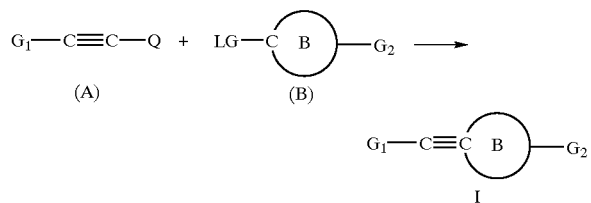

In Scheme I, a compound of formula (A), wherein Q is hydrogen and $G_1$ is as defined above for Formula I, is allowed to react with a compound of formula (B), wherein LG is a leaving group selected from Cl, Br, I, and $CF_3SO_3$, and $G_2$ and B are as defined above for Formula I, in the presence of a suitable coupling reagent such as a palladium catalyst, including bis(triphenylphosphinyl) palladium chloride palladium tetrakis triphenylphosphine, palladium acetate, or palladium chloride, in the presence of a base such as a tertiary organic amine, including triethylamine or diisopropylethylamine, or potassium acetate in a suitable aprotic solvent such as tetrahydrofuran ("THF"), heptane, or ethyl acetate to yield a compound of Formula I, wherein $G_1$, $G_2$, and B are as defined above for Formula I. This coupling reaction works for a variety of B groups, including aryl or heteroaryl B groups. See *Comprehensive Organic Transformations*, by Richard C. Larock, VCH Publishers, Inc, New York, 1989:302–303 and references cited therein; and *Advanced Organic Chemistry* by Jerry March, John Wiley & Sons, New York, 4th edition, 1992:717–718, and references cited therein.

Alternatively in Scheme 1, a compound of formula (A), wherein Q is a metal derivative such as ZnCl, Mg—(Cl, Br, or I) $SnR_3$, wherein R is $C_1$–$C_6$ alkyl, such as n-butyl, or Cu, and $G_1$ is as defined above for Formula I, is allowed to react with a compound of formula (B), wherein LG is a leaving group selected from Cl, Br, I, and $CF_3SO_3$, and $G_2$ and B are as defined above for Formula I, in the presence of a palladium catalyst as defined immediately above in a suitable solvent such as heptane, THF, and the like, to give a compound of Formula I, wherein $G_1$, $G_2$, and B are as defined above for Formula I.

Alternatively in Scheme 1, a compound of formula (A) wherein Q is Br or I and $G_1$ is as defined above for Formula I, is allowed to react with a compound of formula (B), wherein LG is a Cu (I) derivative such as $Cu^+$, hemi $Cu^+$/hemi $Li^+$, or CuCNLi, in a solvent such as THF, ethyl ether, heptane, and the like to give a compound of Formula I wherein $G_1$, $G_2$, and B are as defined above for Formula I (see La Rock, supra, 1989:305).

Compounds of formula (A), wherein Q is hydrogen or a metal derivative as defined above for Scheme 1, may be prepared by a number of methods well-known to an artisan of ordinary skill in the organic chemistry art (see La Rock, supra, 1989;1057–1058), and references cited therein. Examples of such methods are illustrated in Scheme 2.

Scheme 2

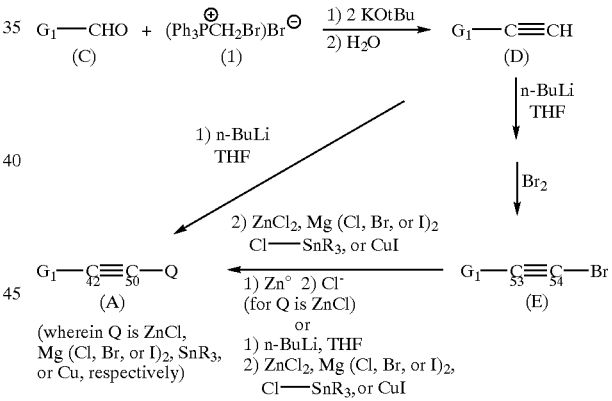

In Scheme 2, a compound of formula (C), wherein $G_1$ is as defined above for Formula I, is allowed to react with a compound of Formula I, in the presence of potassium tertiary-butoxide (2 mol equivalents) in a solvent such as THF, ethyl acetate, benzene, and the like, followed by addition of water to give a compound of formula (D). The compound of formula (D) is allowed to react with a strong base such as n-butyl lithium, tertiary-butyl lithium, sodium hydride, and the like, followed by reaction with a metal derivative such as $ZnCl_2$, a magnesium dihalide, wherein halide is chloride, bromide, or iodide, a trialkyl tin chloride (e.g., tri(n-butyl)tin chloride), or copper (I) iodide to give a compound of formula (A).

Alternatively in Scheme 2, the compound of formula (D) is allowed to react with a strong base such a n-butyl lithium, tertiary-butyl lithium, or sodium hydride, followed by reaction with the intermediate so formed with bromine (or iodine) to give a compound of formula (E). The compound of formula (E) is allowed to react with zinc metal and a source of chloride to provide a compound of formula (A) wherein Q is ZnCl, or the compound of formula (E) is allowed to react with a base such as n-butyl lithium followed by a metal derivative such as zinc chloride; a magnesium dihalide, wherein halide is chloride, bromide, or iodide; trialkyl tin chloride; or copper (I) iodide to give a compound of formula (A), wherein Q is ZnCl, Mg(Cl, Br, or I)$_2$, SnR$_3$, or Cu, respectively.

A compound of formula (B) wherein LG, B, and G$_2$ are as defined above for Formula I may be prepared by methods that are known to an artisan of ordinary skill in the synthetic organic chemistry art or may be purchased from sources of commercial organic compounds such as the Aldrich Chemical Company of Milwaukee, Wis. Illustrative examples of the preparations of a compound of formula (B) are outlined in Schemes 3 to 6.

Scheme 3

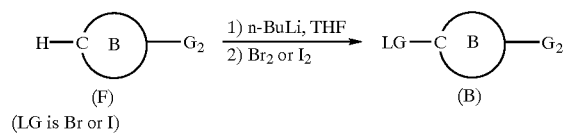

Scheme 4

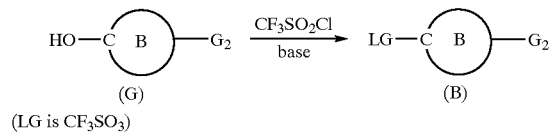

Scheme 5

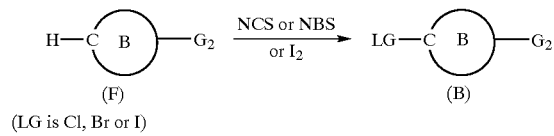

Scheme 6

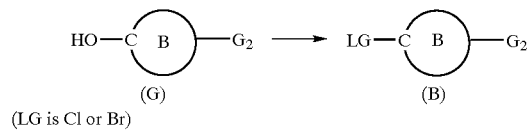

In Scheme 3, a compound of formula (F), wherein B and G$_2$ are as defined above for Formula I, is allowed to react with a base such as n-butyl lithium, sodium hydride, or potassium hexamethyldisilazide ("KHMDS") in an aprotic solvent such as THF, dimethylsulfoxide ("DMSO"), or heptane, followed by reaction of the intermediate organometallic species which results with bromine or iodine to give a compound of formula (B), wherein LG is Br or I, respectively.

In Scheme 4, a compound of formula (G), wherein B and G$_2$ are as defined above for Formula I, is allowed to react with trifluoromethanesulfonyl chloride in the presence of a nonnucleophilic base such as sodium hydride, triethylamine, pyridine, and the like, in an aprotic solvent to give a compound of formula (B), wherein LG is CF$_3$SO$_3$.

In Scheme 5, a compound of formula (F) as described above is allowed to react with a halogenating reagent such as N-chlorosuccinimide ("NCS"), N-bromosuccinimide ("NBS"), iodine, chlorine, bromine, SO$_2$Cl$_2$, Br$_2$/CCl$_4$, and the like optionally in the presence of a catalyst such as AlCl$_3$, FeCl$_3$, silica, alumina, or acetic acid to give a compound of formula (B), wherein LG is Cl, Br, or I.

In Scheme 6, a compound of formula (G) as described above is allowed to react with a halogenating reagent selected from POCl$_3$, POCl$_3$/PCl$_5$, PCl$_5$, COCl$_2$/PPh$_3$, or Br$_2$/PPh$_3$ to yield a compound of formula (B), wherein LG is Cl or Br.

Compounds of formulas (F) and (G) may be prepared by methods well known to an artisan of ordinary skill in the synthetic organic chemistry art or purchased from commercial sources. For example, these methods are described in Katristky, supra, 1985.

The following detailed examples further illustrate the synthesis of typical invention compounds of Formula I. The examples are representative only, and are not to be construed as limiting the invention in any respect.

EXAMPLE 1

2-Benzyl-4-methyl-1,1-dioxo-7-(3-phenyl-prop-1ynyl)-1,4-dihydro-2H-11$^6$-benzo[1,2,4]thiadiazin-3-one

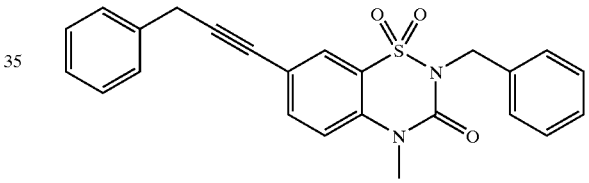

Step (1): N-(4-bromo-phenyl)-formamide

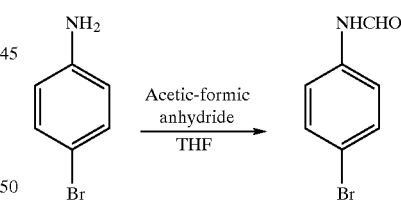

A 5-Liter round bottom flask was charged with acetic anhydride (488 mL, 5.2 mol) and cooled to 0° C. Formic acid (240 mL, 6.4 mol) was then added at a rate that did not elevate the temperature of the reaction mixture above 10° C. After the formic acid was added, the temperature of the reaction was raised to 50–60° C. and stirred for 3 hours. The reaction was then cooled to 0° C. and 400 mL of THF was added. A solution of 4-bromoaniline (344 g, 2.0 mol) in 800 mL of THF was added dropwise. After the addition was complete, the reaction was allowed to stir at this temperature for 4 hours. The reaction was checked by thin-layer chromatography and found to be complete. The reaction mixture was transferred to a round bottom flask and the solvent was removed in vacuo. When the solvent had been removed, the residue crystallized. The solid was triturated with heptane and filtered. Obtained 396.8 grams of desired N-(4-bromophenyl)-formamide. Yield 99.2% The spectral properties of the solid were consistent with the desired material.

Step (2): (4-bromo-phenyl)-methyl-amine

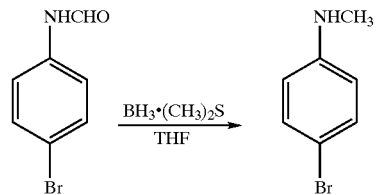

To a stirred 2M solution of borane methyl sulfide complex in THF (580 mL, 1.16 mol) at 0° C. was slowly added a solution of N-(4-bromo-phenyl)-formamide (Example 1, Step (1), 93 g., 0.465 mol) in 280 mL of THF so that the temperature of the solution did not rise above 5° C. Once the addition of the formanilide was complete, the reaction was brought to reflux and stirred for 3 hours. The reaction was then cooled to 0° C. and 190 mL of methanol was added slowly to control the frothing of the reaction. Then hydrogen chloride gas was bubbled into the solution until the pH was approximately 2. The solvents were removed in vacuo to afford a solid. The solid was dissolved in water and the pH was raised to 10, and the solution was extracted twice with ethyl ether. The combined ether extracts were washed twice with brine and dried over sodium sulfate. Removal of the ether solvent afforded 85.5 grams (98.8%) of (4-bromo-phenyl)-methyl-amine. The spectral properties of the oil were consistent with the desired material. High performance liquid chromatography ("HPLC") analysis revealed that the oil was greater than 95% of 4-bromophenyl-N-methylaniline. This material was used in the next step without purification.

Step (3): 7-Bromo-4-methyl-1,1-dioxo-1,4-dihydro-2H-1l$^6$-benzo[1,2,4]thiadiazin-3-one

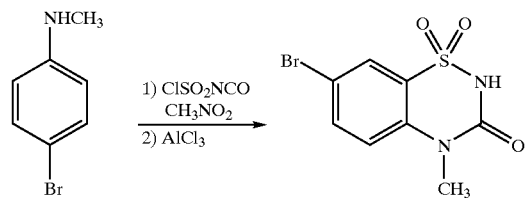

To a stirred, cold (0° C.) solution of chlorosulfonylisocyanate (107 mL, 1.22 mol) in 200 mL of nitromethane, was added a solution of 4-methylaminobromobenzene (Example 1, Step (2), 188.6 g, 1.02 mol) in 700 mL of nitromethane, dropwise over 30 minutes while keeping the temperature of the reaction during the addition below 10° C. The solution was allowed to stir at 0° C. for one hour and then aluminum chloride (176.8 g, 1.33 mol) was added and the reaction was brought to reflux and stirred for 2 hours. The reaction was cooled and checked by TLC. No starting aniline remained. The solvent was removed on the rotary evaporator and the thick, dark, gummy residue was poured over ice. A gray clumpy solid formed. The clumps were broken up and filtered and washed thoroughly with water. The solid was then dissolved in 1N NaOH solution, and the solution was washed twice with a 1:1 mixture of ether and ethyl acetate. The combined organic extracts were then backwashed with 1N NaOH solution, and the 1N NaOH solution was combined with the previous aqueous extracts. The aqueous layer was cooled and then acidified to pH 3 by the addition of concentrated hydrochloric acid. A thick, opalescent solid formed which was collected by filtration and washed thoroughly with water. The off-white solid was dried in a vacuum oven overnight at 50° C. to afford 230 grams (77.4%) of 7-bromo-4-methyl-1,1-dioxo-1,4-dihydro-2H-1l$^6$-benzo[1,2,4]thiadiazin-3-one.

Step (4): 2-Benzyl-7-bromo-4-methyl-1,1-dioxo-1,4-dihydro-2H-1l$^6$-benzo[1,2,4]thiadiazin-3-one

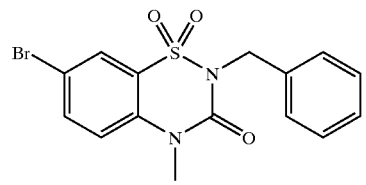

To a solution of 7-bromo-4-methyl-1,1-dioxo-1,4-dihydro-2H-1l$^6$-benzo[1,2,4]thiadiazin-3-one (Example 1, Step (3), 2.00 g, 6.87 mmol) in 30 mL of dimethylformamide was added N,N-diisopropylethylamine (1.79 mL, 10.3 mmol). After stirring for 5 minutes, benzyl bromide (0.899 mL, 7.56 mmol) was added to the reaction mixture. After stirring at room temperature for 24 hours, to the resulting black solution was added 20 mL of H$_2$O. The precipitated product was filtered and washed with 10 mL of H$_2$O to give 2.45 g (93.5%) of 2-Benzyl-7-bromo-4-methyl-1,1-dioxo-1,4-dihydro-2H-1l$^6$-benzo[1,2,4]thiadiazin-3-one: mp 155–157° C.; IR (KBr) 3076, 1696, 1588, 1484, 1311, 1173 cm$^{-1}$; $^1$H NMR (400 MHz, DMSO-d$_6$) δ 3.48 (s, 3H, NCH$_3$), 5.05 (s, 2H, NCH$_2$Ar), 7.10 (d, J=9.03 Hz, 1H, ArH), 7.23–7.27 (m, 3H, ArH), 7.43 (d, J=7.57 Hz, 2H, ArH), 7.73 (dd, J=5.86, 3.66 Hz, 1H, ArH), 8.02 (d, J=2.44 Hz, 1H, ArH); MS(APCI+): m/z 381.0 (MH$^-$). Anal. Calcd for C$_{15}$H$_{13}$N$_2$O$_3$S$_1$Br$_1$: C, 47.26; H, 3.44; N, 7.35. Found: C, 47.20; H, 3.45; N, 7.16.

Step (5): 2-benzyl-4-methyl-1,1-dioxo-7-(3-phenyl-prop-1ynyl)-1,4-dihydro-2H-1l$^6$-benzo[1,2,4]thiadiazin-3-one To a solution of CuI (0.010 g, 0.052 mmol) and Pd (PhCN)$_2$Cl$_2$ (0.030 g, 0.079 mmol), (after purging with nitrogen for 5 min) in 26 mL of anhydrous dioxane was added P(t-Bu)$_3$ (0.032 g, 0.157 mmol), HN(i-Pr)$_2$ (1.10 mL, 7.87 mmol), 3-phenyl-1-propyne (0.979 mL, 7.87 mmol), and 2-benzyl-7-bromo-4-methyl-1,1-dioxo-1,4-dihydro-2H-1l$^6$-benzo[1,2,4]thiadiazin-3-one (Example 1, Step (4), 1.00 g, 2.62 mmol). Under a nitrogen atmosphere, the reaction mixture was stirred at room temperature for 24 hours. After the reaction was completed, ethyl acetate (50 mL) was added and white solids (H$_2$N(I—Pr)$_2$Br) were filtered through celite. The filtrate was concentrated and triturated with diethyl ether to give 0.800 g (73.4%) of 2-benzyl-4-methyl-1,1-dioxo-7-(3-phenyl-prop-1ynyl)-1,4-dihydro-2H-1l$^6$-benzo[1,2,4]thiadiazin-3-one as a yellow solid: mp 125–127° C.; IR (KBr) 3031, 2868, 1693, 1606, 1499, 1333, 1174 cm$^{-1}$; $^1$H NMR (400 MHz, CDCl$_3$) δ 3.49 (s, 3H, NCH$_3$), 3.84 (s, 2H, CCH$_2$Ar), 5.05 (s, 2H, NCH$_2$Ar), 7.15 (d, J=8.80 Hz, 1H, ArH), 7.24–7.44 (m, 10H, ArH), 7.67 (dd, J=8.00, 2.00 Hz, 1H, ArH), 7.97 (d, J=1.95 Hz, 1H, ArH); MS(APCI+): m/z 417.2 (MH$^+$). Anal. Calcd for C$_{24}$H$_{20}$N$_2$O$_3$S$_1$: C, 69.21; H, 4.84; N, 6.73. Found: C, 69.17; H, 4.86; N, 6.55.

EXAMPLE 2

4-[4-Methyl-1,1,3-trioxo-7-(3-phenyl-prop-1-ynyl)-3,4-dihydro-1H-1l[6]-benzo[1,2,4]thiadiazin-2-ylmethyl]-benzoic acid

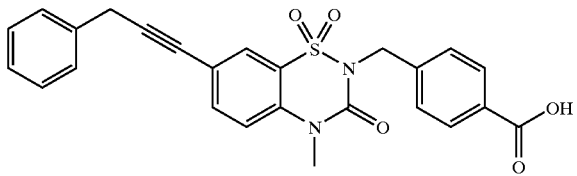

Step (1): 4-(7-Bromo-4-methyl-1,1,3-trioxo-3,4-dihydro-1H-1l[6]-benzo[1,2,4]thiadiazin-2-ylmethyl)-benzoic acid tert-butyl ester

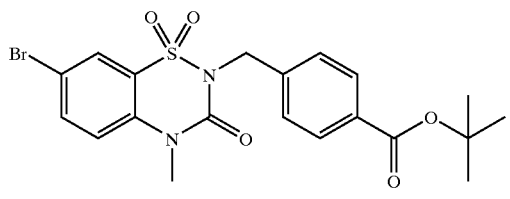

To a solution of 7-bromo-4-methyl-1,1-dioxo-1,4-dihydro-2H-1l[6]-benzo[1,2,4]thiadiazin-3-one (Example 1, Step (3), 2.00 g, 6.87 mmol) in 7 mL of dimethylformamide was added N,N-diisopropylethylamine (0.658 mL, 3.78 mmol). After stirring for 5 minutes, 4-bromomethyl-benzoic acid tert-butyl ester (1.02 g, 3.78 mmol) was added to the reaction mixture. After stirring at room temperature for 48 hours, the black solution was concentrated to give a brown oil. The product was purified by flash column chromatography on silica gel (20% ethyl acetate:hexanes) and triturated with diethyl ether to give 1.20 g (72.7%) of 4-(7-bromo-4-methyl-1,1,3-trioxo-3,4-dihydro-1H-1l[6]-benzo[1,2,4]thiadiazin-2-ylmethyl)-benzoic acid tert-butyl ester as a white solid: mp 120–122° C.; IR (KBr) 2989, 1688, 1590, 1480, 1351, 1163 cm$^{-1}$; $^1$HNMR (400 MHz, CDCl$_3$) δ 3.48 (s, 3H, NCH$_3$), 5.08 (s, 2H, NCH$_2$Ar), 7.12 (d, J=8.80 Hz, ArH), 7.47 (d, J=8.30 Hz, 2H, ArH), 7.76 (d, J=8.80, 2.20 Hz, 1H, ArH), 7.93 (d, J=8.30 Hz, 2H, ArH), 8.02 (d, J=2.4 Hz, 1H, ArH); MS(APCI+). Anal. Calcd for C$_{20}$H$_{21}$N$_2$O$_5$S$_1$Br$_1$: C, 49.8; H, 4.42; N, 5.82. Found: C, 49.90; H, 4.40; N, 5.82.

Step (2): 4-[4-Methyl-1,1,3-trioxo-7-(3-phenyl-prop-1-ynyl)-3,4-dihydro-1H-1l[6]-benzo[1,2,4]thiadiazin-2-ylmethyl]-benzoic acid tert-butyl ester

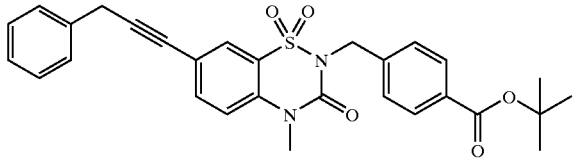

To a solution of CuI (0.002 g, 0.013 mmol) and Pd (PhCN)$_2$Cl$_2$ (0.007 g, 0.019 mmol), (after purging with nitrogen for 5 min) in 6 mL of anhydrous dioxane, was added P(t-Bu)$_3$ (0.008 g, 0.037 mmol), HN(i-Pr)$_2$ (0.262 mL, 1.87 mmol), 3-phenyl-1-propyne (0.230 mL, 1.87 mmol), and 4-(7-bromo-4-methyl-1,1,3-trioxo-3,4-dihydro-1H-1l[6]-benzo[1,2,4]thiadiazin-2-ylmethyl)-benzoic acid tert-butyl ester (Example 2, Step (1), 0.300 g, 0.623 mmol). Under a nitrogen atmosphere, the reaction mixture was stirred at room temperature for 24 hours. After the reaction was completed, ethyl acetate (20 mL) was added and white solids, (H$_2$N(I—Pr)$_2$Br) were filtered through celite. The filtrate was concentrated. The product was purified by flash column chromatography on silica gel (10% ethyl acetate:hexanes) and concentrated to give 0.200 g (62.1%) of 4-[4-methyl-1,1,3-trioxo-7-(3-phenyl-prop-1-ynyl)-3,4-dihydro-1H-1l[6]-benzo[1,2,4]thiadiazin-2-ylmethyl]-benzoic acid tert-butyl ester as a yellow gel: 1H NMR (400 MHz, CDCl$_3$) δ 1.99 (s, 3H, NCH$_3$), 3.79 (s, 2H, CCH$_2$Ar), 5.03 (s, 2H, NCH$_2$Ar), 7.12 (d, J=8.80 Hz, 1H, ArH), 7.22 (t, J=2.20 Hz, 1H, ArH), 7.24–7.36 (m, 4H, ArH), 7.41 (d, J=8.30 Hz, 2H, ArH), 7.63 (dd, J=8.70, 2.00, 1H, ArH), 7.87 (d, J=8.30 Hz, 2H, ArH), 7.92 (d, J=2.00, 1H, ArH); MS(APCI+): m/z 461.3 (MH$^+$).

Step (3): 4-[4-methyl-1,1,3-trioxo-7-(3-phenyl-prop-1-ynyl)-3,4-dihydro-1H-1l[6]-benzo[1,2,4]thiadiazin-2-ylmethyl]-benzoic acid

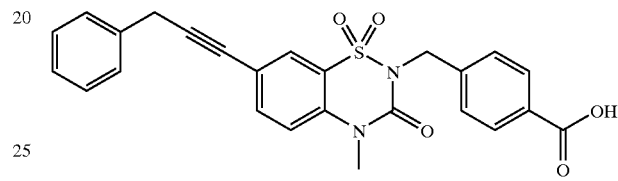

To a solution of 4-[4-methyl-1,1,3-trioxo-7-(3-phenyl-prop-1-ynyl)-3,4-dihydro-1H-1l[6]-benzo[1,2,4]thiadiazin-2-ylmethyl]-benzoic acid tert-butyl ester in 2 mL of CH$_2$Cl$_2$ was added 2 mL of trifluoroacetic acid. After stirring at room temperature for 24 hours, the reaction mixture was concentrated affording a yellow oil. Trituration with 10 mL of diethyl ether gave 0.040 g (88.8%) of 4-[4-methyl-1,1,3-trioxo-7-(3-phenyl-prop-1-ynyl)-3,4-dihydro-1H-1l[6]-benzo[1,2,4]thiadiazin-2-ylmethyl]-benzoic acid as a light yellow solid: mp 208–209° C.; $^1$H NMR (400 MHz, DMSO-d$_6$) δ 3.43 (s, 3H, NCH$_3$), 3.89 (s, 2H, CCH$_2$Ar), 5.00 (s, 2H, NCH$_2$Ar), 7.22 (t, J=7.32 Hz, 1H, ArH), 7.30–7.33 (m, 2H, ArH), 7.37–7.40 (m, 4H, ArH), 7.53 (d, J=8.79 Hz, 1H, ArH), 7.82–7.85 (m, 3H, ArH), 7.87 (d, J=8.30 Hz, 2H, ArH), 7.92 (d, J=2.00, 1H, ArH), 11.0 (s, 1H, OH); MS(APCI+): m/z 459.1 (MH$^-$).

EXAMPLE 3

2-Benzyl-1,1-dioxo-7-(3-phenyl-prop-1-ynyl)-1,4-dihydro-2H-1l[6]-benzo[1,2,4]thiadiazin-3-one Step (1): Synthesis of 7-iodo-1,1-dioxo-1,4-dihydro-2H-1l[6]benzo[1,2,4]thiadiazin-3-one The procedure of Example 2, Step (3) was followed, except that 4-iodoaniline was substituted for 4-methylaminobromobenzene, to provide 7-iodo-1,1-dioxo-1,4-dihydro-2H-1l[6]benzo[1,2,4]thiadiazin-3-one; $^1$H-NMR (DMSO-d$_6$); d 11.32 (s, 1H), 7.95 (d, 1H), 7.90 (dd, 1H), and 7.02 (d, 1H) ppm.

MS: M$^+$1=322.9 Da

Step (2): Synthesis of 2-benzyl-7-iodo-1,1-dioxo-1,4-dihydro-2H-1l[6]-benzo[1,2,4]thiadiazin-3-one 7-Iodo-1,1-dioxo-1,4-dihydro-2H-1l[6]benzo[1,2,4]thiadiazin-3-one (3.5 g, 10.8 mmoles) was mixed with 1.61 mL of 1,8-diazabicyclo[5.4.0]undec-7-ene in 100 mL of acetonitrile at room temperature. This was stirred for 30 minutes, and then 1.28 mL of benzyl bromide was added. The resulting mixture was stirred overnight. The reaction was concentrated in vacuo, and the residue was partitioned between 1M HCl and dichloromethane. The organic layer was dried (magnesium sulfate), filtered and concentrated to give a purple oil. Chromatography (silica gel, 30% ethyl acetate in hexanes) gave 1.02 g of 2-benzyl-7-iodo-1,1-dioxo-1,4-dihydro-2H-11[6]-benzo[1,2,4]thiadiazin-3-one; $^1$H-NMR (DMSO-d[6]); d 11.56 (s, 1H), 8.10 (d, 1H), 8.01 (dd, 1H), 7.29 (m, 5H), 7.07 (d, 1H), and 4.93 (s, 2H) ppm. MS: M[+]−1=413.0 Da Step (3): Synthesis of 2-benzyl-1,1-dioxo-7-(3-phenyl-prop-1-ynyl)-1,4-dihydro-2H-11[6]-benzo[1,2,4]thiadiazin-3-one 2-Benzyl-7-iodo-1,1-dioxo-1,4-dihydro-2H-11[6]-benzo[1,2,4]thiadiazin-3-one (0.42 g, 1 mmol) was mixed with 0.13 mL of 3-phenylpropyne in 25 mL of N,N-dimethylformamide at room temperature. Diisopropylethylamine (0.71 mL, 4.1 mmol) was added along with 0.04 g bis(triphenylphosphine)palladium (II)dichloride (5 mol %) and a catalytic amount of copper(I)iodide. The resulting mixture was heated to 50° C. for 3 hours, cooled to room temperature, and stirred overnight. The reaction was partitioned between 1M HCl and ethyl acetate. The organic layer was dried (magnesium sulfate), filtered, and concentrated to give a yellow oil. Chromatography (silica gel, 10% ethyl acetate/hexanes) gave 2-benzyl-1,1-dioxo-7-(3-phenyl-prop-1-ynyl)-1,4-dihydro-2H-11[6]-benzo[1,2,4]thiadiazin-3-one as a tan solid; $^1$H-NMR (CDCl[3]); d 9.39 (bs, 1H), 7.92 (s, 1H), 7.57 (dd, 1H), 7.35 (m, 10H), 6.87 (d, 1H), 5.06 (s, 2H), and 3.82 (s, 2H) ppm. MS: M[+]+1=403.1 Da

EXAMPLE 4

N-(4-Cyano-benzyl)-3-(3-[1,2,3]-triazol-1-yl-prop-1-ynyl)-benzamide

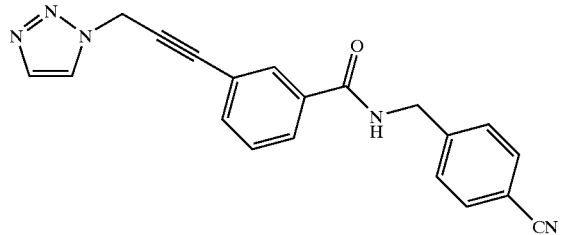

Step (1): N-(4-Cyano-benzyl)-3-iodo-benzamide

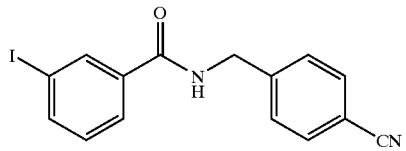

An aliquot of 3-iodobenzoyl chloride (1.1 g, 4.2 mmol) was taken up in tetrahydrofuran ("THF", 25 mL), and cooled to approximately 0° C. in an ice-water bath. To the cold solution were added 4-cyanobenzylamine hydrochloride (0.71 g, 4.2 mmol) and pyridine (0.66 g, 8.3 mmol). The solution gradually warmed to room temperature, and was stirred for 72 hours. The reaction mixture was diluted with ethyl acetate (25 mL) and aqueous HCl (25 mL). The organic phase was separated, dried (MgSO4), filtered, and rotary evaporated. The resulting crude product was purified using silica gel chromatography (elution with dichloromethane/THF [9:1]) to give N-(4-cyano-benzyl)-3-iodo-benzamide (0.76 g, 51%) as a white solid. $^1$H-NMR (DMSO-d[6]) δ 9.2 (t, 1H), 8.2 (s, 1H), 7.9 (m, 2H), 7.8 (d, 2H), 7.5 (d, 2H), 7.3 (m, 1H), 4.5 (d, 2H) ppm.

Step (2): N-(4-Cyano-benzyl)-3-([1,2,3]-triazol-1-yl-prop-1-ynyl)-benzamide

A solution of 1-propyn-3-yl-1H-[1,2,3]triazol (0.086 g, 0.8 mmol) in N,N-dimethylformamide ("DMF", 1 mL) was treated with the N-(4-cyano-benzyl)-3-iodo-benzamide (0.225 g, 0.62 mmol) prepared in Step (1), diisopropylethylamine (0.32 g, 2.5 mmol), copper (I) iodide (0.024 g, 0.013 mmol), and dichlorobis(triphenylphosphine)palladium (II) (0.025 g, 0.004 mmol), respectively. The reaction mixture was stirred under nitrogen atmosphere for 5 hours at 55° C., then cooled to room temperature. The crude reaction mixture was diluted with THF (5 mL) and passed through a pad of silica gel (elution with THF). The partially purified product obtained was further purified using silica gel chromatography (elution with THF/hexane [3:1]) to give the title compound (0.077 g, 36%) as cream color solid. $^1$H-NMR (CDCl[3]/DMSO-d[6]) δ 8.3 (m, 1H), 7.9 (s, 1H), 7.8 (m, 2H), 7.6 (s, 1H), 7.4 (m, 3H), 7.3 (m, 2H), 5.3 (s, 2H), 4.5 (d, 2H) ppm. Mp 145° C.–147° C.

EXAMPLE 5

N-(4-Cyano-benzyl)-3-(3-[1,2,4]-triazol-1-yl-prop-1-ynyl)-benzamide.

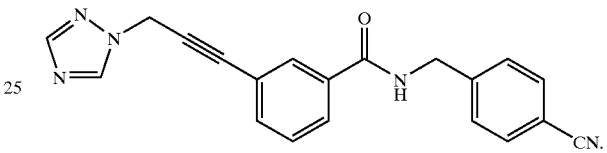

Replacing the 1-propyn-3-yl-1H-[1,2,3]triazole in Example 4, Step (2) with 1-propyn-3-yl-1H-[1,2,4]triazole yielded N-(4-cyano-benzyl)-3-(3-[1,2,3]-trizol-1-yl-prop-1-ynyl)-benzamide; $^1$H-NMR (CDCl[3]/DMSO-d[6]) δ 8.6 (s, 1H), 8.2 (t, 1H), 8.0 (s, 1H), 7.9 (s, 1H), 7.8 (m, 1H), 7.5 (m, 3H), 7.4 (m, 3H), 5.1 (s, 2H), 4.6 (d, 2H) ppm. Mp 183–186° C.

EXAMPLE 6

4-{[3-(3-Phenethylethynyl-benzoylamino]-methyl}-benzoic acid

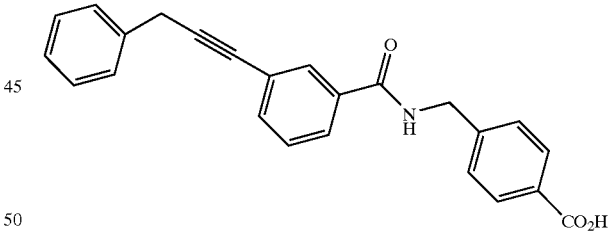

Replacing 4-cyanobenzylamine hydrochloride in Example 4, Step (1), with 4-carboxy-benzylamine hydrochloride, and replacing the 1-propyn-3-yl-1H-[1,2,3] triazole in Example 4, Step (2), with 3-phenyl-propyne yielded 4-[[3-3-phenethylethynyl-benzoylamino]-methyl}-benzoic acid; $^1$H-NMR (DMSO-d[6]) δ 9.2 (m, 1H), 8.0 (s, 1H), 7.8 (m, 4H), 7.6 (d, 1H) 7.2–7.4 (m, 7H), 4.5 (d, 2H), 3.9 (s, 2H) ppm. Mp 209° C.–211° C.

By replacing the 4-cyanobenzylamine hydrochloride in Example 4, Step (1), with appropriately substituted amines and by substituting for 1-propyn-3-yl-1H-[1,2,3]triazole in Example 4, Step (2), with appropriately substituted alkynes, and by using the experimental conditions outlined in Example 4, Steps (1) and (2), respectively, the compounds of Examples 7 to 12 can be synthesized.

EXAMPLE 7

4-({3-[3-(4-Chloro-phenyl)-prop-1-ynyl]-benzoylamino}-methyl)-benzoic acid

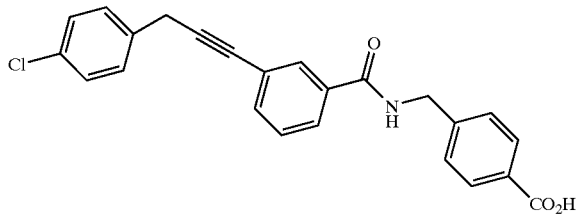

EXAMPLE 8

4-({3-[3-(4-Fluoro-phenyl)-prop-1-ynyl]-benzoylamino}-methyl)-benzoic acid

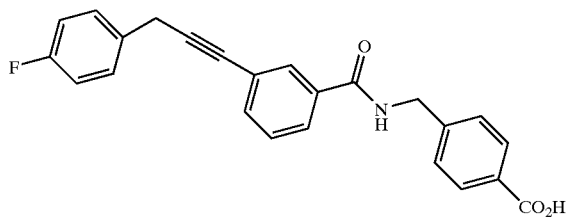

EXAMPLE 9

3-Phenylethynyl-N-(4-Sulfamoyl-benzyl)-benzamide

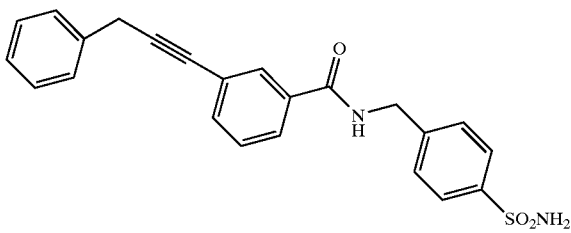

EXAMPLE 10

N-(4-Cyano-benzyl)-3-phenylethynyl-benzamide

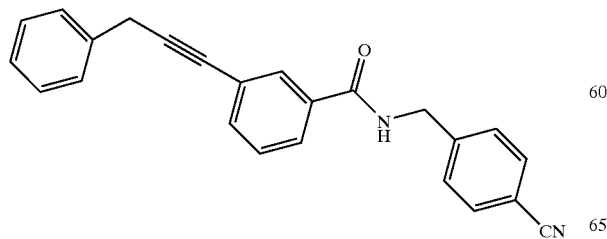

EXAMPLE 11

3-Phenethlethynyl-N-pyridin-4-yl-methyl-benzamide

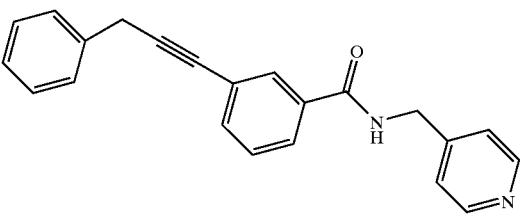

EXAMPLE 12

3-[3-(3-Phenethylethynyl-benzoylamino)-methyl]-benzoic acid

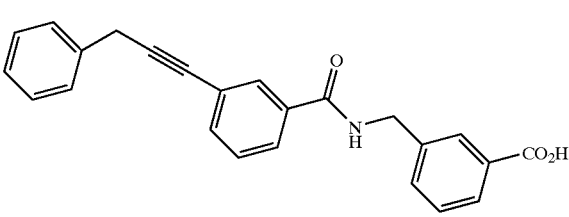

Replacement of 3-iodobenzoyl chloride in Example 4, Step (1), with the appropriately substituted pyridine analog, and using the experimental conditions outlined in Example 4, Steps (1) and (2), the compounds of Examples 13 and 14 can be synthesized.

EXAMPLE 13

4-({[5-(3-Phenyl-prop-1-ynyl)-pyridine-3-carbonyl]-amino}-methyl)-benzoic acid

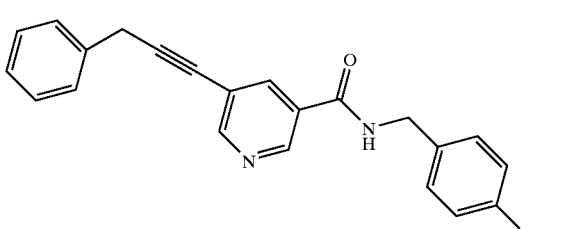

EXAMPLE 14

4-{[(Phenylethynyl-pyridine-2-carbonyl)-amino]-methyl}-benzoic acid

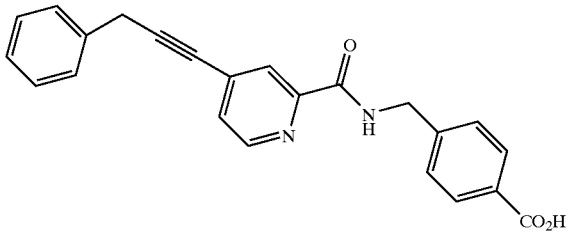

EXAMPLE 15

4-[1-Methyl-2,4-dioxo-6-(3-phenyl-prop-1-ynyl)-1,4-dihydro-2H-2λ⁴-benzo[1,2,6]thiadiazin-3-yl methyl]benzoic acid Step (1): Synthesis of 5-Iodo-2-methlaminobenzoic acid

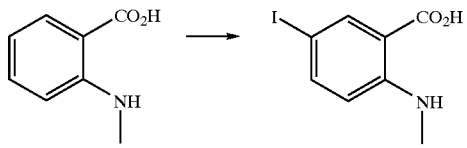

A suspension of N-methylanthranilic acid (10.00 g, 66.2 mmol) in glacial acetic acid (60 mL) was stirred at room temperature for 20 minutes, then treated with water (120 mL). To this was added iodine (16.80 g, 66.2 mmol) in portions, and the reaction mixture was stirred vigorously for 5 days. The resulting solid was collected by filtration, washed with water, and allowed to air dry under house vacuum. Drying afforded 9.64 g of 5-iodo-2-methylaminobenzioc acid as green/brown solid (52.6% yield). $^1$H-NMR (DMSO-$d_6$); d 7.95 (s, 1H), 7.58–7.56 (d, 1H), 6.52–6.50 (d, 1H), 2.78 (s, 3H). MS: M$^+$+1=277.9 Da Step (2): Synthesis of 4-[5-iodo-2-methylaminobenzoylamino)methyl]benzoic acid tert-butyl ester

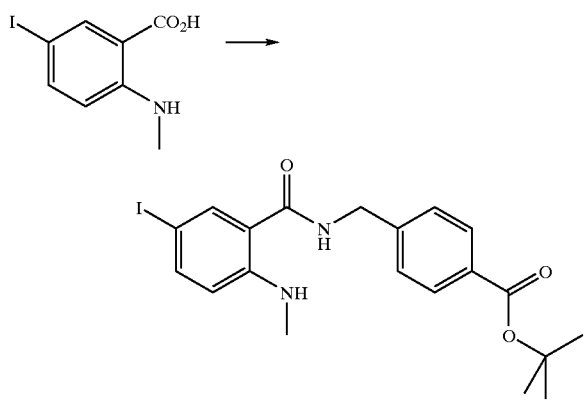

A solution of 5-iodo-2-methylaminobenzoic acid (1.50 g, 5.4 mmol) in DMF (8 mL) was treated with 4-aminomethylbenzoic acid tert-butyl ester (1.25 g, 6.50 mmol), 1-[3-(dimethylamino)propyl]-3-ethylcarbodiimide hydrochloride ("EDAC.HCl") (1.24 g, 6.50 mmol), 1-hydroxybenzotriazole hydrate (0.88 g, 6.50 mmol), and the reaction mixture was stirred overnight at room temperature. The resulting solution was treated with water (15 mL), followed by saturated aqueous sodium bicarbonate (4 mL), then water (15 mL), and the mixture was stirred for 30 minutes. The aqueous/DMF layer was decanted from the resulting black gum, and the gum was washed with water. The aqueous was decanted, and the resulting material was dissolved in ethyl acetate, washed with brine, dried over MgSO$_4$ and evaporated onto silica gel.

The residue was purified on a 4.5×18 cm silica gel column eluted with hexane/ethyl acetate 4:1. Evaporation and drying afforded 2.10 g of 4-[5-iodo-2-methylaminobenzoylamino)methyl]benzoic acid tert-butyl ester as a yellow foam (83.2% yield). $^1$H-NMR (CDCl$_3$); d 7.97–7.94 (m, 2H), 7.56–7.50 (m, 2H), 7.36–7.35 (d, 2H), 6.47–6.44 (d, 1H), 6.33 (bs, 1H), 4.60–4.59 (d, 2H), 2.82 (s, 1.57 (S, 9H). MS: M$^+$+1=467.0 Da Step (3): Synthesis of 4-[6-iodo-1-methyl-2,4-dioxo-1,4-dihydro-2H-2λ⁴-benzol[1,2,6]thiadiazin-3yl methyl)benzoic acid tert-butyl ester

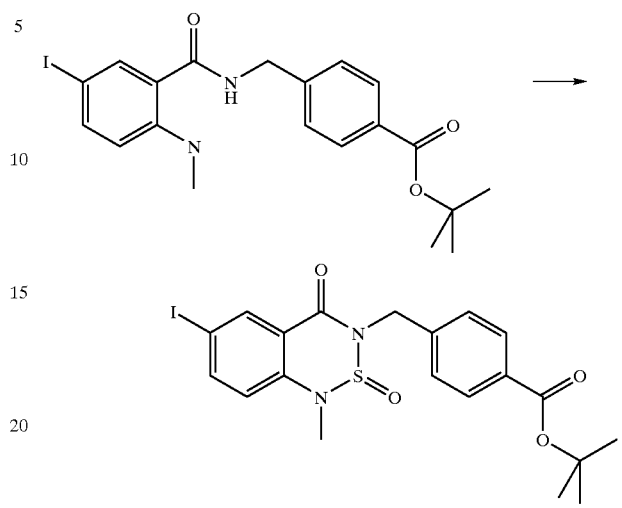

A solution of 4-[5-iodo-2-methylaminobenzoylamino)methyl]benzoic acid tert-butyl ester (1.73 g, 3.71 mmol) in benzene (60 mL) was treated with thionyl chloride (0.30 mL, 4.08 mmol), then heated to reflux for 3 hours. The solution was diluted with benzene, washed with brine, dried over MgSO$_4$, and evaporated to dryness. The residue was crystallized from hexane/ethyl acetate, and the crystals allowed to air dry under house vacuum overnight. This afforded 4-[6-iodo-1-methyl-2,4-dioxo-1,4-dihydro-2H-2λ⁴-benzo[1,2,6]thiadiazin-3ylmethyl)benzoic acid tert-butyl ester as 1.64 g of yellow crystals (86.3% yield). $^1$H-NMR (CDCl$_3$); d 8.50 (d, 1H), 7.97–7.96 (d, 2H), 7.94 (d, 1H), 7.41–7.38 (d, 2H), 6.78–6.75 (d, 1H), 5.41–5.37 (d, 1H), 4.75–4.71 (d, 1H), 3.36 (s, 3H), 1.56 (s, 9H). MS: M$^+$+1=512.9 Da Step (4): Synthesis of 4-[1-methyl-2,4-dioxo-6-(3-phenyl-prop-1-ynyl)-1,4-dihydro-2H-2λ⁴-benzo[1,2,6]thiadiazin-3yl methyl]benzoic acid tert-butyl ester

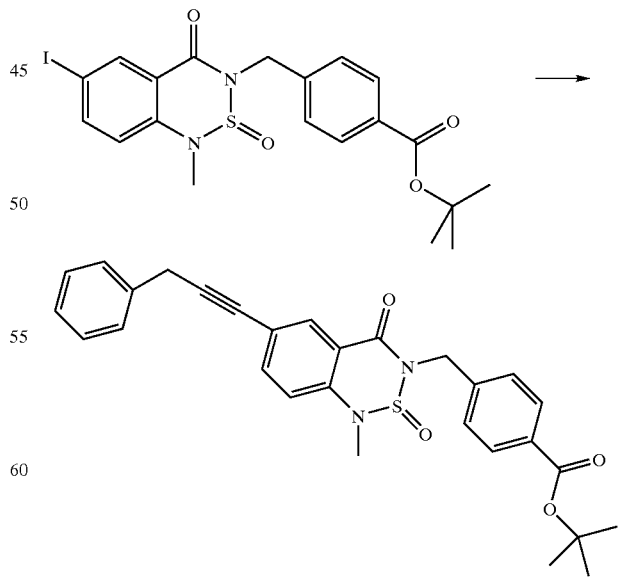

A solution of 4-[6-iodo-1-methyl-2,4-dioxo-1,4-dihydro-2H-2λ⁴-benzol[1,2,6]thiadiazin-3yl methyl)benzoic acid tert-butyl ester (0.50 g, 0.98 mmol) in DMF (9 mL) in a screw cap vial was degassed with nitrogen, then treated with triethylamine (0.56 mL, 4.0 mmol), CuI (0.013 g, 0.07 mmol), Pd(Ph₃P)₄ (0.048 g, 0.042 mmol), and 3-phenyl-1-propyne (0.29 mL, 2.3 mmol). The reaction mixture was heated in an oil bath at 65° C. for 3 hours, cooled to room temperature, the DMF was evaporated, and the residue dissolved in ethyl acetate. The organic portion was washed with 1N HCl, brine, dried over MgSO₄, and evaporated onto silica gel The silica gel mesh was purified on a 3.5×18 cm silica gel column eluted with hexane/ethyl acetate 4:1, followed by hexane/ethyl acetate 2:1. Drying under high vacuum afforded the product as 0.42 g of yellow foam (86.0% yield). $^1$H-NMR (CDCl₃); d 8.29 (d, 1H), 7.96–7.94 (m, 2H), 7.68 (d, 1H), 7.42–7.34 (m, 6H), 7.27–7.24 (m, 1H), 6.94–6.92 (d, 1H), 4.76–4.72 (d, 1H), 3.82 (s, 2H), 3.38 (s, 3H), 1.57 (s, 9H). MS: M⁺(-OtBu)+1=445.1 Da Step (5): Synthesis of 4-[1-methyl-2,4-dioxo-6-(3-phenyl-prop-1-ynyl)-1,4-dihydro-2H-2λ⁴-benzo[1,2,6]thiadiazin-3-yl methyl]benzoic acid

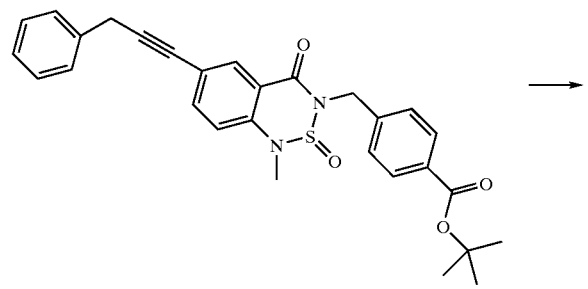

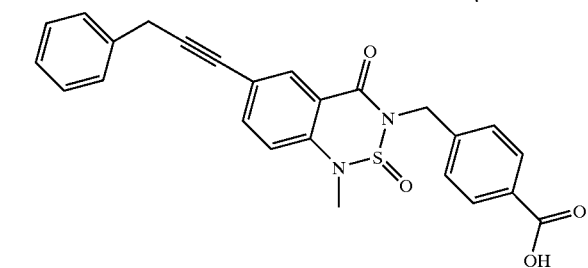

A solution of 4-[1-methyl-2,4-dioxo-6-(3-phenyl-prop-1-ynyl)-1,4-dihydro-2H-2λ⁴-benzo[1,2,6]thiadiazin-3-yl methyl]benzoic acid tert-butyl ester (0.33 g, 0.66 mmol) in methylene chloride (10 mL) was treated with trifluoroacetic acid (3 mL), and stirred at room temperature for 1 hour. The reaction mixture was evaporated to dryness, treated with hot ethyl acetate, allowed to cool, and the solid collected by filtration. The solid was triturated with ethyl ether, the solid collected by filtration, and allowed to air dry under house vacuum. The process afforded 0.03 g of 4-[1-methyl-2,4-dioxo-6-(3-phenyl-prop-1-ynyl)-1,4-dihydro-2H-2λ⁴-benzo[1,2,6]thiadiazin-3-yl methyl]benzoic acid as a blue/green solid (9.5% yield). $^1$H-NMR (CDCl₃); d 8.30 (d, 1H), 8.08–8.06 (d, 2H), 7.69–7.67 (dd, 1H), 7.48–7.46 (d, 2H), 7.40–7.32 (m, 4H), 7.27–7.23 (m, 1H), 6.97–6.95 (d, 1H), 5.44–5.40 (d, 1H), 4.81–4.77 (d, 1H), 3.83 (s, 2H), 3.41 (s, 3H). MS: M⁺+1=445.1 Da

EXAMPLE 16

4-[1-methyl-2,2,4-trioxo-6-(3-phenylprop-1-ynyl)-1,4-dihydro-2H-2λ⁶-benzo[1,2,6]-thiadiazin-3-ylmethyl] benzoic acid Step (1): Synthesis of 4-[6-iodo-1-methyl-2,2,4-trioxo-1,4-dihydro-2H-2λ⁴-benzo[1,2,6]-thiadiazin-3yl methyl) benzoic acid tert-butyl ester

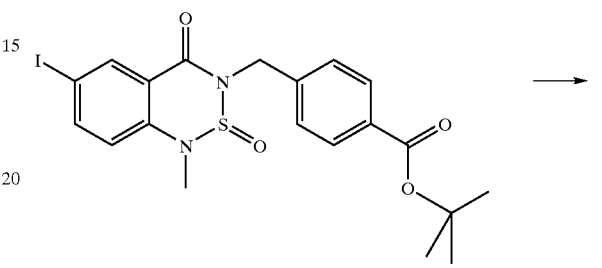

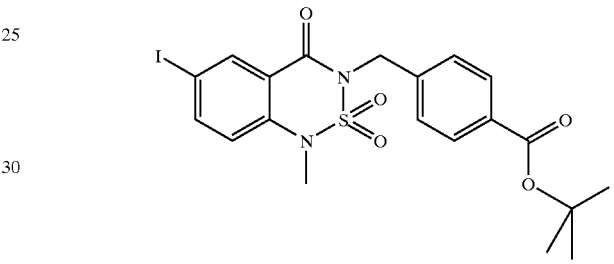

A suspension of 4-[6-iodo-1-methyl-2,2,4-trioxo-1,4-dihydro-2H-2λ⁴-benzo[1,2,6]-thiadiazin-3yl methyl) benzoic acid tert-butyl ester (0.60 g, 1.17 mmol) in ethyl acetate (5 mL) was treated with an aqueous solution of >4% NaOCl (7.0 g), followed by tetrabutylammonium bromide, and the reaction mixture stirred at room temperature overnight. The reaction mixture was diluted with water, extracted with ethyl acetate, the organic portion washed with brine, dried over MgSO₄, and evaporated to dryness to give 0.61 g of white foam (98.6% yield). $^1$H-NMR (CDCl₃); d 8.47–8.46 (d, 1H), 7.95–7.91 (m, 3H), 7.00–6.97 (d, 1H), 5.21 (s, 2H), 3.30 (s, 3H), 1.55 (s, 9H). MS: M⁺(—O-tBu)+1=472.9 Da Step (2): Synthesis of 4-[1-methyl-2,2,4-trioxo-6-(3-phenylprop-1-ynyl)-1,4-dihydro-2H-2λ⁶-benzo[1,2,6]-thiadiazin-3-ylmethyl]benzoic acid tert-butyl ester

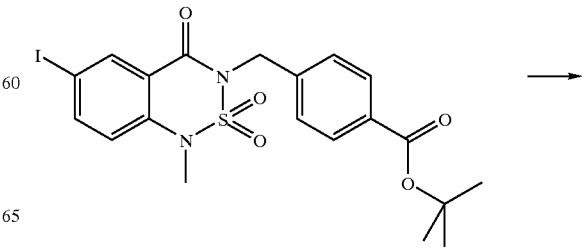

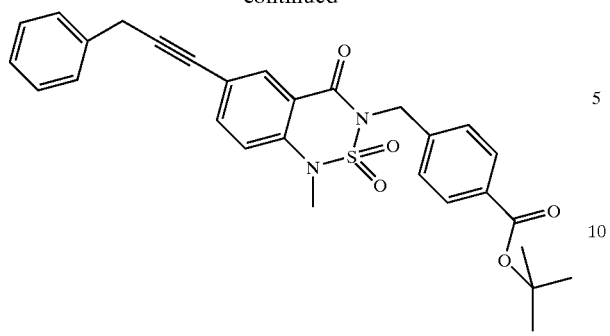

The coupling of 4-[1-methyl-2,2,4-trioxo-6-(3-phenylprop-1-ynyl)-1,4-dihydro-2H-2λ⁶-benzo[1,2,6]-thiadiazin-3-ylmethyl]benzoic acid tert-butyl ester (0.60 g, 1.13 mmol) with 3-phenyl-1-propyne (0.33 mL, 2.65 mmol) using triethylamine (0.64 mL, 4.51 mmol), CuI (0.015 g, 0.08 mmol), and Pd(Ph₃P)₄ (0.055 g, 0.047 mmol) was carried out as described in Example 15, Step (4). Purification on a silica gel column eluted with hexane/ethyl acetate 4:1, followed by drying, afforded 0.10 g of 4-[1-methyl-2,2,4-trioxo-6-(3-phenylprop-1-ynyl)-1,4-dihydro-2H-2λ⁶-benzo[1,2,6]-thiadiazin-3-ylmethyl]benzoic acid tert-butyl ester as a white foam (17.0% yield). ¹H-NMR (CDCl₃); d 8.23–8.22 (d, 1H), 9.95–7.93 (d, 2H), 7.68 (d, 1H), 7.51–7.49 (d, 2H), 7.38–7.30 (m, 3H), 7.27–7.23 (m, 1H), 7.17–7.16 (d, 2H), 5.13 (s, 2H), 3.82 (s, 2H), 3.32 (s, 3H), 1.55 (s, 9H). MS: M⁺(—O-tBu)+1=461.1 Da Step (3): Synthesis of 4-[1-methyl-2,2,4-trioxo-6-(3-phenylprop-1-ynyl)-1,4-dihydro-2H-2λ⁶-benzo[1,2,6]-thiadiazin-3-ylmethyl]benzoic acid

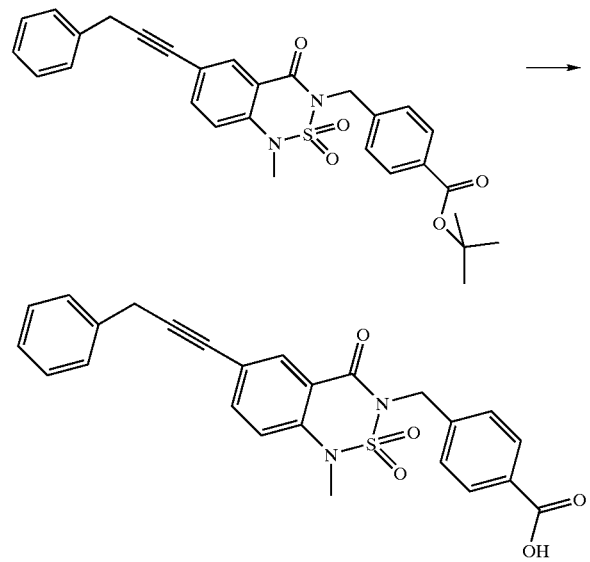

A solution of 4-[1-methyl-2,2,4-trioxo-6-(3-phenylprop-1-ynyl)-1,4-dihydro-2H-2λ⁶-benzo[1,2,6]-thiadiazin-3-ylmethyl]benzoic acid tert-butyl ester (0.075 g, 0.15 mmol) was treated with trifluoroacetic acid (5 mL), and the reaction mixture stirred at room temperature for 30 minutes. The solution was evaporated to dryness, the residue dissolved in ethyl acetate, washed with water, brine, and dried over MgSO₄, and evaporated. Trituration with ethyl ether afforded a solid that was collected by filtration, washed with ethyl ether, and allowed to air dry under hose vacuum overnight. This afforded 0.015 g of 4-[1-methyl-2,2,4-trioxo-6-(3-phenylprop-1-ynyl)-1,4-dihydro-2H-2λ⁶-benzo[1,2,6]-thiadiazin-3-ylmethyl]benzoic acid as a light yellow solid (23.2% yield). ¹H-NMR (CDCl₃); d 8.24 (d, 1H), 8.08–8.05 (d, 2H), 7.69–7.66 (dd, 1H), 7.57–7.55 (d, 2H), 7.38–7.31 (m, 4H), 7.27–7.23 (m, 1H), 7.18–7.16 (d, 1H), 5.16 (s, 2H), 3.34 (s, 3H). MS: M⁺+1=461.1 Da

EXAMPLE 17

4-[1,1,3-Trioxo-7-(3-phenyl-prop-1-ynyl)-3,4-dihydro-1H-1λ⁶-benzo[1,2,4]thiadiazin-2-ylmethyl]-benzoic acid Step (1): Synthesis of 4-[(2-Nitro-benzenesulfonylamino)-methyl]-benzoic acid tert-butyl ester

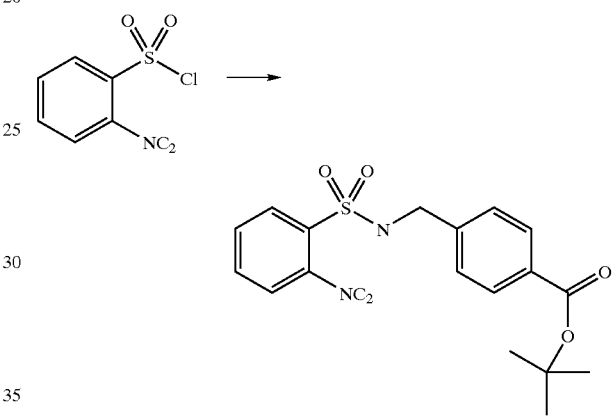

2-Nitro-benzenesulfonyl chloride (8.55 g, 38.6 mmol) and 4-aminomethyl-benzoic acid tert-butyl ester (8.0 g, 38.6 mmol) were mixed in 400 mL of dichloromethane. Triethylamine (10.8 mL, 77.2 mmol) was added, and the resulting mixture was stirred at room temperature for 16 hours. The reaction was partitioned between 1M HCl and dichloromethane. The organic layer was dried (magnesium sulfate), filtered, and rotary evaporated to give 14.46 g (95%) of 4-[(2-nitro-benzenesulfonylamino)-methyl]-benzoic acid tert-butyl ester as an off-white solid. ¹H-NMR (CDCl₃); δ 8.00 (dd, 1H), 7.84 (m, 3H), 7.67 (m, 2H), 7.27 (dd, 2H), 5.76 (bt, 1H), 4.36 (d, 2H), and 1.57 (s, 9H). MS: M⁺=392.1 Da Step (2): Synthesis of 4-[(2-Amino-benzenesulfonylamino)-methyl]-benzoic acid tert-butyl ester

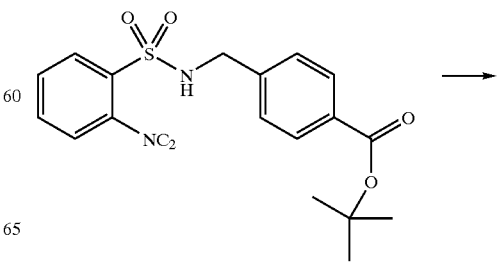

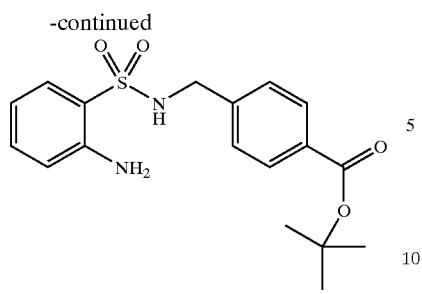

4-[(2-Nitro-benzenesulfonylamino)-methyl]-benzoic acid tert-butyl ester (14.4 g, 40 mmol) was dissolved in 100 mL of tetrahydrofuran containing 10 g of Raney Nickel. The reaction was pressurized with 100 psi of hydrogen gas and stirred for 28 hours at 25° C. to 60° C. The reaction was filtered, and the filtrate was rotary evaporated to give a thick oil. Chromatography (20% ethyl acetate/hexanes, SiO$_2$) of the oil gave 12.2 (92%) of 4-[(2-Amino-benzenesulfonylamino)-methyl]-benzoic acid tert-butyl ester as a clear oil. $^1$H-NMR (CDCl$_3$); δ 7.85 (d, 2H), 7.70 (dd, 1H), 7.27 (m, 3H), 6.78 (m, 2H), 5.18 (bt, 1H), 4.82 (bs, 2H), 4.08 (d, 2H), and 1.57 (s, 9H). MS: M$^+$=363.1 Da Step (3): Synthesis of 4-[(2-Amino-5-bromo-benzenesulfonylamino)-methyl]-benzoic acid tert-butyl ester

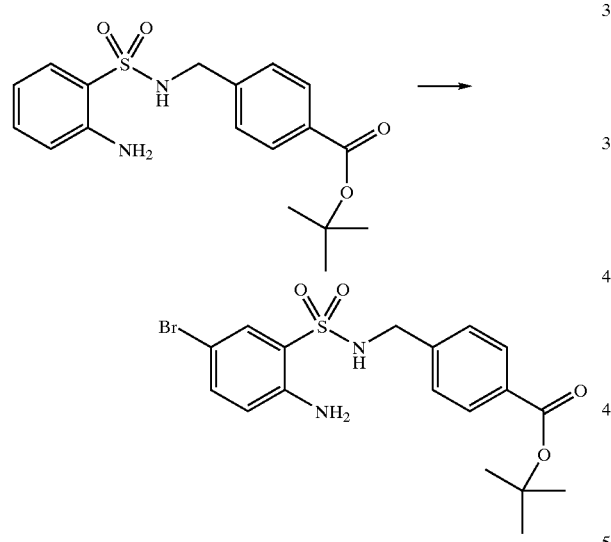

4-[(2-Amino-benzenesulfonylamino)-methyl]-benzoic acid tert-butyl ester (12.16 g, 33.5 mmol) was dissolved in 150 mL of acetic acid at 10° C. A solution of bromine (2.06 mL, 40.2 mmol) in 50 mL acetic acid was added dropwise. After complete addition, a thick yellow precipitate was observed. The reaction was filtered, and the solid washed with water. Chromatography of the solid (20% ethyl acetate/hexanes, SiO$_2$) gave 5.72 g (39%) of 4-[(2-Amino-5-bromo-benzenesulfonylamino)-methyl]-benzoic acid tert-butyl ester as a white solid. $^1$H-NMR (CDCl$_3$); 7.86 (d, 2H), 7.74 (d, 1H), 7.37 (dd, 1H), 7.23 (m, 2H), 6.65 (d, 1H), 5.19 (bt, 1H), 4.14 (d, 2H), and 1.58 (s, 9H). MS: M$^+$=441.0 Da Step (4): Synthesis of 4-(7-Bromo-1,1,3-trioxo-3,4-dihydro-1H-1λ$^6$-benzo[1,2,4]thiadiazin-2-ylmethyl)-benzoic acid tert-butyl ester

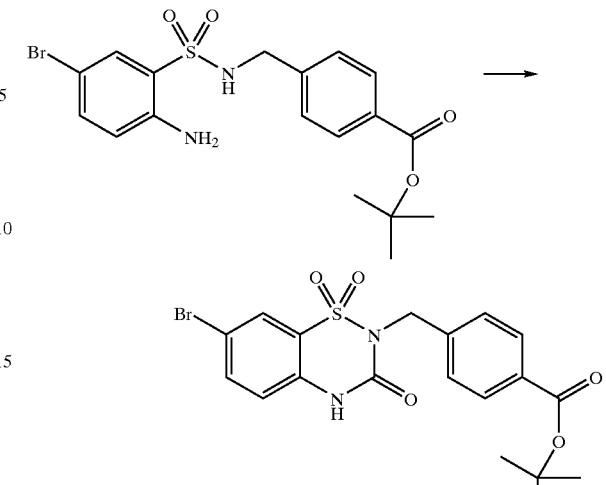

4-[(2-Amino-5-bromo-benzenesulfonylamino)-methyl]-benzoic acid tert-butyl ester. (3.72 g, 8.4 mmol) was dissolved in 150 mL of tetrahydrofuran. Bis(trichloromethyl)carbonate (2.75 g, 9.3 mmol) was added followed by 0.8 mL (8.4 mmol) of pyridine. The resulting suspension was stirred for 16 hours at room temperature. The reaction was then partitioned between 1M HCl and ethyl acetate. The organic layer was dried (magnesium sulfate), filtered, and concentrated to give an oily solid. Chromatography (20% ethyl acetate/hexanes, SiO$_2$) gave 3.7 g (94%) of 4-(7-bromo-1,1,3-trioxo-3,4-dihydro-1H-1λ$_6$-benzo[1,2,4]thiadiazin-2-ylmethyl)-benzoic acid tert-butyl ester as a white solid. $^1$H-NMR (CDCl$_3$); δ 9.49 (s, 1H), 7.94 (m, 3H), 7.64 (dd, 1H), 7.46 (d, 2H), 6.79 (d, 1H), 5.08 (s, 2H), and 1.55 (s, 9H). MS: M$^+$=466.9 Da Step (5): Synthesis of 4-[1,1,3-Trioxo-7-(3-phenyl-prop-1-ynyl)-3,4-dihydro-1H-1λ$^6$-benzo[1,2,4]thiadiazin-2-ylmethyl]-benzoic acid tert-butyl ester

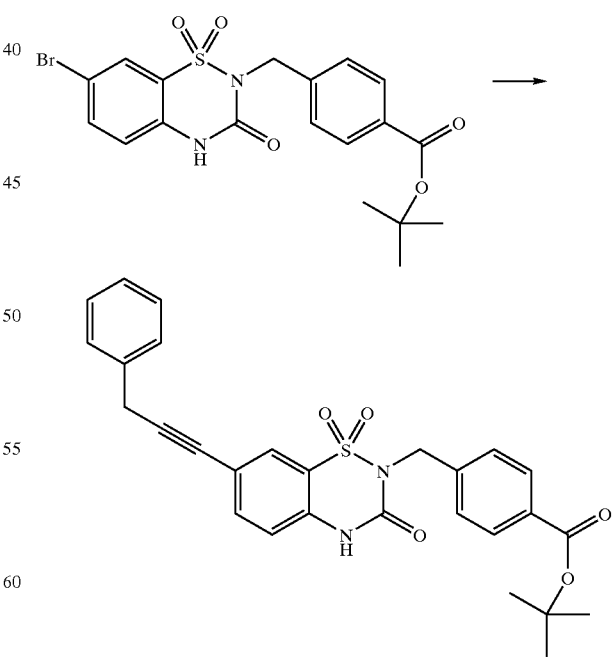

When the procedure of Example 4, Step (4) 4-[6-iodo-1-methyl-2,4-dioxo-1,4-dihydro-2H-2λ$^4$-benzo[1,2,6]thiadiazin-3yl methyl)benzoic acid tert-butyl ester was replaced with 4-(7-bromo-1,1,3-trioxo-3,4-dihydro-1H-1λ⁶-benzo[1,2,4]thiadiazin-2-ylmethyl)-benzoic acid tert-butyl ester (0.38 g, 0.81 mmol), 0.18 g (44%) of 4-[1,1,3-trioxo-7-(3-phenyl-prop-1-ynyl)-3,4-dihydro-1H-1λ⁶-benzo[1,2,4]thiadiazin-2-ylmethyl]-benzoic acid tert-butyl ester was obtained as an off-white solid. ¹H-NMR (CDCl₃); δ 8.99 (s, 1H), 7.92 (m, 3H), 7.57 (dd, 1H), 7.47 (d, 2H), 7.34 (m, 3H), 7.26 (m, 2H), 6.82 (d, 1H), 5.08 (s, 2H), 3.81 (s, 2H), and 1.54 (s, 9H). MS: M⁺−1=501.1 Da Step (6): Synthesis of 4-[1,1,3-Trioxo-7-(3-phenyl-prop-1-ynyl)-3,4-dihydro-1H-1λ⁶-benzo[1,2,4]thiadiazin-2-ylmethyl]-benzoic acid

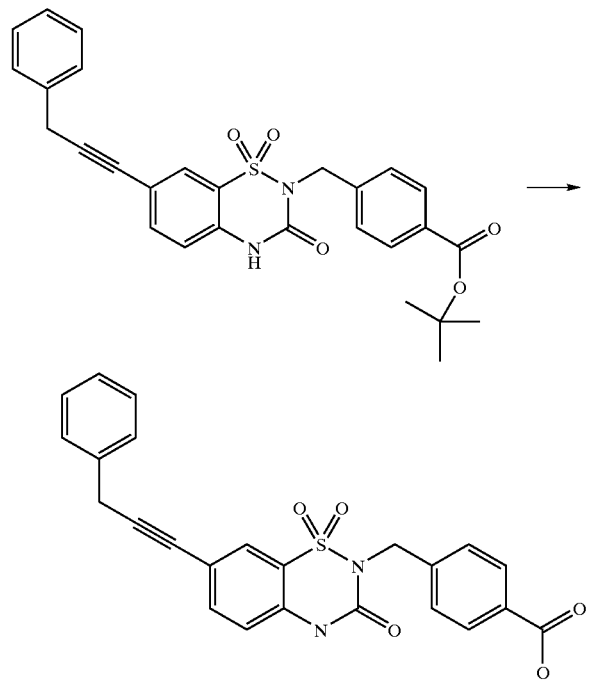

When in the procedure of Example 4, Step (5) 4-[1-methyl-2,4-dioxo-6-(3-phenyl-prop-1-ynyl)-1,4-dihydro-2H-2λ⁴-benzo[1,2,6]thiadiazin-3-ylmethyl]benzoic acid tert-butyl ester was replaced with 4-[1,1,3-trioxo-7-(3-phenyl-prop-1-ynyl)-3,4-dihydro-1H-1λ⁶-benzo[1,2,4]thiadiazin-2-ylmethyl]-benzoic acid tert-butyl ester (0.12 g, 0.24 mmol) to give 0.9 g (84%) of 4-[1,1,3-trioxo-7-(3-phenyl-prop-1-ynyl)-3,4-dihydro-1H-1λ⁶-benzo[1,2,4]thiadiazin-2-ylmethyl]-benzoic acid as a white solid. ¹H-NMR (CDCl₃); 11.00 (s, 1H), 7.85 (d, 2H), 7.74 (s, 1H), 7.43 (d, 1H), 7.35 (d, 2H), 7.16 (m, 6H), 4.94 (s, 2H), and 3.70 (s, 2H). MS: M⁺+1=447.0 Da

EXAMPLE 18

2-(4-Methoxy-benzyl)-1,1-dioxo-7-(3-phenyl-prop-1-ynyl)-1,4-dihydro-2H, 1λ⁶-benzo[1,2,4]thiadiazin-3-one Step (1): Synthesis of N-(4-Methoxy-benzyl)-2-nitro-benzenesulfonamide

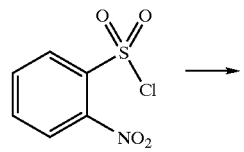

-continued

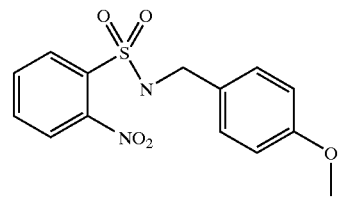

When in the procedure of Example 17, Step (1), 4-aminomethyl-benzoic acid tert-butyl ester was replaced with 4-methoxybenzlamine, the title compound N-(4-methoxy-benzyl)-2-nitro-benzenesulfonamide was obtained as a yellow solid. ¹H-NMR (CDCl₃); δ 7.99 (dd, 1H), 7.80 (dd, 2H), 7.65 (m, 2H), 7.10 (d, 2H) 6.73 (d, 2H), 5.62 (bt, 1H), 4.23 (d, 2H), and 3.74 (s, 3H). MS: M⁺=322.0 Da Step (2): Synthesis of 2-Amino-N-(4-methoxy-benzyl)-benzenesulfonamide

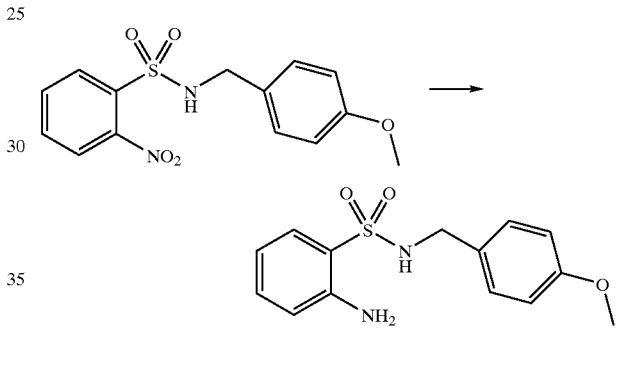

When in the procedure of Example 17, Step (2), 4-[(2-nitro-benzenesulfonylamino)-methyl]-benzoic acid tert-butyl ester was replaced with N-(4-methoxy-benzyl)-2-nitro-benzenesulfonamide, the title compound 2-amino-N-(4-methoxy-benzyl)-benzenesulfonamide was obtained as a thick oil. ¹H-NMR (CDCl₃); δ 7.71 (dd, 1H), 7.07 (d, 2H), 6.78 (m, 4H), 4.93 (bt, 1H), 4.82 (bs, 2H), 3.95 (d, 2H), and 3.75 (s, 3H). MS: M⁺−1=291.0 Da Step (3): Synthesis of 2-Amino-5-bromo-N-(4-methoxy-benzyl)-benzenesulfonamide

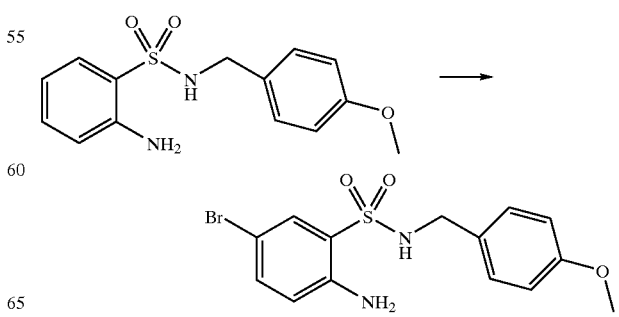

When in the procedure of Example 17, Step (3) 4-[(2-amino-benzenesulfonylamino)-benzoic acid tert-butyl ester was replaced with 2-amino-N-(4-methoxy-benzyl)-benzenesulfonamide, the title compound 2-amino-5-bromo-N-(4-methoxy-benzyl)-benzenesulfonamide was obtained as a clear oil.

$^1$H-NMR (CDCl$_3$); δ 7.75 (s, 1H), 7.36 (d, 1H), 7.07 (d, 2H), 6.77 (d, 2H), 6.62 (d, 1H), 5.03 (bt, 1H), 4.85 (bs, 2H), 4.01 (d, 2H), and 3.76 (s, 3H). MS: M$^+$=371.0 Da Step (4): Synthesis of 7-Bromo-2-(4-methoxy-benzyl)-1,1-dioxo-1,4-dihydro-2H-1λ$^6$-benzo[1,2,4]thiadiazin-3-one

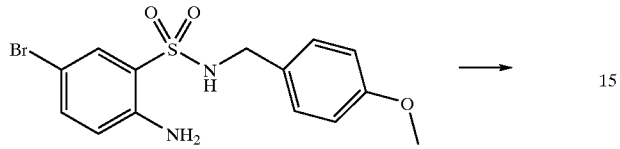

When the procedure of Example 17, Step (4) 4-[(2-Amino-5-bromo-benzenesulfonylamino)-methyl]-benzoic acid tert-butyl ester was replaced with 2-amino-N-(4-methoxy-benzyl)-benzenesulfonamide, the title compound 7-bromo-2-(4-methoxy-benzyl)-1,1-dioxo-1,4-dihydro-2H-1λ$^6$-benzo[1,2,4]thiadiazin-3-one was obtained as an off-white solid. $^1$H-NMR (CDCl$_3$); δ 10.94 (s, 1H), 7.77 (s, 1H), 7.48 (dd, 1H), 7.27 (m, 2H), 7.03 (d, 1H), 6.71 (d, 2H), 4.86 (s, 2H), and 3.66 (s, 3H). MS: M$^+$=396.96 Da Step (5): Synthesis of 2-(4-Methoxy-benzyl)-1,1-dioxo-7-(3-phenyl-prop-1-ynyl)-1,4-dihydro-2H-1λ$^6$-benzo[1,2,4]thiadiazin-3-one

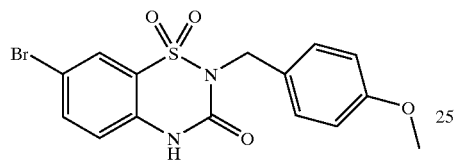

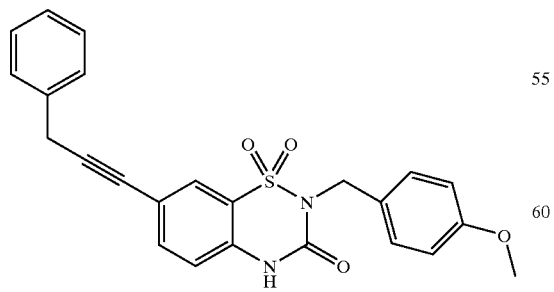

When in the procedure of Example 15, Step (4), 4-[6-iodo-1-methyl-2,4-dioxo-1,4-dihydro-2H-2λ$^4$-benzo[1,2,6] thiadiazin-3yl methyl)benzoic acid tert-butyl ester was replaced with 7-bromo-2-(4-methoxy-benzyl)-1,1-dioxo-1,4-dihydro-2H-1λ$^6$-benzo[1,2,4]thiadiazin-3-one, the title compound 2-(4-methoxy-benzyl)-1,1-dioxo-7-(3-phenyl-prop-1-ynyl)-1,4-dihydro-2H-1λ$^6$-benzo[1,2,4]thiadiazin-3-one was obtained as a yellow solid. $^1$H-NMR (CDCl$_3$); δ 8.99 (s, 1H), 7.92 (s, 1H), 7.58 (dd, 1H), 7.33 (m, 8H), 6.91 (d, 1H), 6.83 (d, 2H), 5.01 (s, 2H), 3.83 (s, 2H), and 3.76 (s, 3H). MS: M$^+$−1=431.0 Da

EXAMPLE 19

4-[1,1,3-Trioxo-7-(4-phenyl-but-1-ynyl)-3,4-dihydro-1H-1λ$^6$-benzo[1,2,4]thiadiazin-2-ylmethyl]-benzoic acid Step (1): Synthesis of 4-[1,1,3-Trioxo-7-(4-phenyl-but-1-ynyl)-3,4-dihydro-1H-1λ$^6$-benzo[1,2,4]thiadiazin-2-ylmethyl]-benzoic acid tert-butyl ester

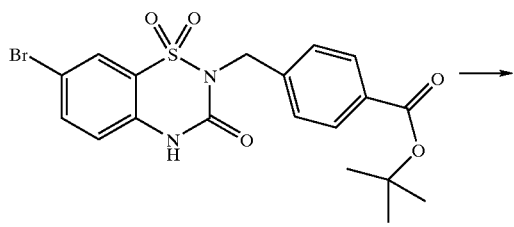

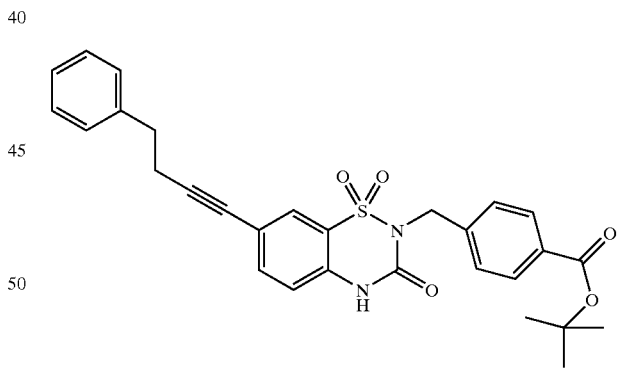

When in the procedure of Example 15, Step (4), 3-phenyl-1-propyne was replaced with 4-phenyl-1-butyne, the title compound 4-[1,1,3-trioxo-7-(4-phenyl-but-1-ynyl)-3,4-dihydro-1H-1λ$^6$-benzo[1,2,4]thiadiazin-2-ylmethyl]-benzoic acid tert-butyl ester was obtained as an off-white solid. $^1$H-NMR (CDCl$_3$); δ 9.08 (s, 1H), 7.94 (d, 2H), 7.81 (s, 1H), 7.52 (m, 3H), 7.28 (m, 5H), 6.81 (d, 1H), 5.08 (s, 2H), 2.92 (t, 2H) 2.71 (t, 2H), and 1.57 (s, 9H). MS: M$^+$−1=515.2 Da Step (2): Synthesis of 4-[1,1,3-Trioxo-7-(4-phenyl-but-1-ynyl)-3,4-dihydro-1H-1λ⁶ benzo[1,2,4]thiadiazin-2-ylmethyl]-benzoic acid

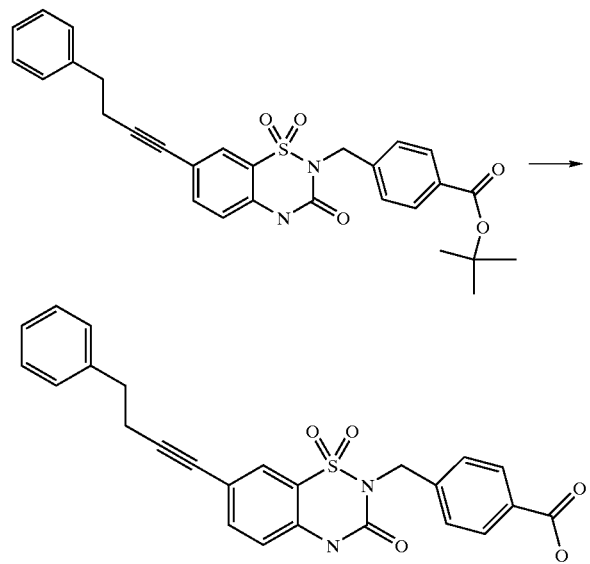

When in procedure of Example 15, Step (5), 4-[1-methyl-2,4-dioxo-6-(3-phenyl-prop-1-ynyl-1,4-dihydro-2H-2λ⁴-benzo[1,2,6]thiadiazin-3-ylmethyl]benzoic acid tert-butyl ester was replaced with 4-[1,1,3-trioxo-7-(4-phenyl-but-1-ynyl)-3,4-dihydro-1H-1λ⁶-benzo[1,2,4]thiadiazin-2-ylmethyl]-benzoic acid tert-butyl ester, the title compound 4-[1,1,3-trioxo-7-(4-phenyl-but-1-ynyl)-3,4-dihydro-1H-1λ⁶-benzo[1,2,4]thiadiazin-2-ylmethyl]-benzoic acid was obtained as a white solid. $^1$H-NMR (CDCl$_3$); δ 10.95 (s, 1H), 7.90 (d, 2H), 7.69 (s, 1H), 7.39 (m, 3H), 7.16 (m, 7H), 4.98 (s, 2H), 2.82 (t, 2H), and 2.60 (t, 2H). MS: M⁺+1=461.0 Da The invention compounds of Formula I have been evaluated in standard assays for their ability to inhibit the activity of various MMP enzymes. The assays used to evaluate the biological activity of the invention compounds are well-known and routinely used by those skilled in the study of MMP inhibitors and their use to treat clinical conditions.

The assays measure the amount by which a test compound reduces the hydrolysis of a thiopeptolide substrate caused by a matrix metalloproteinase enzyme. Such assays are described in detail by Ye et al., in *Biochemistry*, 1992;31 (45):11231–11235, which is incorporated herein by reference.

Thiopeptolide substrates show virtually no decomposition or hydrolysis in the absence of a matrix metalloproteinase enzyme. A typical thiopeptolide substrate commonly utilized for assays is Ac-Pro-Leu-Gly-thioester-Leu-Leu-Gly-OEt. A 100 μL assay mixture will contain 50 mM of 2-morpholinoethane sulfonic acid monohydrate (MES, pH 6.0) 10 mM CaCl$_2$, 100 μM thiopeptolide substrate, and 1 mM 5,5'-dithio-bis-(2-nitro-benzoic acid) (DTNB). The thiopeptolide substrate concentration is varied from 10 to 800 μM to obtain Km and Kcat values. The change in absorbance at 405 nm is monitored on a Thermo Max microplate reader (molecular Devices, Menlo Park, Calif.) at room temperature (22° C.). The calculation of the amount of hydrolysis of the thiopeptolide substrate is based on E$_{412}$= 13600 m⁻¹ cm⁻¹ for the DTNB-derived product 3-carboxy-4-nitrothiophenoxide. Assays are carried out with and without matrix metalloproteinase inhibitor compounds, and the amount of hydrolysis is compared for a determination of inhibitory activity of the test compounds.

Several representative compounds have been evaluated for their ability to inhibit various matrix metalloproteinase enzymes. Table 1 below presents inhibitory activity as IC$_{50}$'s in micromolar for representative invention compounds. In the table, MMP-1FL refers to full length interstitial collagenase; MMP-2FL refers to full length Gelatinase A; MMP-3CD refers to the catalytic domain of stromelysin; MMP-7FL refers to full length matrilysin; MMP-9FL refers to full length Gelatinase B; MMP-13CD refers to the catalytic domain of collagenase 3; and MMP-14CD refers to the catalytic domain of MMP-14. Test compounds were evaluated at various concentrations in order to determine their respective IC$_{50}$ values, the micromolar concentration of compound required to cause a 50% inhibition of the hydrolytic activity of the respective enzyme.

TABLE 1

IC$_{50}$ (μM) Versus MMPs

| Example No. | MMP01 (FL) | MMP02 (CD) | MMP02 (FL) | MMP03 (CD) | MMP07 (FL) | MMP09 (FL) | MMP13 (CD) | MMP14 (CD) |
|---|---|---|---|---|---|---|---|---|
| 1 | N/A[a] | N/A | N/A | N/A | N/A | N/A | 2.2 | N/A |
| 2 | N/A | N/A | N/A | N/A | N/A | N/A | 0.0042 | N/A |

[a]N/A means datum is not available.

The ability of the compounds of Examples 4 to 6 to inhibit the catalytic activity of MMP-13 CD is shown below in Table 2 in the column labeled "MMP-13CD (IC$_{50}$, μM)", wherein the activity is expressed as IC$_{50}$'s in micromolar concentration of compound.

TABLE 2

| Example No. | MMP-13CD (IC$_{50}$, μM) |
|---|---|
| 4 | 100 |
| 5 | 66 |
| 6 | 0.029 |

The abilities of the compounds of Examples 1 to 3 and 15 to 19 to inhibit the catalytic activity of MMP-13 CD, as well as the abilities of the compounds of Examples 1 to 3 and 15 to 18 to inhibit full-length MMP01, full-length MMP02, MMP03 catalytic domain, full-length MMP07, full-length MMP09, and MMP-14 catalytic domain, is shown below in Table 3 in the columns labeled "MMP-13 (CD)", and "MMP01 (FL)", "MMP02 (FL)", "MMP03 (CD)", "MMP07 (FL)", "MMP09 (FL)", and "MMP14 (CD)", respectively. In Table 3, the inhibitory activities are expressed as IC$_{50}$'s in micromolar concentration of compound.

TABLE 3

| Example No. | MMP01 (FL) | MMP02 (FL) | MMP03 (CD) | MMP07 (FL) | MMP09 (FL) | MMP13 (CD) | MMP14 (CD) |
|---|---|---|---|---|---|---|---|
| 1 | >100 | >30 | >30 | >30 | >100 | 2.2 | >100 |
| 2 | >30 | >30 | >10 | >30 | >30 | 0.0042 | >30 |
| 3 | >30 | >100 | >30 | >30 | >30 | 0.12 | >30 |
| 15 | >30 | >30 | >10 | 24 | >100 | 0.01045 | >30 |
| 16 | >30 | >30 | 12 | >30 | >30 | 0.0315 | >30 |
| 17 | >30 | >100 | 5.6 | 16 | >100 | 0.005167 | >30 |
| 18 | >30 | >30 | >30 | >10 | >30 | 0.185 | >30 |
| 19 | | | | | | 0.079 | |

The foregoing data establish that the invention compounds of Formula I are potent inhibitors of MMP enzymes, and are especially useful due to their selective inhibition of MMP-13. Because of this potent and selective inhibitory activity, the invention compounds are especially useful to treat diseases mediated by the MMP enzymes, and particularly those mediated by MMP-13.

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I, or a corresponding pharmaceutically acceptable salt of a compound of Formula I. The active compound generally is present in a concentration of about 5% to about 95% by weight of the formulation.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid that is in a mixture with the finely divided active component.

In tablets, the active component is mixed with the carrier having the necessary binding properties in suitable proportions and compacted in the shape and size desired.

The powders and tablets preferably contain from 5% or 10% to about 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizing, and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 1 to 1000 mg, preferably 10 to 100 mg according to the particular application and the potency of the active component. The composition can, if desired, also contain other compatible therapeutic agents.

In therapeutic use as agents to inhibit a matrix metalloproteinase enzyme for the treatment of atherosclerotic plaque rupture, aortic aneurism, heart failure, restenosis, periodontal disease, corneal ulceration, cancer metastasis, tumor angiogenesis, arthritis, or other autoimmune or inflammatory disorders dependent upon breakdown of connective tissue, the compounds utilized in the pharmaceutical method of this invention are administered at a dose that is effective to inhibit the hydrolytic activity of one or more matrix metalloproteinase enzymes. The initial dosage of about 1 mg/kg to about 100 mg/kg daily will be effective. A daily dose range of about 25 mg/kg to about 75 mg/kg is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages that are less than the optimum dose of the compound. Thereafter, the dosage is increased by small increments until the optimum effect under the circumstance is reached. For convenience, the total daily dosage may be divided and administered in portions during the day if desired. Typical dosages will be from about 0.1 mg/kg to about 500 mg/kg, and ideally about 25 mg/kg to about 250 mg/kg, such that it will be an amount that is effective to treat the particular disease being prevented or controlled.

The following examples illustrate typical formulations provided by the invention.

FORMULATION EXAMPLE 1

| Tablet Formulation | |
|---|---|
| Ingredient | Amount (mg) |
| Compound of Example 3 | 25 |
| Lactose | 50 |
| Corn starch (for mix) | 10 |
| Corn starch (paste) | 10 |
| Magnesium stearate (1%) | 5 |
| Total | 100 |

The alkyne of Example 3, lactose, and corn starch (for mix) are blended to uniformity. The corn starch (for paste) is suspended in 200 mL of water and heated with stirring to form a paste. The paste is used to granulate the mixed powders. The wet granules are passed through a No. 8 hand screen and dried at 80° C. The dry granules are lubricated with the 1% magnesium stearate and pressed into a tablet. Such tablets can be administered to a human from one to four times a day for treatment of atherosclerosis and arthritis.

FORMULATION EXAMPLE 2

| Preparation for Oral Solution | |
|---|---|
| Ingredient | Amount |
| Compound of Example 1 | 400 mg |
| Sorbitol solution (70% N.F.) | 40 mL |
| Sodium benzoate | 20 mg |
| Saccharin | 5 mg |
| Red dye | 10 mg |
| Cherry flavor | 20 mg |
| Distilled water q.s. | 100 mL |

The sorbitol solution is added to 40 mL of distilled water, and the alkyne of Example 1 is dissolved therein. The saccharin, sodium benzoate, flavor, and dye are added and dissolved. The volume is adjusted to 100 mL with distilled water. Each milliliter of syrup contains 4 mg of invention compound.

FORMULATION EXAMPLE 3
Parenteral Solution

In a solution of 700 mL of propylene glycol and 200 mL of water for injection is suspended 20 g of the compound of Example 2. After suspension is complete, the pH is adjusted to 6.5 with 1N sodium hydroxide, and the volume is made up to 1000 mL with water for injection. The formulation is sterilized, filled into 5.0-mL ampoules each containing 2.0 mL, and sealed under nitrogen.

As matrix metalloproteinase inhibitors, the compounds of Formula I are useful as agents for the treatment of multiple sclerosis. They are also useful as agents for the treatment of atherosclerotic plaque rupture, restenosis, periodontal disease, corneal ulceration, treatment of burns, decubital ulcers, wound repair, heart failure, cancer metastasis, tumor angiogenesis, arthritis, and other inflammatory disorders dependent upon tissue invasion by leukocytes.

What is claimed is:

1. A compound of Formula II

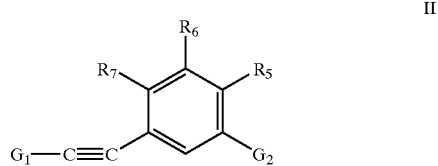

II or a pharmaceutically acceptable salt thereof, or a tautomer thereof, wherein:

$G_1$ is
 $(CH_2)_m$aryl,
 $(CH_2)_m$substituted aryl,
 $(CH_2)_m$heteroaryl, or
 $(CH_2)_m$substituted heteroaryl,

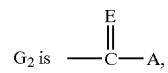

wherein
 E is O;
 A is $NR_1R_2$;
 $R_1$ is hydrogen;
 $R_2$ is
  $(CH_2)_n$aryl,
  $(CH_2)_n$substituted aryl,
  $(CH_2)_n$heteroaryl, or
  $(CH_2)_n$substituted heteroaryl;
 m is 1;
 n is 1;
 $R_5$, $R_6$, and $R_7$ independently are hydrogen, halo, hydroxy, $C_1$–$C_6$ alkyl, $C_2$–$C_6$ alkenyl, $C_2$–$C_6$ alkynyl, $C_1$–$C_6$ alkoxy, $NO_2$, CN, $CF_3$, or $NR_9R_{10}$, wherein $R_9$ and $R_{10}$ independently are hydrogen, $C_1$–$C_6$ alkyl, $C_3$–$C_7$ cycloalkyl, phenyl, or benzyl, or $R_9$ and $R_{10}$ are taken together with the nitrogen atom to which they are attached to complete a 3- to 7-membered ring having carbon atoms, the nitrogen atom bearing $R_9$ and $R_{10}$, and 0 or 1 heteroatoms selected from N(H), N($CH_3$), O, and S;
 wherein each aryl independently is phenyl or naphthyl;
 wherein each substituted aryl independently is phenyl or naphthyl substituted with from 1 to 3 substituents independently selected from selected from phenyl, cyano, $CO_2H$, $SO_2NH_2$, $CH_3SO_2$, $CH_3S$, alkyl, alkoxy, thio, thioalkyl, heteroaryl, heterocyclyl, halo, hydroxy, —$COOR_9$, trifluoromethyl, nitro, amino of the formula —$NR_1R_2$, and $T(CH_2)_mQR_3$ or $T(CH_2)_mCO_2R_3$, wherein m is 1 to 6; T is O, S, $NR_3$, N(O)$R_3$, $NR_1R_2Y$, or $CR_1R_2$, Q is O, S, $NR_3$, N(O)$R_3$, or $NR_1R_2Y$, wherein $R_1$ and $R_2$ are described above, and $R_9$ is alkyl or substituted alkyl;
 wherein each heteroaryl independently is selected from pyridyl, benzothienyl, furanyl, indolyl, benzotriazolyl, indazolyl, pyrrolyl, pyrazolyl, imidazolyl, thiazolyl, [1,2,3]triazolyl, [1,2,4]triazolyl, benzofuranyl, thienyl, benzisoxazolyl, benzisothiazolyl, isoxazolyl, isothiazolyl, and oxazolyl;

wherein each substituted heteroaryl is heteroaryl as defined above substituted with 1 or 2 substituents independently selected from alkyl, thio, and alkoxy.

2. The compound according to claim 1, or a pharmaceutically acceptable salt thereof, or a tautomer thereof, selected from:

3-(4-Methoxy-phenyl)-prop-1-ynyl)-N-(4-carboxybenzyl)-benzamide;
N-(4-Methanesulfonyl-benzyl)-3-(4-methoxy-phenyl)-prop-1-ynyl)-benzamide;
3-(3-Methoxy-phenyl)-prop-1-ynyl)-N-(4-carboxybenzyl)-benzamide;
N-(4-Methanesulfonyl-benzyl)-3-(3-methoxy-phenyl)-prop-1-ynyl)-benzamide;
3-(4-Cyano-phenyl)-prop-1-ynyl)-N-(4-carboxybenzyl)-benzamide;
N-(4-Methanesulfonyl-benzyl)-3-(4-cyano-phenyl)-prop-1-ynyl)-benzamide;
3-(3-Cyano-phenyl)-prop-1-ynyl)-N-(4-carboxybenzyl)-benzamide;
N-(4-Methanesulfonyl-benzyl)-3-(3-cyano-phenyl)-prop-1-ynyl)-benzamide;
3-(4-Fluoro-phenyl)-prop-1-ynyl)-N-(4-carboxybenzyl)-benzamide;
N-(4-Methanesulfonyl-benzyl)-3-(4-fluoro-phenyl)-prop-1-ynyl)-benzamide;
3-(3-Fluoro-phenyl)-prop-1-ynyl)-N-(4-carboxybenzyl)-benzamide;
N-(4-Methanesulfonyl-benzyl)-3-(3-fluoro-phenyl)-prop-1-ynyl)-benzamide;
3-(4-Chloro-phenyl)-prop-1-ynyl)-N-(4-carboxybenzyl)-benzamide;
N-(4-Methanesulfonyl-benzyl)-3-(4-chloro-phenyl)-prop-1-ynyl)-benzamide;
3-(3-Chloro-phenyl)-prop-1-ynyl)-N-(4-carboxybenzyl)-benzamide;
N-(4-Methanesulfonyl-benzyl)-3-(3-chloro-phenyl)-prop-1-ynyl)-benzamide;
3-(4-Bromo-phenyl)-prop-1-ynyl)-N-(4-carboxybenzyl)-benzamide;
N-(4-Methanesulfonyl-benzyl)-3-(4-bromo-phenyl)-prop-1-ynyl)-benzamide;
3-(3-Bromo-phenyl)-prop-1-ynyl)-N-(4-carboxybenzyl)-benzamide;
N-(4-Methanesulfonyl-benzyl)-3-(3-bromo-phenyl)-prop-1-ynyl)-benzamide;
3-(4-Methanesulfanyl-phenyl)-prop-1-ynyl)-N-(4-carboxybenzyl)-benzamide;
N-(4-Methanesulfonyl-benzyl)-3-(4-methanesulfanyl-phenyl)-prop-1-ynyl)-benzamide;
3-(3-Methanesulfanyl-phenyl)-prop-1-ynyl)-N-(4-carboxybenzyl)-benzamide;
N-(4-Methanesulfonyl-benzyl)-3-(3-methanesulfanyl-phenyl)-prop-1-ynyl)-benzamide;
3-(4-Methyl-phenyl)-prop-1-ynyl)-N-(4-carboxybenzyl)-benzamide;
N-(4-Methanesulfonyl-benzyl)-3-(4-methyl-phenyl)-prop-1-ynyl)-benzamide;
3-(3-Methyl-phenyl)-prop-1-ynyl)-N-(4-carboxybenzyl)-benzamide;
N-(4-Methanesulfonyl-benzyl)-3-(3-methyl-phenyl)-prop-1-ynyl)-benzamide;
3-(3-Pyridin-4-yl-prop-1-ynyl)-N-(4-carboxybenzyl)-benzamide;
N-(4-Methanesulfonyl-benzyl)-3-(3-pyridin-4-yl-prop-1-ynyl)-benzamide;
3-(3-Pyridin-3-yl-prop-1-ynyl)-N-(4-carboxybenzyl)-benzamide;
N-(4-Methanesulfonyl-benzyl)-3-(3-pyridin-3-yl-prop-1-ynyl)-benzamide;
3-[3-(2-Methoxy-pyridin-4-yl)-prop-1-ynyl]-N-(4-carboxybenzyl)-benzamide; and
N-(4-Methanesulfonyl-benzyl)-3-[3-(2-methoxy-pyridin-4-yl)-prop-1-ynyl]-benzamide.

3. The compound according to claim 1, selected from:
N-(4-Cyano-benzyl)-3-(3-[1,2,3]-triazol-1-yl-prop-1-ynyl)-benzamide;
N-(4-Cyano-benzyl)-3-(3-[1,2,3]-triazol-1-yl-prop-1-ynyl)-benzamide;
4-({3-[3-(4-Chloro-phenyl)-prop-1-ynyl]-benzoylamino}-methyl)-benzoic acid;
4-({3-[3-(4-Fluoro-phenyl)-prop-1-ynyl]-benzoylamino}-methyl)-benzoic acid;
3-Phenylethynyl-N-(4-Sulfamoyl-benzyl)-benzamide;
N-(4-Cyano-benzyl)-3-phenylethynyl-benzamide:
3-Phenylethylethynyl-N-pyridin-4-yl-methyl-benzamide; and
3-[[3-(3-Phenylethylethynyl-benzoylamino]-methyl}-benzoic acid; or a pharmaceutically acceptable salt thereof.

4. A compound of Formula II

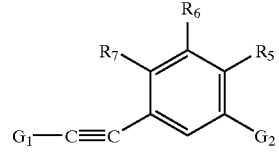

or a pharmaceutically acceptable salt thereof, or a tautomer thereof, wherein:

$G_1$ and $G_2$ independently are
$(CH_2)_m$aryl, wherein m is 1 and aryl is phenyl,
$(CH_2)_m$substituted aryl, wherein m is 1 and substituted aryl is 4-methoxyphenyl, 3-methoxyphenyl, 4-fluorophenyl, 3-fluorophenyl, 4-chlorophenyl, 3-chlorophenyl, 4-bromophenyl, 3-bromophenyl, 4-nitrophenyl, 3-nitrophenyl, 4-methylsulfanylphenyl, 3-methylsulfanylphenyl, 4-methylphenyl, 3-methylphenyl, 4-cyanophenyl, 3-cyanophenyl, 4-carboxyphenyl, 3-carboxyphenyl, 4-methanesulfonylphenyl, or 3-methanesulfonylphenyl,
$(CH_2)_m$heteroaryl, wherein m is 1 and heteroaryl is pyridin-4-yl, pyridin-3-yl, or pyridin-2-yl, or
$(CH_2)_m$substituted heteroaryl, wherein m is 1 and substituted heteroaryl is 2-methoxypyridin-4-yl; and $R_5$, $R_6$, and $R_8$ are hydrogen.

5. A pharmaceutical composition, comprising a compound of claim 1, or a pharmaceutically acceptable salt thereof, or a tautomer thereof, together with a pharmaceutically acceptable carrier, diluent, or excipient.

6. A method for treating rheumatoid arthritis, comprising administering to a patient in need of treatment an antiarthritic amount of a compound of claim 1, or a pharmaceutically acceptable salt thereof, or a tautomer thereof.

* * * * *